US008445664B2

(12) United States Patent
Rabbani et al.

(10) Patent No.: US 8,445,664 B2
(45) Date of Patent: May 21, 2013

(54) KITS FOR AMPLIFYING AND DETECTING NUCLEIC ACID SEQUENCES

(75) Inventors: Elazar Rabbani, New York, NY (US); Jannis Stavrianopoulos, Bay Shore, NY (US); James J. Donegan, Long Beach, NY (US); Jack Coleman, East Northport, NY (US); Marleen Walner, Farmingdale, NY (US)

(73) Assignee: Enzo Diagnostics, Inc., Farmingdale, NY (US)

(*) Notice: Subject to any disclaimer, the term of this patent is extended or adjusted under 35 U.S.C. 154(b) by 413 days.

(21) Appl. No.: 11/256,592

(22) Filed: Oct. 20, 2005

(65) Prior Publication Data

US 2008/0070241 A1 Mar. 20, 2008

Related U.S. Application Data

(62) Division of application No. 10/306,990, filed on Nov. 29, 2002, now abandoned, which is a division of application No. 09/439,594, filed on Nov. 12, 1999, now Pat. No. 6,764,821, which is a division of application No. 09/104,067, filed on Jun. 24, 1998, now Pat. No. 6,743,605.

(51) Int. Cl.
*C07H 21/04* (2006.01)

(52) U.S. Cl.
USPC ........................................ 536/24.33; 435/975

(58) Field of Classification Search
None
See application file for complete search history.

(56) References Cited

U.S. PATENT DOCUMENTS

| 4,683,202 A | 7/1987 | Mullis |
| 4,707,440 A | 11/1987 | Stavrianopoulos |
| 4,729,947 A | 3/1988 | Middendorf et al. |
| 4,749,647 A | 6/1988 | Thomas et al. |
| 5,027,880 A | 7/1991 | Morii et al. |
| 5,047,519 A | 9/1991 | Hobbs |
| 5,093,232 A | 3/1992 | Urdea et al. |
| 5,171,534 A | 12/1992 | Smith et al. |
| 5,230,781 A | 7/1993 | Middendorf et al. |
| 5,241,060 A | 8/1993 | Engelhardt et al. |
| 5,260,433 A | 11/1993 | Engelhardt et al. |
| 5,270,184 A * | 12/1993 | Walker et al. ............ 435/91.2 |
| 5,328,824 A | 7/1994 | Ward et al. |
| 5,332,666 A | 7/1994 | Prober et al. |
| 5,346,603 A | 9/1994 | Middendorf et al. |
| 5,360,523 A | 11/1994 | Middendorf et al. |
| 5,439,793 A | 8/1995 | Rose et al. |
| 5,462,584 A | 10/1995 | Gavlin et al. |
| 5,462,854 A | 10/1995 | Coassin et al. |
| 5,470,723 A | 11/1995 | Walker et al. |
| 5,474,796 A * | 12/1995 | Brennan .................. 427/2.13 |
| 5,476,928 A | 12/1995 | Ward et al. |
| 5,508,178 A | 4/1996 | Rose et al. |
| 5,563,050 A | 10/1996 | Peyman et al. |
| 5,569,582 A | 10/1996 | Tavernarakis et al. |
| 5,595,891 A | 1/1997 | Rose et al. |
| 5,610,017 A | 3/1997 | Gudibande et al. |
| 5,612,199 A | 3/1997 | Westerm et al. |
| 5,683,872 A | 11/1997 | Rudert et al. |
| 5,714,323 A | 2/1998 | Ohshima et al. |
| 5,798,276 A | 8/1998 | Haugland et al. |
| 5,874,260 A | 2/1999 | Cleuziet et al. |
| 6,114,123 A * | 9/2000 | Murry et al. .................. 435/6 |
| 6,114,150 A * | 9/2000 | Weissman et al. ......... 435/91.2 |
| 6,124,120 A * | 9/2000 | Lizardi .................... 435/91.2 |
| 6,326,145 B1 | 12/2001 | Whitcombe et al. |
| 6,410,278 B1 | 6/2002 | Notomi et al. |
| 6,974,670 B2 | 12/2005 | Notomi et al. |
| 7,851,186 B2 | 12/2010 | Nagamine et al. |
| 2002/0168676 A1 * | 11/2002 | Notomi et al. .................. 435/6 |
| 2004/0132144 A1 | 7/2004 | Notomi et al. |

FOREIGN PATENT DOCUMENTS

| DE | 265429 | 9/1987 |
| EP | 0 549 107 | 6/1993 |
| EP | 0302308 B1 | 11/1993 |
| EP | 713922 A1 | 5/1996 |
| EP | 023149 B1 | 6/1999 |

(Continued)

OTHER PUBLICATIONS

Stratagene ("Gene Characterization Kits" 1988).*
Saiki, R.K. et al., *Science* 230:1350-1354 (1985).
Meyers, T.W. and Gelfand, D.H., *Biochemistry* 30(31):7661-7666 (1991).
Landegren U. et al., *Science* 241:1077 (1988).
Wu D. and Wallace, R.B., *Genomics* 4:560-569 (1989).
Barany F., *Proc. Natl. Acad. Sci.* (USA) 88:189-193 (1991).
Kwoh D.Y. et al., *Proc. Natl. Acad. Sci.* (USA) 86:1173-1177 (1989).
Kievits, T. et al., *Journal of Virological Methods* 35:273-286 (1991).
Walker, G.T. et al., *Proc. Natl. Acad. Sci.* (USA) 89:392-396 (1992).

(Continued)

*Primary Examiner* — Christopher M. Babic
(74) *Attorney, Agent, or Firm* — Anna DiGabriele Petti, Esq.

(57) ABSTRACT

This invention provides novel processes for amplifying nucleic acid sequences of interest, including linear and non-linear amplification. In linear amplification, a single initial primer or nucleic acid construct is utilized to carry out the amplification process. In non-linear amplification, a first initial primer or nucleic acid construct is employed with a subsequent initial primer or nucleic acid construct. In other non-linear amplification processes provided by this invention, a first initial primer or nucleic acid construct is deployed with a second initial primer or nucleic acid construct to amplify the specific nucleic acid sequence of interest and its complement that are provided. A singular primer or a singular nucleic acid construct capable of non-linear amplification can also be used to carry out non-linear amplification in accordance with this invention. Post-termination labeling process for nucleic acid sequencing is also disclosed in this invention that is based upon the detection of tagged molecules that are covalently bound to chemically reactive groups provided for chain terminators. A process for producing nucleic acid sequences having decreased thermodynamic stability to complementary sequences is also provided and achieved by this invention. Unique nucleic acid polymers are also disclosed and provided in addition to other novel compositions, kits and the like.

35 Claims, 30 Drawing Sheets

FOREIGN PATENT DOCUMENTS

| | | |
|---|---|---|
| EP | 00 971 039 A3 | 1/2004 |
| GB | 2338302 B | 8/2000 |
| WO | WO9200989 | 1/1992 |
| WO | WO 9502690 A1 | 1/1995 |
| WO | WO 9503426 A2 * | 2/1995 |
| WO | WO 96/01327 A1 | 1/1996 |
| WO | WO9704131 | 7/1996 |
| WO | WO 97/00330 A2 | 1/1997 |
| WO | WO 97/04131 | 2/1997 |
| WO | WO9806732 | 2/1998 |
| WO | WO9843991 | 10/1998 |
| WO | WO 99/09211 A1 | 2/1999 |
| WO | WO 00/28082 A1 | 5/2000 |
| WO | WO 01/34790 A1 | 5/2001 |
| WO | WO 01/34838 A1 | 5/2001 |

OTHER PUBLICATIONS

Saiki R.K. et al., Science 239:487-491 (1988).
Auer, T. et al., Nucleic Acids Research 24(24):5021-5025 (1996).
Maxam A. M. and Gilbert, W., Proc. Natl. Acad. Sci. (USA) 74(2):560-564 (1977).
Sanger F., et al., Proc. Natl. Acad. Sci. (USA) 74(12):5463-5467 (1977).
Beck S., et al., Nucleic Acids Research 17(13):5115-5123 (1989).
Ansorge W., et al., Journal of Biochemical and Biophysical Methods 13:315-323 (1986).
Sequeriase Images™ Protocol Book, United States Biochemical Corporation, Cleveland, Ohio, pp. 106-107 (1993).
Beck S., Methods in Enzymology 184:612-617 (1990).
Wetmur J.G., Critical Reviews in Biochemistry and Molecular Biology 26(3/4):227-259 (1991).
Kornberg A. and Baker T.A., DNA Replication, $2^{nd}$ Edition, W.H. Freeman and Co., New York, New York, pp. 44-46 (1992).
Adams, R.L.P. et al., The Biochemistry of the Nucleic Acids, Chapman & Hall, London, U.K., p. 31 (1992).
Prober J.M., et al., Science 238:336-341 (1987).
Kornberg A. and Baker T.A., DNA Replication, $2^{nd}$ Edition, W.H. Freeman and Co., New York, New York, pp. 447-449 (1992).
Wilton, S.D. et al., "Snapback SSCP Analysis: Engineered Conformation Changes for the Rapid Typing of Known Mutations," Human Mutation 11:252-258 (1998).
Patel, R. et al., "Formation of chimeric DNA primer extension products by template switching onto an annealed downstream oligonucleotide," Proc. Natl. Acad. Sci. (USA) 93:2969-2974 (1996).
Walker, G.T et al., "Strand displacement amplification—an isothermal, in vitro DNA amplification technique," Nucleic Acids Research 20(7):1691-1696 (1992).
Kurfurst, R. et al., "Oligo-alpha-Deoxyribonucleotides with a Modified Nucleic Base and Covalently Linked to Reactive Agents," Tetrahedron 49(32):6975-6990 (1993).
Honeyman K. et al., "Development of a snapback method of single-strand conformation polymorphism analysis for genotyping Golden Retriever for the X-linked muscular dystrophy allele," AJVR 60(6):734-737 (1999).
Whitcombe, D. et al., Nature Biotechnology 17:804-807 (1999).

Grein, T., et al., "Deaza and 7 Deazapurines: duplex stability of oligonucleotides containing modified adenine or guanine bases," Bioorganic & Medicinal Chemistry Letters 4:971-976 (1994).
Sagi, J., et al., "Base-modified oligodeoxynucleotides. I. effect of 5-alkyl, 5-(1-alkenyl) and 5-(1-alkynyl) substitution of the pyrmidines on duplex stability and hydrophobicity," Tetrahedron Letters 34:2191-2194 (1993).
Sanghvi, Y.S., "Heterocyclic Base Modifications in Nucleic Acids and their Applications in Antisense Oligonucleotides," Chapter 15 (pp. 273-288) of Antisense Research and Applications, CRC Press, UK (1993).
Sowers, L.C., et al., "Equilibrium between a Wobble and Ionized Base Pair Formed between Fluorouracil and Guanine in DNA as Studied by Proton and Fluorine NMR," J. Bio. Chem. 263:14794-14801 (1988).
Lee et al., Novel Pre-C/C Gene Mutants of Hepatitis B Virus in Chronic Active Hepatitis, J. of General Virology 1996;77:1129-1138.
Genbank GI:21326584[Online] October 8, 2008 [Retrieved on Oct. 23, 2008] Retireved From HTTP://WWW.NCBI.NLM.NIH.GOV/SITES/ENTREZ?DB=NUCCORE&CMD=SEARCH&TERM=21326584 (4 Pages).
Dong et al., Secondary Structure Prediction and Structure-Specific Sequence Analysis . . . , Nucleic Acids Research 2001;29(15):3248-3257.
Chavali et al., Oligonucleotide Prperties Determination and Primer Designing . . . , Bioinformatics, 2005;21(20):3918-3925.
Paterlini et al, Selective Accumulation of the X Transcript of Hepatitis B Virus in Patients Negative for Hepatitis B Surface Antigen . . . Hepatology 1995;21(2):313-321.
Notomi T, et al., Loop Mediated Isothermal Amplification of DNA, Nucleic Acids Research, Jun. 15, 2000, vol. 28. No. 12, pp. E63-E67.
Nagamine, Kentaro et al., Isolation of single stranded DNA from loop-mediated isothermal . . . , Biochemical & Biophysical Res Comms, vol. 290, No. 4, Feb. 1, 2002, pp. 1195-1198.
Tsugunori, Iritomi et al., Shinki Idenshi Zofuko hou (LAMP hou) no Genri to Ouyou, Bio Industry, Feb. 2001, vol. 18, No. 2, pp. 15-23.
Pollack et al., An RNA stem-loop structure directs hepatits B virus genomic RNA encapsidation, J. Virol Jun. 1993; 67(6): 3254-3263.
Blanco et al., Highly efficient DNA synthesis by the phage phi 29 DNA polymerase. Symmetrical mode of DNA replication. J Biol Chem May 25, 1989 264(15):8935-40.
GenBank GI: 310749, 4 pages.
Output from http://www.bioinfo.rpi.edu/applications/mfold/dna, 7 pages.
Zucker, M., Mfold web server for nucleic acid folding and hybridization prediction, Nucleic Acid Res. 31(13):3406-3415, 2003.
Lodmell et al., Genetic and comparative analysis reveal an alternative secondary structure in the region of nt 912 of . . . 1995 Proc Natl Acad Sci USA vol. 92, pp. 10555-10559.
Kremsky et al., Immobilization of DNA via oligonucleotides containing an aldehyde or carboxylic acid group at the 5' terminus, Nuci Acid Res Apr. 10, 1987 15(7):2891-909.

* cited by examiner

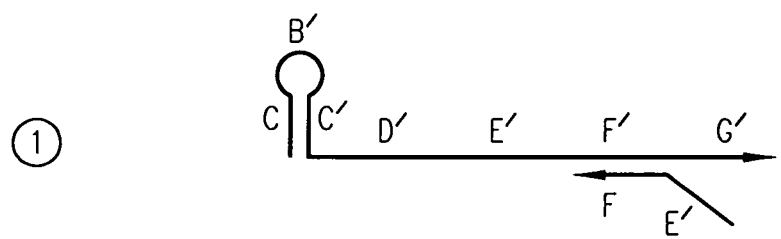
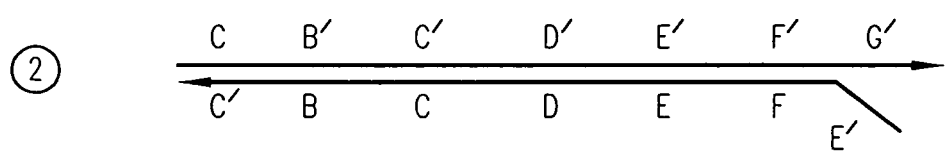
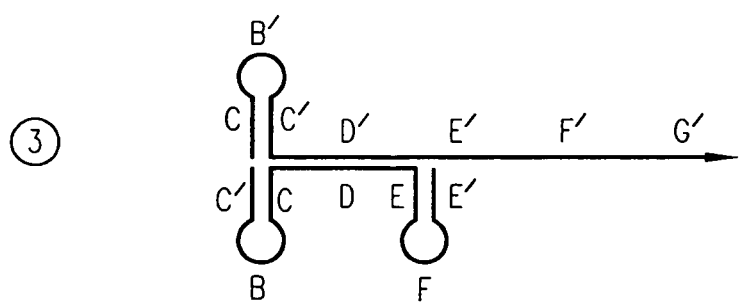
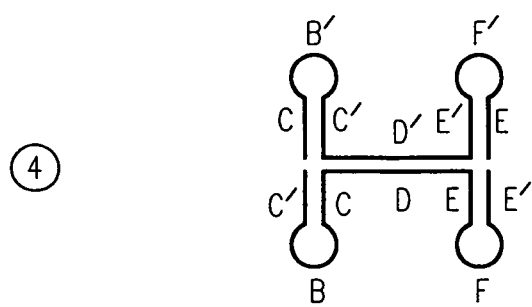
FIG. 3

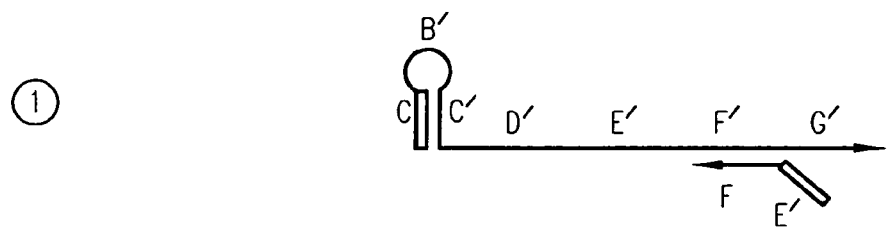
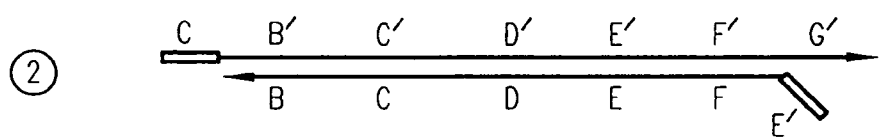
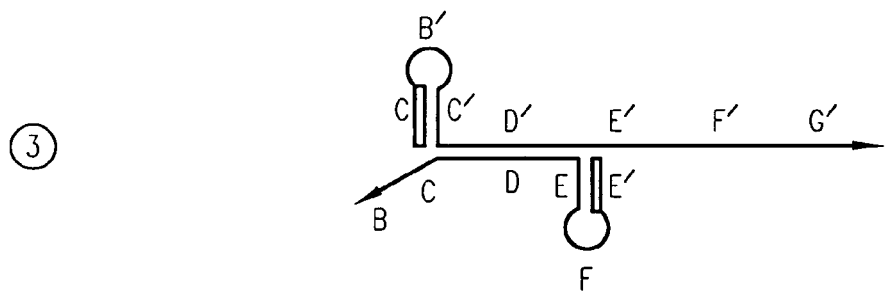
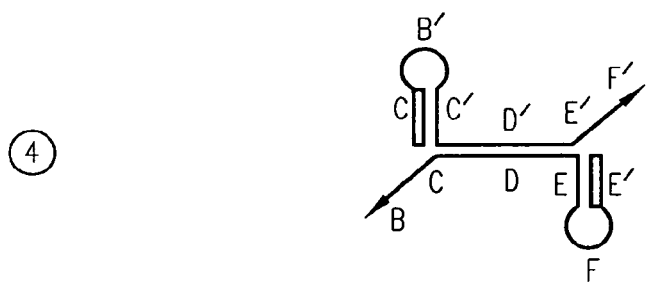
FIG. 4

① 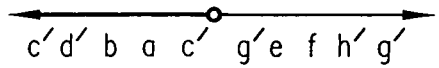
② 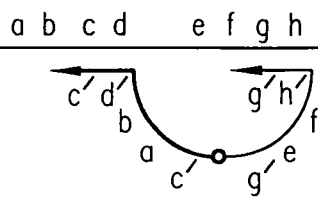
③ 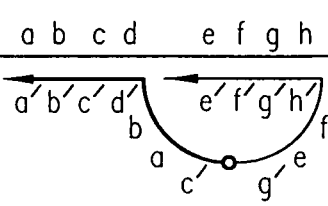
④ 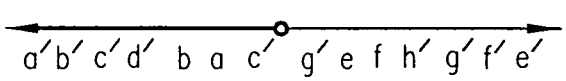
⑤ 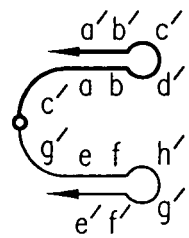
⑥ 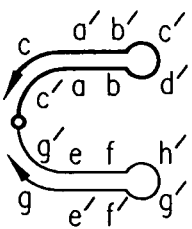
⑦ 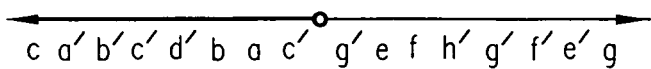
FIG. 13

① 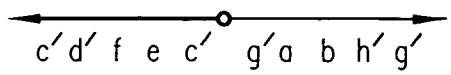
② 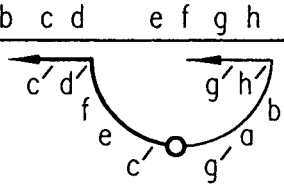
③ 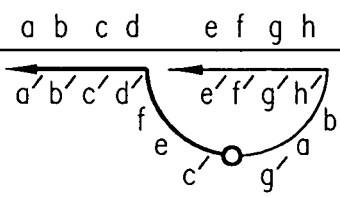
④ 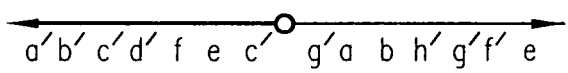
⑤ 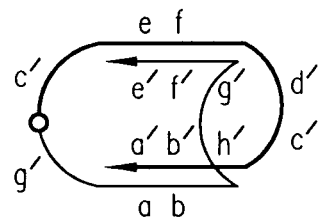
⑥ 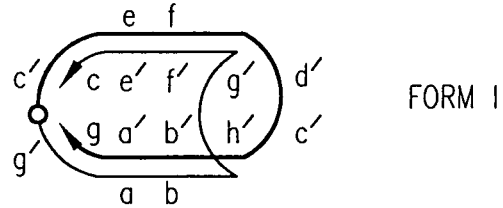   FORM I
⑦ 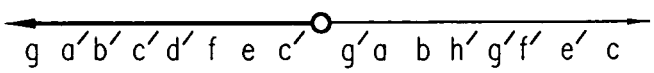
FIG. 15

| A | B |
|---|---|
| 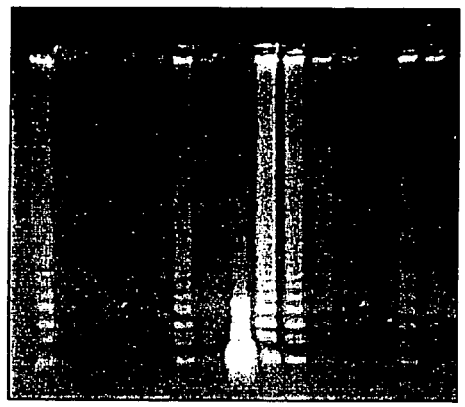 | 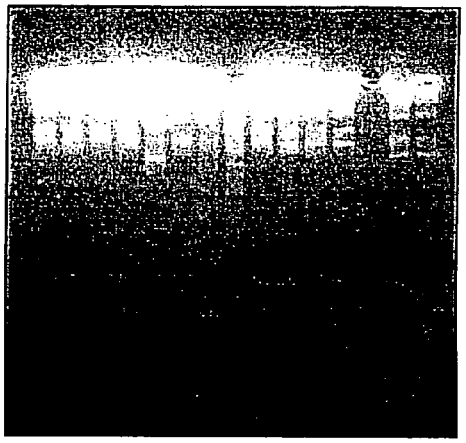 |
| 30 MINUTES INCUBATION | 180 MINUTES INCUBATION |
1   53°C, $10^{-2}$ DILUTION
2   53°C, $10^{-3}$ DILUTION
3   53°C, $10^{-4}$ DILUTION
4   53°C, $10^{-5}$ DILUTION
5   53°C, NO TARGET
6   53°C, $10^{-2}$ DILUTION, FC/LRC
7   53°C, $10^{-2}$ DILUTION, LFC/RC
8     MSP I MARKER
9   63°C, $10^{-2}$ DILUTION
10  63°C, $10^{-3}$ DILUTION
11  63°C, $10^{-4}$ DILUTION
12  63°C, $10^{-5}$ DILUTION
13  63°C, NO TARGET
14  63°C, $10^{-2}$ DILUTION, FC/LRC
15  63°C, $10^{-2}$ DILUTION, LFC/RC
FIG. 17

A) GEL ASSAY

TOP = ISOTHERMAL AMPLIFICATION
BOTTOM = PCR AMPLIFICATION

1     MSP I MARKER
2     1 x $10^6$ TARGET
3     1 x $10^4$ TARGET
4     1 x $10^2$ TARGET
5     NO TARGET

B) PLATE ASSAY

| $10^6$ TARGET | $10^4$ TARGET | $10^2$ TARGET | TARGET |
|---|---|---|---|
| 1.702 | 1.594 | 0.376 | 0.085 |

1   CARBOXY-U, KLENOW 37°C, NEB #2
2   NORMAL T, KLENOW, 37°C, NEB #2
3   CARBOXY-U, KLENOW, 37°C, BUFFER #2A
4   NORMAL T, KLENOW, 37°C, BUFFER #2A
5   CARBOXY-U, KLENOW, 55°C, NEB #2
6   NORMAL T, KLENOW, 55°C, NEB #2
7         MSP I MARKER
8   CARBOXY-U, TAQ, 55°C, NEB #2
9   NORMAL T, TAQ, 55°C, NEB #2
10  CARBOXY-U, TAQ, 65°C, BUFFER #2M
11  NORMAL T, TAQ, 65°C, BUFFER #2M
12  CARBOXY-U, BST, 65°C, THERMOPOL BUFFER
13  NORMAL T, BST, 65°C, THERMOPOL BUFFER
14  CARBOXY-U, TAQ, 65°C, BUFFER #2A
15  NORMAL T, TAQ, 65°C, BUFFER #2A

| ENZYME | BUFFER | TEMPERATURE | NUCLEOTIDE | RELATIVE LEVEL OF SYNTHESIS |
|---|---|---|---|---|
| KLENOW | NEB #2 | 37°C | CARBOXY U | + |
|  |  |  | NORMAL T | +++ |
| KLENOW | 2A | 37°C | CARBOXY U | − |
|  |  |  | NORMAL T | ++ |
| KLENOW | NEB #2 | 55°C | CARBOXY U | + |
|  |  |  | NORMAL T | +++ |
| TAQ | NEB #2 | 55°C | CARBOXY U | ++ |
|  |  |  | NORMAL T | ++++ |
| TAQ | 2M | 65°C | CARBOXY U | ++ |
|  |  |  | NORMAL T | ++++ |
| BST | THERMOPOL | 65°C | CARBOXY U | ++ |
|  |  |  | NORMAL T | ++++ |
| TAQ | 2A | 65°C | CARBOXY U | +/− |
|  |  |  | NORMAL T | +++ |

FIG. 20

1. MSP I/BST E II MARKER
2. NORMAL T, 1 mM MgCl$_2$
3. CARBOXY U, 2 mM MgCl$_2$
4. CARBOXY U, 3 mM MgCl$_2$
5. CARBOXY U, 4 mM MgCl$_2$
6. CARBOXY U, 5 mM MgCl$_2$
7. MSP I/BST E II MARKER

1. MSP I/BST E II MARKER
2. NORMAL T, TAQ
3. CARBOXY U, TAQ
4. NORMAL T, Tfl
5. CARBOXY U, Tfl
6. NORMAL T, Tth
7. CARBOXY U, Tth
8. NORMAL T, AMPLITHERM
9. CARBOXY U, AMPLITHERM
10. NORMAL T, REPLITHERM
11. CARBOXY U, REPLITHERM
12. MSP I/BST E II MARKER

1. TAQ, 2mM $MgCl_2$
2. TAQ, 4mM $MgCl_2$
3. TAQ, 6mM $MgCl_2$
4. Tfl, 2mM $MgCl_2$
5. Tfl, 4mM $MgCl_2$
6. Tfl, 6mM $MgCl_2$
7. MSP I MARKER
8. Tfl/Enh, 2mM $MgCl_2$
9. Tfl/Enh, 4mM $MgCl_2$
10. Tfl/Enh, 6mM $MgCl_2$

1. Tth/Enh, 4mM $MgCl_2$
2. Tth/Enh, 6mM $MgCl_2$
3. Tth/Enh, 8mM $MgCl_2$
4. Msp I/BspE1 MARKER
5. AMPLITHERM/ Enh, 4mM $MgCl_2$
6. AMPLITHERM/ Enh, 6mM $MgCl_2$
7. AMPLITHERM/ Enh, 8mM $MgCl_2$
8. Msp I/BspE1 MARKER
9. REPLITHERM/ Enh, 4mM $MgCl_2$
10. REPLITHERM/ Enh, 6mM $MgCl_2$
11. REPLITHERM/ Enh, 8mM $MgCl_2$

1. Msp I MARKER
2. 0.3X ENHANCER
3. CONTROL
4. DEAZA G
5. GENE 32
6. 10% DMSO
7. 3X POLYMERASE

SEQ ID 11
5'-TGC GCT GCT AAC AAA GCC CGA AAG GAA G--------GCT GAA AGG AGG AAC TAT ATG GCG TCA TAC GAT ATG AAC GTT-3'
3'-ACG CCA CCA TTG TTT CGG GCT TTC CTT C--------CGA CTT TCC TCC TTG ATA TAC GCG AGT ATG CTA TAC TTG CAA-5'
SEQ ID 12

TS-13   SEQ ID 13
5'-AAT CTA GA GCT AAC AAA GCC CGA AAG GAA G-3'

TS-21   SEQ ID 14
5'-TGC GCT GCT AAC AAA GCC CGA AAG GAA G-3'

TS-22   SEQ ID 15
5'-ACC CGC GCT GCT AAC AAA GCC CGA AAG GAA G-3'

SEQ ID 16   TS-14
3'-CGA CTT TCC TCC TTG ATA TA GAC GTC TT-5'

SEQ ID 17   TS-23
3'-CGA CTT TCC TCC TTG ATA TAC GCG AGT -5'

SEQ ID 18   TS-24
3'-G ATA TAC GCG AGT ATG CTA TAC TTG CAA-5'

FIG. 26

1. Msp I MARKER
2. TS13 + TS14
3. TS13 + TS23
4. TS13 + TS24
5. TS21 + TS14
6. TS21 + TS23
7. TS21 + TS24
8. TS22 + TS14
9. TS22 + TS23
10. TS22 + TS24
11. Msp I MARKER
12. TS13 + TS14 (DIFFERNT LOT OF C-U)
13. TS13 + TS14 (ALLYLAMINE dUTP)
14. TS13 + TS14 (NORMAL dTTP)

1. TS13 + TS14
2. TS13 + TS23
3. TS13 + TS24
4. Msp I MARKER
5. TS21 + TS14
6. TS21 + TS23
7. TS21 + TS24
8. TS22 + TS14
9. TS22 + TS23
10. TS22 + TS24
11. Msp I MARKER

FLOURESCENT DETECTION
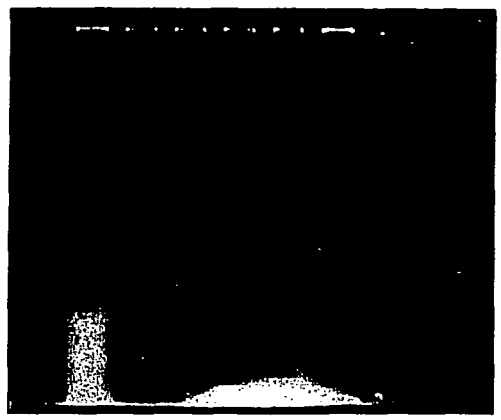
ETHIDIUM BROMIDE FLOURESCENCE
1    1 x TAPS, pH 9.2
2    2 x TAPS, pH 9.2
3    3 x TAPS, pH 9.2
4    3 x TAPS, pH 9.7
5    3 x TAPS, pH 9.2
6    3 x TAPS, pH 8.6
7    NO ENZYME CONTROL
8    FLUORESCEIN 12-ddUTP CONTROL
FIG. 29

FLOURESCENT DETECTION
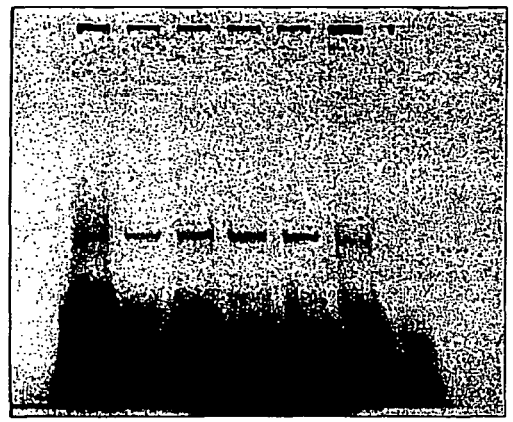
ETHIDIUM BROMIDE FLOURESCENCE
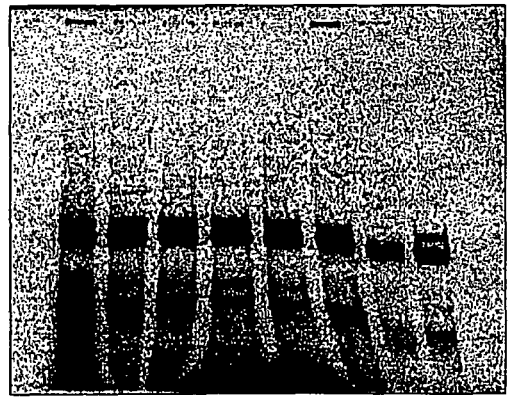
1   1 x TAPS, pH 9.2
2   2 x TAPS, pH 9.2
3   3 x TAPS, pH 9.2
4   3 x TAPS, pH 9.7
5   3 x TAPS, pH 9.2
6   3 x TAPS, pH 8.6
7   NO ENZYME CONTROL
8   FLUORESCEIN 12-ddUTP CONTROL
*FIG. 30*

KITS FOR AMPLIFYING AND DETECTING NUCLEIC ACID SEQUENCES

This application is a divisional application of U.S. patent application Ser. No. 10/306,990, filed Nov. 29, 2002, abandoned, which is a divisional application of U.S. patent application Ser. No. 09/439,594, filed Nov. 12, 1999, now U.S. Pat. No. 6,764,821, issued Jul. 20, 2004, which application is a divisional of Ser. No. 09/104,067, filed on Jun. 24, 1998, now U.S. Pat. No. 6,743,605, issued Jun. 1, 2004. This application claims priority to Ser. No. 09/104,067, filed Jun. 1, 2004.

The material on the compact disc, file name, sequence ListingEnz58D11D1.txt, created on Nov. 15, 2007, with a size of 14,336 bytes is hereby incorporated by reference in its entirety.

FIELD OF THE INVENTION

This invention relates to the field of recombinant nucleic acid technology, and more particularly, to processes for nucleic acid amplification, the post-termination labeling for nucleic acid sequencing and the production of nucleic acid having decreased thermodynamic stability.

All patents, patent applications, patent publications, scientific articles, and the like, cited or identified in this application are hereby incorporated by reference in their entirety in order to describe more fully the state of the art to which the present invention pertains.

BACKGROUND OF THE INVENTION

The first system described for the successful in vitro exponential amplification of target nucleic acids is the Polymerase Chain Reaction (PCR) (Saiki et al., 1985 Science 230; 1350-1354). PCR has been widely used for allele determination, forensic identification, gene analysis, diagnostics, cloning, direct sequencing and other applications. Subsequently, Reverse Transcriptase (RT) was used to transform an RNA molecule into a DNA copy allowing the use of RNA molecules as substrates for PCR amplification by DNA polymerase. In addition, conditions have been described that allow certain DNA polymerases to perform reverse transcription by themselves (Myers, T. W. and Gelfand, D, H. [1991] Biochem. 30; 7661-7666), contents incorporated herein by refernce. Finally, Rose et al. (U.S. patent #5,508,178, also incorporated herein by reference) have described the use of inverted repeat sequences as choices for PCR primer sequences, allowing the use of a single primer to initiate polymerization from each end of a target nucleic acid to create a P09 amplicon that in single-stranded form can be drawn as a "pan-handles" with self complementary sequences at each end. In order to utilize targets that lack inverted repeats, this group has also described various methods to introduce sequences into a PCR amplicon, such that the final product would have self-complementary sequences at each end (U.S. Pat. Nos. 5,439,793, 5,595,891, and 5,612,199, each of which is incorporated herein by reference).

Both the original PCR amplification system and various improved PCR systems suffer from the limitation of a necessity for expensive dedicated thermocyclers to provide the multiple temperature conditions that are intrinsic to the PCR method. This necessity is derived from the problem that the extension of a primer creates a product that has a stronger association with a template that the primer used to create it. As such, in a system like PCR, temperatures that allow binding of a primer are too low to allow separation of the extended product from its template and temperatures that are elevated enough to allow the separation of the extended product are too high to allow another priming event. The second priming event cannot take place until after the first extended strand is separated from its template. As such, in PCR amplification, primer binding to template and the sequential release of the extended primers from the template have to be carried out at separate distinct temperatures and require a thermocycler to provide repeated sequences of distinct thermal steps. The existence of discrete cycles with different conditions also necessitates an optimization of temperature for each individual temperature step as well as an appropriate timing for each step. Similar problems also apply when ligation is used in the LCR reaction (Backman, K. et al. European Patent Publication No. 0 320 308 B1, Landegren, U., et al., 1988 Science 241; 1077, Wu, D. and Wallace, R. B. 1989 Genomics 4; 560, Barany, F. 1991 Proc, Nat. Acad. Sci. USA 88; 189) where the temperature required for binding individual probes is less than the temperature required to release them after they have been stabilized by a ligation event. All of the foregoing documents are incorporated herein by reference.

Others have recognized these limitations and tried to overcome them by providing means to accomplish multiple cycles under isothermal conditions. Examples of this are 3SR (Kwoh, D. Y. et al., (1989) Proc. Nat. Acad. Sci. USA 86; 1173-1177) and NASBA (Kievits, T. et al., 1991 J. Virol. Methods 35; 273-286, the contents of each of which is incorporated herein by reference). Each of the preceding systems has the limitation of a necessity for the introduction of an RNA promoter into the structure of the nucleic acid being amplified. Consequently, there is also a limitation that these systems are dependent upon a cycling reaction between DNA and RNA forms of the sequence of interest. A dependency upon the production of an RNA intermediate introduces a limitation of susceptibility to RNases, enzymes that are ubiquitous in the environment and are frequently present in biologically derived specimens. In addition, the nature of the design of these amplification systems has the further limitation that they require the presence of four distinct enzymatic activities: DNA polymerase, Reverse Transcriptase, RNase H and RNA polymerase. In the TMA reaction, these activities are provided by the Reverse Transcriptase and RNA polymerase enzyme whereas in 3SR and NASBA they are provided by Reverse Transcriptase, RNase H and RNA polymerase enzymes. Each of these activities is required for the system to be functional, and as such there is a necessity for the manufacturer to test and titrate each function individually, thereby increasing the cost compared to systems that utilize a single enzyme activity. In addition, at a minimum, at least two different enzymes have to be used to provide all the necessary functions, thus rendering these systems more expensive than those that utilize a single enzyme. Furthermore, these systems require ribonucleotides as well as deoxyribonucleotides to be present as reagents for the reactions. The presence of multiple activities also creates more steps that are vulnerable to being inactivated by various inhibitors that may be present in biological specimens.

In the Strand Displacement Amplification method described by Walker et al. (Proc. Nat. Acad. Sci. U.S.A. 1992, 89; 392-396, incorporated herein by reference), isothermal amplification is carried out by the inclusion of a restriction enzyme site within primers such that digestion by a restriction enzyme allows a series of priming, extension and displacement reactions from a given template at a single temperature. However, their system has the limitation that besides the basic requirement for a polymerase and substrates, three additional elements are required in order to carry out their invention. First, there is a necessity for the presence of appropriate restriction enzyme sites at the sites where priming is to take place; secondly, there is a necessity for a second enzyme, a restriction enzyme, to be present, and lastly there is a necessity for specially modified substrates, such as thio derivatives of dNTPs to be present. A variation of this method has been described (U.S. Pat. No. 5,270,184, incorporated herein by reference) where the limitation of a necessity of a restriction enzyme site in the target has been eliminated by the use of a second set of primers that are adjacent to the primers with the restriction enzyme sites. However, in this variation, a system is described that has a new limitation of a requirement for a second set of primers while retaining the other two limitations of a need for a restriction enzyme and modified substrates.

Temperatures used for the various steps of full cycle amplification are dictated by the physical constraints that are intrinsic to each step. As such, in prior art the temperature used for complete displacement of extended strands from templates is typically around 92-95° C. This high temperature has been used to insure an adequate efficiency of separation such that an extended strand can be used as a template for subsequent reactions. When PCR was first described, the polymerase was derived from E. coli and as such there was essentially complete thermal inactivation of the polymerase after each denaturation step that required the addition of more enzyme (Saiki et al., 1985 230; 1350-1354; cited supra). This problem was addressed by the use of a DNA polymerase from a thermophilic bacterium, T. aquaticus, in PCR reactions (Saiki et al., 1988 Science 239; 487-491). Each of the foregoing Saiki publications is incorporated herein by reference. Due to its inherent heat stability, enzyme was continuously present throughout the PCR cycles and no further additions were required. Since that time, polymerases from other thermophiles have also been isolated and used in full cycle reactions. However, even though they are more robust in their resistance to thermal inactivation, these polymerases all suffer from a limitation of having a certain level of inactivation after each denaturation step that is dictated by a half-life for that particular enzyme at the temperature used for denaturation. Also the high denaturation temperature can also decrease the levels of dNTP substrates by hydrolysis and lead to inactivation of proteins that may be added to supplement the efficiency or specificity of the reaction.

Full cycle PCR conditions have been modified such that lower denaturation temperatures could be used Auer et al., (1996, Nucl. Acids Res 24; 5021-5025, incorporated herein by reference) have described a procedure that used dITP, a natural neutral analogue of dGTP. By this substitution, they succeeded in avoiding amplification of double-stranded DNA that may be present in their samples and only amplified RNA targets. By no means is there recognition or appreciation of a utility for DNA targets. In fact, they teach away since their purpose is to avoid the use of DNA targets as templates. Their teachings have a limitation that the substitution dITP also necessitated a compensatory decrease in the temperatures used for the annealing (50° C.). In addition, the art described by Auer et al. relies upon the use of a nucleotide analogue that is known for a lack of discrimination for base pairing, thereby introducing the possibility of random variations being introduced into the sequence being amplified. When these alterations are in the primer binding area they may cause problems in priming efficiency and when they are in sequences between the primers they may introduce difficulties in detection probes being able to bind efficiently. The present invention is capable of using bases that exhibit normal levels of base pairing discrimination thereby avoiding the mutagenic events that are part of the previous art.

Determination of the nucleic acid sequence of genes and genomes is a major activity in both commercial and non-profit laboratories. The two basic systems that have been employed for this purpose are the base specific cleavage method described by Maxam and Gilbert (Proc. Nat. Acad. Sci. U.S.A. 1977, 74, 560-564) and the dideoxy method described by Sanger et al. (Proc. Nat. Acad. Sci. U.S.A. 1977, 74, 5463-5467). Both of the foregoing classical papers are incorporated herein by reference. Due to its ease of use the latter method is more commonly used. Both of these methods initially relied upon radioactive substrates for obtaining sequence information. For Maxam and Gilbert sequencing, this was most commonly carried out by end-labeling each strand and then separating each labeled end. For Sanger sequencing, either the primer is labeled or radioactive dNTP's are incorporated during strand extension. Sequence data was produced by autoradiographic determination of the position of radioactively labeled DNA bands of various lengths that had been separated by electrophoresis through a polyacrylamide gel.

In more recent years, sequencing methods have been improved by the substitution of non-radioactive labels. Non-radioactive labeling, potential positions for these labels and applications of their use are disclosed by Engelhardt et al., in U.S. Pat. No. 5,241,060, which was originally filed in 1982. Such labels can be in the oligo primer or in the substrates used for synthesis, i.e. the dNTP or ddNTP nucleotides. Signal generating moieties can act directly as exemplified by the use of fluorescently labeled primers (Beck et al., Nucleic Acids Res. 1989, 17; 5115-5123) or indirectly as exemplified by the use of biotin labeled primers (Ansorge et al., J. Biochem. Biophys. Methods 1986, 13; 315-323 and). In addition, biotinylated nucleotides could be incorporated during limited primer extension (Sequenase Images™ Protocol Book 1993 United States Biochemical Corporation, Cleveland, Ohio). The foregoing four documents are incorporated herein by reference. A limited extension is required to standardize the amount of band-shifting caused by the modification in the nucleotides.

However, primer labeling has the limitation that there can be secondary structure or problematic sequences in the template strand that can cause inappropriate chain termination events that create ambiguities in the proper base assignment for that position. Incorporation of labeled dNTPs during the extension of the primer also suffers from this limitation. This limitation is valid regardless of whether radioactive or non-radioactive labels are used.

This limitation has been circumvented by the choice of the chain terminator nucleotide itself as the source of the label. This has been described by Hobbs and Cocuzza in U.S. Pat. No. 5,047,519 and by Middendorf et al., in U.S. Pat. No. 4,729,947 for fluorescently labeled ddNTPs and by Middendorf et al., in U.S. Pat. No. 4,729,947 for biotin labeled ddNTPs that were later marked by fluorescent avidin. (For further reference refer to U.S. Pat. Nos. 5,027,880; 5,346,603; 5,230,781; 5,360,523; and 5,171,534.) Each of the foregoing seven patents are incorporated by reference into this application. By this method, signals will be generated by strands that have incorporated a chain terminator. The presence of strands that have been terminated without the incorporation of a terminator nucleotide is now irrelevant since they are incapable of signal generation. However, this method has the limitation that the presence of additional chemical groups that provide signal generation produce steric or other inhibitory problems for the polymerase directed incorporation of the labeled terminator nucleotide, thereby decreasing the efficiency of the reaction (Prober et al. in U.S. Pat. No. 5,332,666, incorporated herein). It has also been suggested that biotinylated dideoxynucleotides could be used to provide signal generation, but these modified terminators were predicted to share the same limitations as their fluoresceinated counterparts, i.e. difficulty in incorporation by most commonly used polymerases (S. Beck 1990 Methods in Enzymology 184; 612-617, also incorporated herein). Some compensation for this inefficiency of incorporation can be achieved by increasing the amounts of polymerase in the reaction and/or by increasing the amounts of template DNA being copied. These compensatory steps suffer the limitation of increased costs associated with higher amounts of an expensive enzyme, DNA polymerase, or with preparation of adequate amounts of high quality template

SUMMARY OF THE INVENTION

This invention provides for novel processes that are useful and applicable in nucleic acid amplification, nucleic acid sequencing and the production of unique nucleic acids having important properties, such as decreased thermodynamic stability.

The present invention provides a process for linearly amplifying a specific nucleic acid sequence. Initially, there are provided the specific nucleic acid sequence of interest that is sought to be amplified, an initial primer or a nucleic acid construct comprising two segments. The first segment (A) is unique, being characterized as (i) substantially complementary to a first portion of the specific nucleic acid sequence and (ii) capable of template-dependent first extension. The second segment (B) is uniquely characterized in the following four respects. First, it is (i) substantially non-identical to the first segment. Second, it is (ii) substantially identical to a second portion of the specific nucleic acid sequence. Third, the second segment (B) is (iii) capable of binding to a complementary sequence of the second segment. Fourth, the second segment (B) is (iv) capable of providing for subsequent binding of a first segment of a second primer or nucleic acid construct to the first portion of the specific nucleic acid sequence under isostatic or limited cycling conditions. In this way, a second primer extension is produced and displaces a first primer extension. Also provided in this process are substrates, buffer and a template-dependent polymerizing enzyme. In carrying out this amplification process, the specific nucleic acid sequence and the novel primer or nucleic acid construct are incubated in the presence of the substrates, buffer and template-dependent polymerizing enzyme under isostatic or limited cycling conditions; thereby linearly amplifying said specific nucleic acid sequence.

The present invention also provides a process for non-linearly amplifying a specific nucleic acid sequence. In this process, there are provided the specific nucleic acid sequence of interest sought to be amplified, a first initial primer or a nucleic acid construct for the specific nucleic acid sequence of interest, a subsequent initial primer or a nucleic acid construct to the complement of the specific nucleic acid sequence of interest, and substrates, buffer and a template-dependent polymerizing enzyme. The first initial primer or nucleic acid construct comprises two segments. The first segment (A) is unique, characterized as being (i) substantially complementary to a first portion of the specific nucleic acid sequence and (ii) capable of template-dependent first extension. The second segment is also unique, being characterized with four features. First, it is (i) substantially non-identical to the first segment. Second, it is (ii) substantially identical to a second portion of the specific nucleic acid sequence. Third, the second segment is (iii) capable of binding to a complementary sequence of the second segment. Fourth, the second segment is (iv) capable of providing for subsequent binding of a first segment of a second primer or nucleic acid construct to the first portion of the specific nucleic acid sequence under isostatic or limited cycling conditions. In this way, a second primer extension is produced to displace a first primer extension. The subsequent initial primer or a nucleic acid construct to the complement of said specific nucleic acid sequence also comprises two segments. The first segment (A) is characterized as (i) being substantially complementary to a first portion of the specific nucleic acid sequence and (ii) capable of template-dependent first extension. The second segment (B) is uniquely characterized with four features. First, the second segment (B) (i) substantially non-identical to the first segment. Second, it is (ii) substantially identical to a second portion of the specific nucleic acid sequence, Third, the second segment (B) is (iii) capable of binding to a complementary sequence of the second segment. Fourth, it is (iv) capable of providing for subsequent binding of a first segment of a subsequent primer to the first portion of the specific nucleic acid sequence under isostatic or limited cycling conditions. Under such conditions and in this way, a second primer extension is produced which displaces a first primer extension. To carry out this process, the specific nucleic acid sequence and the novel primer or nucleic acid construct are incubated in the presence of the substrates, buffer and template-dependent polymerizing enzyme under isostatic or limited cycling conditions; thereby non-linearly amplifying the specific nucleic acid sequence of interest.

Also provided by this invention is a process for non-linearly amplifying a specific nucleic acid sequence. In this non-linear amplification process, there are provided the specific nucleic acid sequence of interest sought to be amplified and its complement. Also provided is a first initial primer or a nucleic acid construct for the specific nucleic acid sequence, this first initial primer or nucleic acid construct comprising two segments. The first segment (A) has two useful and novel features. First, it is (i) substantially complementary to a first portion of the specific nucleic acid sequence. Second, the first segment is (ii) capable of template-dependent first extension. The second segment (B) has four useful and novel features. First, it is (i) substantially non-identical to the first segment. Second, the second segment (B) is (ii) substantially identical to a second portion of the specific nucleic acid sequence. Third, it is (iii) capable of binding to a complementary sequence of the second segment. Fourth, the second segment (B) is (iv) capable of providing for subsequent binding of a first segment of a subsequent first primer to the first portion of the specific nucleic acid sequence under isostatic or limited cycling conditions. Under such conditions and in this way, a second primer extension is produced which displaces the first primer extension. Also provided in this process is a second initial primer or a nucleic acid construct complementary to the first primer extension;. The second initial primer or nucleic acid construct typically comprises a single segment characterized by its being capable of template-dependent extension under isostatic or limited cycling conditions. Appropriate substrates, buffer and a template-dependent polymerizing enzyme are also provided. To carry out this process of the present invention the specific nucleic acid sequence and the novel primer or nucleic acid construct are incubated in the presence of the appropriate substrates, buffer and template-dependent polymerizing enzyme under isostatic or limited cycling conditions. Under such incubation carried out under those conditions, the specific nucleic acid sequence of interest is amplified non-linearly.

This invention further provides a process for non-linearly amplifying a specific nucleic acid sequence of interest sought to be amplified. In this novel process, there are provided the specific nucleic acid sequence of interest, a singular primer or a singular nucleic acid construct capable of non-linear amplification and comprising three segments. There is a first segment (a) that is (i) substantially complementary to a first portion of the specific nucleic acid sequence and is (ii) capable of template-dependent first extension. A second segment (b) is substantially identical to a second portion of the specific nucleic acid sequence. The third segment (c) is substantially identical to the first segment. The first primer extension is capable of producing sequences that are capable of hybridizing to said second segment and is also capable of self-priming and self-extending to produce a complement to the third segment. Also provided are appropriate substrates, buffer and a template-dependent polymerizing enzyme. In carrying out this amplifying process, the specific nucleic acid sequence and the primer or nucleic acid construct are incubated together in the presence of the appropriate substrates, buffer and template-dependent polymerizing enzyme. The specific nucleic acid sequence of interest is non-linearly amplified thereby.

Also provided by the invention at hand is a post-termination labeling process for nucleic acid sequencing. Here, the process comprises the first step of producing, in the presence of untagged or unlabeled substrates, untagged or unlabeled primer, polymerizing enzyme, buffer and an appropriate untagged or unlabeled terminator for each nucleotide base, nucleic acid fragments corresponding to the nucleic acid sequence of interest whose sequence is sought In this process, each of the terminators comprise a chemically reactive group that covalently binds to a tagged molecule under conditions such that the internal sequences are substantially non-reactive to the tagged molecules and the chemical reactions do not substantially interfere with the separation of the fragments in a medium or matrix. After the production of fragments, the latter are separated in a medium or matrix, followed by detection of the separated fragments achieved by the detection of the tagged molecule in the medium or matrix.

Another process provided by the present invention is a process for producing nucleic acid sequences that have decreased thermodynamic stability to complementary sequences. In this process, at least one modified nucleotide or nucleotide analog having a negatively charged chemical moiety is incorporated into nucleic acid sequences which are produced.

In addition to other aspects of this invention, there is provided a single-stranded or double-stranded nucleic acid polymer selected from the group consisting of a linear nucleic acid, branched nucleic acid, an inverted nucleic acid and a peptide-nucleic acid, or a combination of any of the foregoing. This nucleic acid polymer comprises at least one purine or pyrimidine base comprising one negatively charged chemical moiety in one or both strands of the polymer.

All of these processes and polymers are described in greater detail below.

BRIEF DESCRIPTION OF THE FIGURES

FIG. 3 depicts a series of reactions that can be carried out by a nucleic acid construct with two 3' ends where part of the construct is capable of hairpin formation after template dependent extension.
FIG. 4 is a continuation of the process and events shown in FIG. 3.
FIG. 13 depict illustrations of another design for a novel nucleic acid construct with two 3' ends that is capable of non-linear amplification.
FIG. 15 depict illustrations of another design for a novel nucleic acid construct with two 3' ends that is capable of non-linear amplification.
FIG. 17 shows gel assays of isothermal amplifications of a target created by PCR.
FIG. 20 summarizes the results of FIG. 19.
FIG. 26 shows the sequences for the template and primers used for PCR synthesis in the presence of carboxy dUTP.
FIG. 29 are the results of gel assays for various conditions used for post-synthetic attachment of a fluorescent marker.
FIG. 30 is a negative image of the results of FIG. 29.

Figure 1:
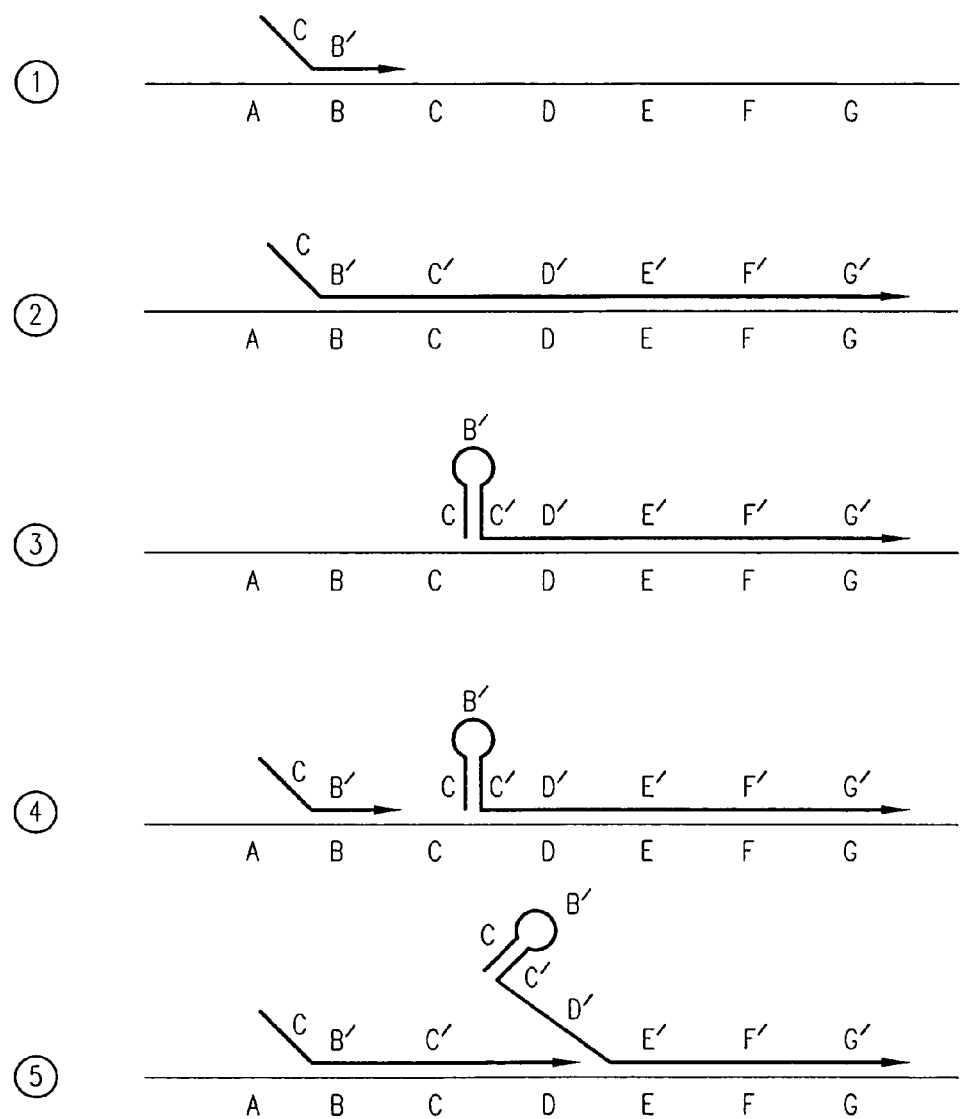
FIG. 1 depicts linear amplification by a novel primer.

The definitions below are useful to an understanding of the present invention and this disclosure.

Definitions

Isostatic conditions refer to substantially constant temperature and/or chemical conditions.

Limited cycle conditions refer to a series of temperatures where the highest temperature used is below the temperature required for separation of an extended primer from its template.

Full cycle conditions refer to a series of temperatures where at least one temperature is used that is sufficient for separation of an extended primer from its template.

Linear amplification is carried out when two or more copies of only one strand of nucleic acid are produced.

Non-linear amplification is carried out when two or more copies of a nucleic acid sequence are produced from each strand of a nucleic acid and its complement.

An initial primer is a primer or primer construct that has not been extended.

A standard primer is a primer that is not substantially involved in secondary structure formation with sequences synthesized after extension.

Extended sequences are sequences synthesized in a template dependent manner which are substantially neither identical or complementary to any sequences in primers or primer constructs.

A segment of a nucleic acid is substantially identical to another segment when the complement of the said other segment is capable of acting as a template for extension of the said first segment.

DETAILED DESCRIPTION OF THE INVENTION

The present invention provides, compositions and methods of use for novel primers and nucleic acid constructs that a) contain at least one segment that has self-complementary sequences or is capable of forming a secondary structure after template-dependent extension and b) are capable of producing two or more copies of a specific nucleic acid sequence under appropriate conditions in the presence of an appropriate specific template under appropriate conditions.

All methods of target amplification that use primer binding and extension reactions for synthesis of a specific nucleic acid sequence have the necessity to regenerate a binding site or sites or to synthesize a new primer binding site or sites if two or more copies of this sequence are desired. In all methods of art that have been previously described, outside modulating factors have been used to regenerate or create primer binding sites. These factors have included thermal denaturation as exemplified by PCR, endonucleases as exemplified by 3SR, and restriction enzymes and modified nucleotides as exemplified by SDA.

In certain aspects of the present invention, novel primers and nucleic acid constructs are disclosed that have as an inherent characteristic that at least one segment of a novel primer or nucleic acid construct is capable of secondary structure formation under appropriate conditions. In the present invention, the formation of a secondary structure can provide for regeneration of binding sites such that they can be used for multiple binding and extension of novel primers or nucleic acid constructs without the necessity for any of the outside modulating factors described above.

In previous art there has been a necessity for the presence of a primer binding site in each complementary strand of a target nucleic acid in order to achieve non-linear amplification. In certain aspects of the present invention, the formation of secondary structures overcomes this limitation such that a single primer can be used that is complementary to only one nucleic acid strand and not the other, but yet is still capable of carrying out non-linear amplification of a desirable nucleic acid sequences.

The novel primer and nucleic acid constructs of the present invention are capable of use in linear and non-linear amplification systems that require only a single primer or more than one primer under isostatic, limited cycle or full cycle conditions. The capability for formation of secondary structures is due to the presence of self-complementary sequences in a novel primer or nucleic acid construct or it may be derived from the template dependent incorporation of sequences that are complementary to a segment of the novel primer or nucleic acid construct. It may also be derived from both pre-existing and post-synthesis sequences. The novel primer and nucleic acid constructs of the present invention can be linear molecules with a single polarity, constructs with more than one polarity or branched nucleic acids. Methods of synthesis and examples of use of such constructs have previously been disclosed in (U.S. patent application Ser. No. 08/749,266; U.S. Pat. No. 5,462,854, both documents incorporated herein). In certain aspects of the present invention, the novel primer and nucleic acid constructs comprise at least two segments: a first segment that is capable of binding to a template and using it for extension and a second segment that is substantially identical to sequences of the target of interest such that extension of the first segment allows formation of a secondary structure formed by self-hybridization of the second segment with the extended sequences. In certain aspects of the present invention, the novel primer and nucleic acid constructs comprise at least three segments: the first and second segments being defined as above and a third segment which is capable of acting as an intrastrand or intraconstruct template for self-extension.

Segments can be joined together either covalently or non-covalently. Means of joining segments through covalent linkages can include but are not limited to the phosphate backbone of normal linear nucleic acids, constructs that have more than one polarity and branched DNA constructs. Methods for synthesizing these constructs have been described in U.S. patent application Ser. No. 08/749,266, filed on Nov. 15, 1996, contents of which are incorporated herein. Means of joining segments by non-covalent linkages can include but are not limited to ligand-receptor bonds and complementary base pairing. The segments may be adjacent to each other or they may be spatially separate from each other. The sequences of the segments may be distinct from each other or they may be substantially or partially complementary or identical to each other.

The formation of useful secondary structures can be augmented by additional elements in the design of the novel primers and nucleic acid constructs of the present invention. For instance, secondary structures can be introduced into the sequences of the novel primers of the present invention that can allow extension-dependent secondary structures to form more easily. Supplementary elements can also be included in the reaction mixture to favor the formation of appropriate secondary structures. These elements can include but are not limited to proteins such as single-stranded binding protein, the T4 gene 32 protein, Rec A protein and various helicases. These elements can also include but are not limited to chemical reagents such as Formamide or DMSO. These elements can also include but are not limited to modified nucleotides that either raise or lower the Tm of a nucleic acid sequence. The modified nucleotides can pre-exist in the novel primers and nucleic acids constructs, they can be incorporated during the extension reactions or they can be both.

The various novel primers and novel nucleic acid constructs of the present invention overcome many of the limitations of previous systems. In contrast to methods that have been previously described in the art that depend upon the use of a thermocycler, certain aspects of the present invention have no necessity for a strand separation event prior to a new priming event. Additionally, the present invention has no requirements for multiple enzyme arrangements, ribonucleotides or the presence of a promoter sequence as are intrinsic to isothermal systems that are dependent on the generation of an RNA intermediate such as 3SR, NASBA and TMA. Nor is there a requirement for esoteric modified reagents and a supplementary restriction enzyme as has been described for the isothermal SDA system.

Also included in the present invention are novel methods and compositions that can be used for labeling of nucleic acids. These can be used in conjunction with various aspects of the present invention or may be used in conjunction with methods described in previous art.

This invention provides for a process to amplify linearly a specific nucleic acid sequence of interest that one seeks to amplify. Such a process includes the step of providing the following components and reagents: the specific nucleic acid sequence of interest, an initial primer or a nucleic acid construct comprising two segments, and appropriate substrates, buffer and a template-dependent polymerizing enzyme. The two segments of the initial primer or nucleic acid construct include (A) a first segment having two defined characteristics. First, it is (i) substantially complementary to a first portion of the specific nucleic acid sequence and second, it is (ii) capable of template-dependent first extension. The second segment (B) has four defined characteristics. First, the second segment (B) is (i) substantially non-identical to the first segment. Next, it is (ii) substantially identical to a second portion of the specific nucleic acid sequence. Third, the second segment (B) is (iii) capable of binding to a complementary sequence of the second segment. Fourth, this second segment is (iv) capable of providing for subsequent binding of a first segment of a second primer or nucleic acid construct to the first portion of the specific nucleic acid sequence under isostatic or limited cycling conditions. In so doing, a second primer extension is produced and that displaces a first primer extension. Another important step of this linear amplification process is that of incubating the specific nucleic acid sequence and the novel primer or nucleic acid construct in the presence of the appropriate substrates, buffer and template-dependent polymerizing enzyme under isostatic or limited cycling conditions; thereby linearly amplifying the specific nucleic acid sequence of interest that one seeks to amplify.

In other aspects of the just-described process, the initial primer or nucleic acid construct and the second primer or nucleic acid construct can be the same, or they can be different. Furthermore, at least one modified nucleotide or nucleotide analog can be usefully incorporated into various components or elements of the process, including the first segment, the second segment, or the primer extension product, or any of the foregoing elements for that matter. Such a modified nucleotide or nucleotide analog can be usefully incorporated into the second segment defined above. When usefully incorporated into the second segment, such a modified nucleotide or nucleotide analog increases the thermodynamic stability of the first segment to its complement in the primer extension. The modified nucleotide or nucleotide analog can comprise an intercalating agent, for example.

Those skilled in the art will appreciate that the first segment or the primer extension product, both of these elements, can comprise at least one modified nucleotide or nucleotide analog. In such instances, the modified nucleotide or nucleotide analog decreases the thermodynamic stability of the first segment or the primer extension product to its complement. Such thermodynamic stability decreasing modified nucleotides or nucleotide analogs comprise, for example, a negatively charged chemical group, such as a carboxylic acid.

With respect to the nucleic acid form, the initial primer or nucleic acid construct or the second primer or nucleic acid construct (or both primers and nucleic acid constructs), can comprise a number of nucleic acids. These include but are not limited to linear nucleic acid, branched nucleic acid, an inverted nucleic acid and a peptide-nucleic acid, or a combination of any of the preceding. Further description of linear amplification follows immediately below.

Linear Amplification with One Stem-Loop Forming Primer

In one aspect of the present invention, linear amplification of a specific nucleic acid sequence is carried out under isostatic or limited cycle conditions by the use of a single novel primer or a single novel nucleic acid construct that has at least two segments. The novel nucleic acid constructs of the present invention can have more than one polarity or they can be branched DNA. Methods for synthesizing these constructs have been described in U.S. patent application Ser. No. 08/749,266, cited supra and incorporated herein. The first segment of a novel primer or nucleic acid construct comprises sequences that are substantially complementary to sequences that are present in a target nucleic acid sequence. The second segment of a novel primer or nucleic acid construct comprises sequences that are substantially identical to sequences that are present in the target nucleic acid. A novel nucleic acid construct can have one or more copies of the first and second segments. Template dependent extension of the novel primer or nucleic acid construct can create a product that has a stem-loop structure formed by self-hybridization as well as extended sequences that are not identical to or complementary to sequences that comprise the novel primer or nucleic acid construct.

This product can be formed by a continuous series of the following steps that are illustrated in FIG. 1. Template dependent extension of a novel primer or nucleic acid construct produces in the extended portion sequences that are complementary to sequences that comprise the second segment of the said novel primer or nucleic acid construct. These self-complementary regions can remain bound to the template or can form self-complementary structures. The formation of a secondary structure can provide for removal of all or part of the first segment of the extended novel primer from the template. This would allow another initial primer to bind to template sequences prior to removal of the first extended novel primer from the template. Extension of the second primer on the template can lead to displacement of the first extended primer from the template. This is in contrast to previous art where separation of an extended primer always takes place prior to use of the template for another binding and extension reaction. By these means, a single template can provide for two or more initiation events under isostatic conditions. In addition, this method can be used under limited cycling conditions where all temperatures are below those of the Tm of an extended product and its template. In a continuing process, formation of a secondary structure in the second extended novel primer can provide for binding and subsequent extension of a third novel primer. In this way, in the absence of denaturing conditions, the novel process of the present invention can provide for multiple priming, extension and release events from a single strand of a nucleic acid template. Furthermore, all of these steps can take place simultaneously and continuously under isostatic conditions.

A novel nucleic acid construct with multiple identical first and second segments could also be used to carry out linear amplification by the same processes that have been depicted in FIG. 1. This novel construct could potentially enjoy an increase in efficiency compared to a linear construct with single polarity. The binding and extension of one of the first segments of a construct molecule results in a localized high concentration of other first segments of the construct that can bind to the regenerated primer binding site. After multiple priming and extension reactions, a construct can be created that comprises multiple copies of a single strand of target DNA.

The ability of extended novel primer and nucleic acid constructs to form self-complementary structures can be realized under appropriate conditions. Previous art has indicated that the association and dissociation of short complementary oligonucleotides occurs as an equilibrium reaction whose characteristics are determined by the temperature, salt conditions, base content and length of the complementary sequences. The influence of these factors has been reviewed by J. G. Wetmur ([1991] Crit. Rev. Biochem. Mol. Biol. 26; 227-259, incorporated herein). Although larger strands of complementary DNA exist as double-stranded molecules in stable configurations that do not readily dissociate over a wide range of conditions, it is well known that they do form temporary and localized relaxations of interstrand bonding. The term "breathing" has been used to describe this localized disruption of hydrogen bonding. A pathway for "breathing" to create two-dimensional structures in double-stranded DNA molecules that contain palindromic sequences has been described by A. Kornberg and T. A. Baker in "DNA Replication, $2^{nd}$ Edition" (1992) W. H. Freeman and Co. NY, N.Y., pages 44-46; the contents of which are incorporated herein by reference.

In the present invention, as described above, the transition of a segment of a linear double-stranded molecule to an intra-strand stem-loop structure can allow primer initiation events to take place prior to separation of an extended primer from its template. The equilibrium between these two structures is dependent upon a number of factors. First, for successful primer binding, the segment of the initial primer that binds to the target must be of appropriate length and base composition so as to allow stable priming at the temperature being used for the reaction. Second, the segment of the primer that participates in self-hybridization after an extension of the initial primer must be of appropriate length and base composition such that a partial dissociation of the extended primer from the template can allow the formation of a sufficiently stable secondary structure, i.e., the stem of a stem-loop structure.

Temperatures appropriate for these reactions are below those that would be required for separation of an extended primer from its template. In an isostatic reaction, a single temperature can be used for binding, extension and secondary structure formation. Or if so desired, limited cycling conditions can be used where different temperatures are used to optimize these events. The use of different temperatures for limited cycling may be useful for primer binding, primer extension or a localized separation of some of an extended product from its template. The temperatures being used for any and all of these steps should also be appropriate for the particular polymerase being used in the reactions.

Intra-molecular complementary regions in an extended primer have been utilized previously by Rose et al. (U.S. Pat. Nos. 5,595,891, 5,612,199, both incorporated herein) to provide identical binding sites on each strand of a target nucleic acid in order to allow the use of a single primer for PCR amplification. However, all examples and teachings provided by Rose et al. require heating steps to separate an extended primer from its template prior to use of the template for the next primer binding and extension events, i.e. multiple cycles of complete denaturation in a thermocycler. Studies with single-stranded RNA have shown that as the size of the loop increases there is a diminished chance for intra-strand stem formation (R. L P. Adams et al., in "The Biochemistry of the Nucleic Acids" [1992] Chapman & Hall, London, U.K., incorporated herein). Yet, the methods provided by Rose et al. for PCR amplification with either natural or artificially introduced inverted repeat sequences as primer sites utilize a preferred separation of 100-2,000 nucleotides and more preferably of 500-10,000 bases between complementary sequences that form the stem of a stem-loop structure. Such a direction teaches away from the methods and compositions disclosed in the present invention where complementary sequences are sufficiently proximate to each other that formation of a stem-loop structure could facilitate the removal or partial removal of the first segment of an extended primer from its template to regenerate a binding site without the necessity of imposition of conditions that would provide for the complete separation of an extended primer from its template. In addition, the teachings provided by Rose et al. preclude the use of self-complementarity in the primer as a means of allowing amplification under isothermal or limited cycle conditions since their operating range would make secondary structure formation energetically unfavorable under isothermal or limited cycle conditions. The gain in energy created by formation of a stable stem structure is compromised and outweighed by the energy cost of displacing a long strand from its complement to form the loop portion of a stem-loop structure. Thus full cycle conditions are required to regenerate a primer binding site. The consequences of the teachings and processes of Rose et al. lead to products in which the extended sequences are always in the loop of a stem-loop structure whereas in this aspect of the present invention, the product of the novel primers and processes have the extended sequences essentially outside of potential stem-loop structures.

The aspect of the invention that has been described above finds particular utility in the preparation of labeled single-stranded DNA probes and for determining the sequences of nucleic acids. Prior to the disclosure of the present invention, the most commonly used methods for obtaining single-stranded DNA probes have been dependent upon multiple strand denaturation events provided by a thermocycler, or by the use of RNA polymerase with templates that contain an RNA promoter. Processes that depend upon multiple strand denaturation events suffer from a limitation of loss of a certain amount of reagents and enzyme activity at the high temperatures required for denaturation of templates. Even thermostable polymerases are not completely immune to the effects of denaturation condition temperatures and have various half-lives at these temperatures. Also the use of such conditions precludes the use of some enzymes that are completely inactivated by such temperatures. These processes also have the limitations of the need of a thermocycler. Processes that are dependent upon production of RNA suffer from the limitations associated with a need for introducing an RNA promoter into association with the sequences desired for a probe and from limitations that are intrinsic to a product that is more labile than DNA. The methods disclosed for the use of isostatic or limited cycle conditions in the present invention can be used with or without a thermocycler. They allow the use of a wider array of enzymes, reagents are not subjected to extreme destabilizing conditions and stable reusable DNA probes are the final product.

This aspect of the present invention can also be used in sequencing by allowing a template to be used a multiple number of times under isostatic or limited cycle conditions. Previous art has only been able to accomplish this by the use of multiple strand denaturation events in a thermocycler. The limitations cited previously for multiple strand denaturation events are also applicable to this use. In addition, there is an additional limitation that the high temperatures required for denaturation can contribute to heat-induced depurination or deamination events that can create sequence ambiguities. Application of the methods of the present invention for multiple rounds of sequencing from a template offers the advantages of independence from the necessity of a thermocycler, utility of a wider array of enzymes and moderation of thermal effects upon the integrity of templates and reagents.

The present invention also provides a process for non-linearly amplifying a specific nucleic acid sequence. Non-linear amplification comprises a first step of providing the following components or reagents: the specific nucleic acid sequence of interest sought to be amplified, a first initial primer or a nucleic acid construct for the specific nucleic acid sequence, a subsequent initial primer or a nucleic acid construct to the complement of said specific nucleic acid sequence, and appropriate substrates, buffer and a template-dependent polymerizing enzyme. The just-described first initial primer or nucleic acid construct comprises two segments. First, there is a first segment (A) that has two defined characteristics. It is (i) substantially complementary to a first portion of said specific nucleic acid sequence and it is (ii) capable of template-dependent first extension. The second segment of the first initial primer has four defined characteristics. First, it is (i) substantially non-identical to the first segment (A). Second, it is (ii) substantially identical to a second portion of the specific nucleic acid sequence. A third characteristic of the second segment is its capability (iii) for binding to a complementary sequence of the second segment. A fourth characteristic of the second segment is its (iv) capability for providing for subsequent binding of a first segment of a second primer or nucleic acid construct to the first portion of the specific nucleic acid sequence under isostatic or limited cycling conditions. Under such conditions, a second primer extension is produced to displace a first primer extension.

With respect to the subsequent initial primer or nucleic acid construct, this element comprises two segments, a first segment (A) and a second segment (B). The first segment (A) is (i) substantially complementary to a first portion of the specific nucleic acid sequence and it is (ii) capable of template-dependent first extension. Four characteristics define the second segment (B). First, the second segment (B) is (i) substantially non-identical to the first segment. Second, it is (ii) substantially identical to a second portion of the specific nucleic acid sequence. Third, the second segment (B) is (iii) capable of binding to a complementary sequence of the second segment. The fourth characteristic of the second segment (B) is (iv) its capability for providing subsequent binding of a first segment of a subsequent primer to the first portion of the specific nucleic acid sequence under isostatic or limited cycling conditions. Under such conditions, a second primer extension is produced and that displaces a first primer extension. The second step of this process includes incubating the specific nucleic acid sequence and the novel primer or nucleic acid construct in the presence of the appropriate substrates, buffer and template-dependent polymerizing enzyme under isostatic or limited cycling conditions. The specific nucleic acid sequence of interest is thereby amplified non-linearly thereby.

In the just-described non-linear amplification process, the first initial primer or nucleic acid construct and the second initial primer or nucleic acid construct can be the same, or they can be different. Modified nucleotides or nucleotide analogs can be usefully incorporated as additional elements. For example, these can be incorporated into the first segment or the second segment of the first initial primer or nucleic acid construct, or into the first segment or the second segment of the second initial primer or nucleic acid construct. Or, modified nucleotides or nucleotide analogs can be incorporated into any primer extension products. For that matter, modified nucleotides or nucleotide analogs can be incorporated into or used to modify any of the preceding elements.

In further embodiments of this non-linear amplification process just-described above, the second segment of the first initial primer or the second initial primer can comprise a modified nucleotide or nucleotide analog which serves to increase the thermodynamic stability of the first segment to its complement in the primer extension product. Such modified nucleotides or nucleotide analogs comprise or take the form of, for example, an intercalating agent.

In other aspects of the process at hand, the first segment of the first initial primer or the first segment of the second initial primer (or both), or even the primer extension product (or any combination of the preceding elements, for that matter) can comprise a modified nucleotide or nucleotide analog. Here, the modified nucleotide or nucleotide analog serves to decrease the thermodynamic stability of the first segment or the primer extension or both, to their corresponding complement. Such stability decreasing modified nucleotides or nucleotide analogs can comprise negatively charged chemical groups, such as carboxylic acid.

Another aspect of the just-describe non-linear amplification process is the type or form of nucleic acid. Here, the first initial primer or nucleic acid construct, or the second initial primer or nucleic acid construct, or both, comprises any number or form of nucleic acids. Such members include but are not limited to linear nucleic acid, branched nucleic acid, an inverted nucleic acid and a peptide-nucleic acid, or combinations of any of the foregoing.

Another significant non-linear amplification process is provided by the present invention. This process amplifies non-linearly a specific nucleic sequence and comprise a first step of providing the following components and reagents: the specific nucleic acid sequence and its complement: a first initial primer or a nucleic acid construct for the specific nucleic acid sequence, a second initial primer or a nucleic acid construct complementary to said first primer extension, and appropriate substrates, buffer and a template-dependent polymerizing enzyme. The first initial primer or nucleic acid construct comprises two segments: a first segment (A) and a second segment (B). With respect to the former, two characteristics define it. First, it is (i) substantially complementary to a first portion of the specific nucleic acid sequence and second, it is (ii) capable of template-dependent first extension. With respect to the second segment (B), four characteristics define this element. First, it is (i) substantially non-identical to the first segment. Second, it is (ii) substantially identical to a second portion of the specific nucleic acid sequence. The third characteristic of the second segment (B) is its (iii) capability for binding to a complementary sequence of the second segment. A fourth characteristic of the second segment (B) is (iv) its capability for providing subsequent binding of a first segment of a subsequent first primer to the first portion of the specific nucleic acid sequence under isostatic or limited cycling conditions. Under such conditions, a second primer extension is produced and that displaces the first primer extension. The second initial primer or nucleic acid construct comprises a segment characterized by its capability for template-dependent extension under isostatic or limited cycling conditions. The important step of this process is, of course, that of incubating the specific nucleic acid sequence and the novel primer or nucleic acid construct in the presence of the appropriate substrates, buffer and template-dependent polymerizing enzyme under isostatic or limited cycling conditions. The specific nucleic acid sequence of interest is amplified non-linearly thereby.

Other aspects or features can be incorporated into the last-described process for non-linear amplification. One important feature is the inclusion of modified nucleotides or nucleotide analogs. For example, at least one modified nucleotide or nucleotide analog can be incorporated or used to modify any of the following member elements in the process: the first segment or the second segment of the first initial primer or nucleic acid construct, the segment of the second initial primer or nucleic acid construct, the primer extension, or any of the foregoing or combinations of any of the foregoing. Equally significant is the inclusion of at least one modified nucleotide or nucleotide analog into the second segment of the first initial primer. The inclusion of such modified nucleotides or nucleotide analogs serves to increase the thermodynamic stability of the first segment to its complement in the primer extension. Modified nucleotides or nucleotide analogs are well known in the art, and include, for example, intercalating agents.

Furthermore, the first segment of the first initial primer or the segment of the second initial primer (or both), or their primer extension (or for that matter, any combinations of the foregoing) can be modified or incorporated with at least one modified nucleotide or nucleotide analog. Such modified nucleotides or nucleotide analogs serve to decrease the thermodynamic stability of the first segment or the primer extension (or both) to their respective complements. Modified nucleotides or nucleotide analogs that serve to decrease stability can comprise a negatively charged chemical group, such as carboxylic acid.

As in the case of other processes for non-linear amplification described in this application, the form or type of nucleic acid can vary. The first initial primer or nucleic acid construct, or the second initial primer or nucleic acid construct, or both, can comprise nucleic acid selected from any of the following: linear nucleic acid, branched nucleic acid, inverted nucleic acid and peptide-nucleic acid (or combinations of any of the foregoing).

The invention at hand also provides another process for the non-linear amplification of a specific nucleic acid sequence of interest sought to be amplified. This process comprises the first step of providing the following components and reagents: the specific nucleic acid sequence of interest; a singular primer or a singular nucleic acid construct capable of non-linear amplification, and appropriate substrates, buffer and a template-dependent polymerizing enzyme. The singular primer or nucleic acid construct comprises three segments, (a), (b) and (c). The first segment (a) is (i) substantially complementary to a first portion of the specific nucleic acid sequence and (ii) is capable of template-dependent first extension. The second segment (b) is substantially identical to a second portion of the specific nucleic acid sequence. The third segment (c) is substantially identical to the first segment. The first primer extension is capable of producing sequences that are capable of hybridizing to the second segment and is also characterized by its capability for self-priming and self-extension to produce a complement to the third segment. Following the first step of this process, the specific nucleic acid sequence and the primer or nucleic acid construct are incubated in the presence of the appropriate substrates, buffer and template-dependent polymerizing enzyme. After incubation; the specific nucleic acid sequence is amplified non-linearly thereby.

Other embodiments for the last-described process for non-linear amplification are provided by the present invention. For example, the process can be carried out under conditions selected from isostatic conditions, limited cycling conditions and full cycling conditions.

In addition, modified nucleotides or nucleotide analogs can be used in the modification of various elements of the process. For example, any or all of the first segment, the second segment, the third segment, the first primer extension, the second primer extension, can include or comprise at least one modified nucleotide or nucleotide analog. Furthermore, modified nucleotides or nucleotide analogs can be incorporated into any or all of the first segment, the second segment, the third segment, the first primer extension and the self priming extension.

Those skilled in this art will also appreciate that the singular primer or nucleic acid construct can comprise a number of nucleic acid forms, including, for example, linear nucleic acid, branched nucleic acid, inverted nucleic acid and peptide-nucleic acid, or combinations of any of the foregoing. Skilled artisan will further appreciate that first primer extension can be carried out under various conditions, including for example, limited substrate conditions, limited extension duration, or both.

With respect to any of the processes described above for amplification of specific nucleic acid sequences of interest, be it linear or non-linear amplification, the specific nucleic acid sequence can be in single-stranded or double-stranded form. Moreover, the specific nucleic acid sequence can be found or is contained in a fragment. Such a fragment can be produced by a number of means, including physical means (sonication, heat, or both), chemical means (acid treatment), physico-chemical means and enzymatic means (nucleases, e.g., endo-nucleases, and restriction enzymes).

Non-linear amplification is further described below.

Non-Linear Amplification with Stem-loop Forming primers and Constructs

Non-linear amplification of a desired sequence can be carried out when binding sites on each strand are used by primers or nucleic acid constructs. In another aspect of the present invention, non-linear amplification can be carried out under isostatic or limited cycle conditions when at least one of the said primers or constructs is a novel primer or construct with a first and second segment. The novel nucleic acid constructs of the present invention can have more than one polarity or they could be branched DNA. Methods for synthesizing these constructs have been described in U.S. patent application Ser. No. 08/749,266, cited supra and incorporated herein. The first and second segments are as defined previously. The first segment of a novel primer or nucleic acid construct comprises sequences that are substantially complementary to sequences that are present in a target nucleic acid sequence. The second segment of a novel primer or nucleic acid construct comprises sequences that are substantially identical to sequences that are present in the target nucleic acid.

When primers are used for non-linear amplification, the binding site on one strand is used by a novel primer with a first and second segment and the binding site on the other strand may be used by either a standard primer or another novel primer. A single novel primer may be used by itself when the binding sites in each strand are substantially similar to each other. When constructs are used for non-linear amplification, the construct is a novel construct that comprises one or more first segments that are complementary to one strand and one or more first segments that are complementary to the other strand of the target nucleic acid. The construct also comprises one or more second segments that are identical to one strand and can also comprise one or more second segments that are identical to sequences in the other strand. The first segments of the novel construct may be substantially identical to each other or they may be substantially dissimilar to each other. The second segments of the novel construct may be substantially identical to each other or they may be substantially dissimilar to each other. It is also understood that combinations of standard primers, novel primers, constructs and novel constructs may also be used together as long as at least one of them contains a first and second segment.

As described previously, the binding and extension of a novel primer or nucleic acid construct can allow the use of a template for multiple primer binding and extension events under isostatic or limited cycle conditions. As new binding and extension events occur, they allow the separation of the nucleic acid strand that had previously been extended on that template. This results in the production of single-stranded nucleic acid strands that can be used as templates for binding of a second primer or nucleic acid construct without a necessity for a denaturation event since they are already in single-stranded form. When one primer is a standard primer and the other is a novel primer, the final product of template dependent bindings and extensions can be a double-stranded molecule that on one end comprises a stem-loop structure on each strand. When both primers are novel primers, the final product of template dependent bindings and extensions can be a double-stranded molecule that on each end comprises a stem-loop structure on each strand. When a construct comprises two first segments, each of which is complementary to one strand or the other and one second segment that is complementary to only one strand, the final product can be a single molecule that has complementary stem-loop structures. When a construct comprises two first segments, each of which is complementary to one strand or the other and two second segments, each of which is identical to one strand or the other, the final product can be a single molecule that has two pairs of complementary stem-loop structures.

Figure 2:
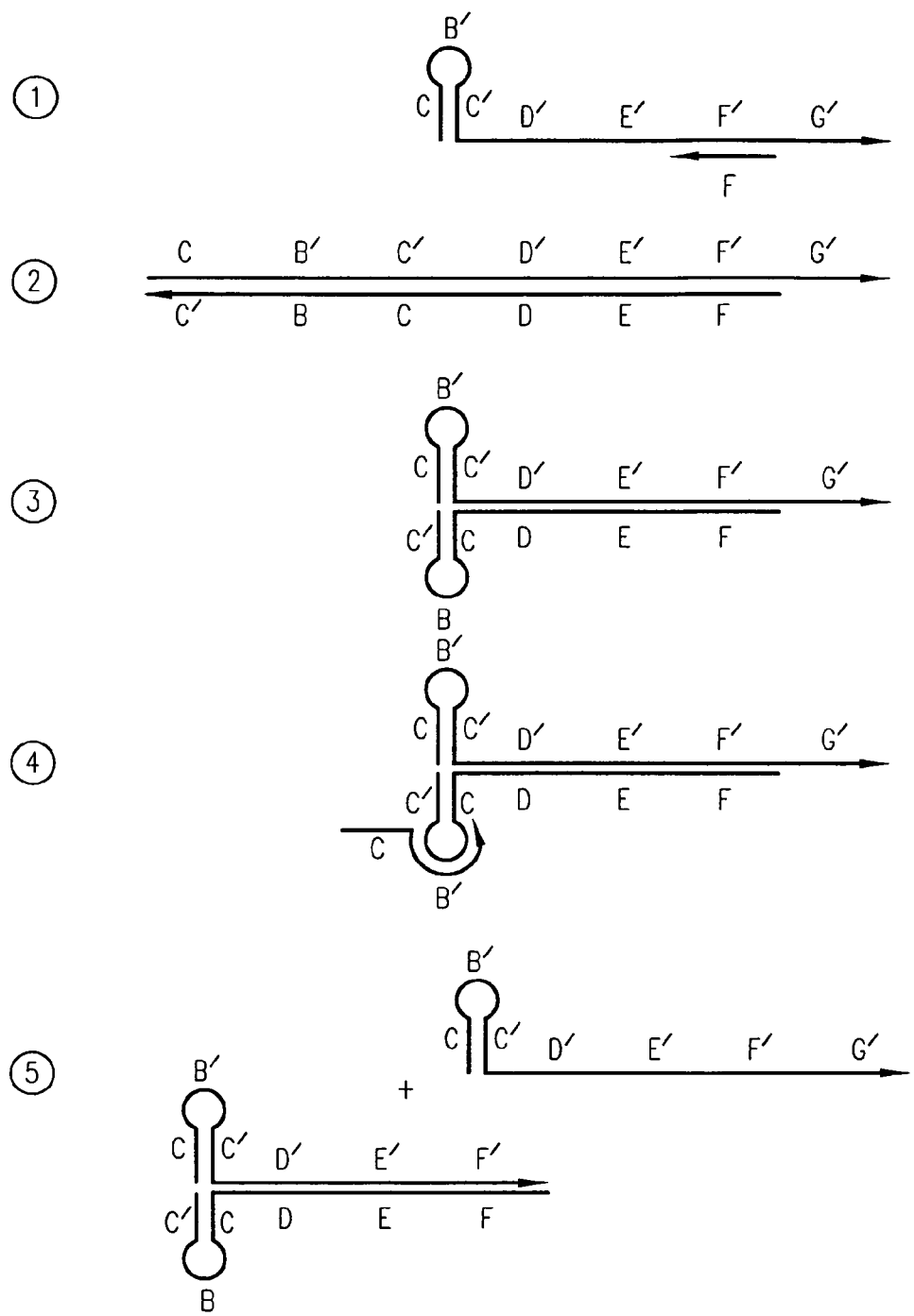
FIG. 2 depicts non-linear amplification by a novel primer and a standard primer.

A non-linear amplification product can be synthesized by a novel primer and a standard primer by a continuous series of the following steps under isostatic or limited cycle conditions. The novel primer binds to a target strand and there is the same series of extension, secondary structure formation, regeneration of a primer binding site, second binding, second extension and separation of the first extended primer from the template as described previously for linear amplification with a single novel primer. As extended novel primers are displaced by continuous binding and extension of other novel primers, these single-stranded products can bind standard primers and allow them to be extended to create a full double-stranded amplicon. This potential series of events is depicted in FIG. 2. The resulting double stranded structure contains in each strand self-complementary sequences that flank, in one strand, a sequence complementary to the primer binding site for the novel primer, and in the other strand a sequence identical to the primer binding site for the novel primer. As a result of this, each strand is capable of forming a stem-loop structure at one end of the amplicon. The exposure of the primer binding site in the single-stranded loop structure can then generate a further series of primer binding and displacement reactions by the same process previously depicted in FIG. 1, thereby allowing generation of non-linear amplification of the sequences of interest under isostatic or limited cycle conditions. This product is different than that created by Rose et al. by non-linear amplification since their processes led to the extended sequences always being located between self-complementary regions whereas in this aspect of the present invention, the extended sequences are outside of the stem-loop regions. In addition, the processes of this aspect of the present invention regenerate a binding site by secondary structure formation whereas in Rose et al., the binding site is in the stem region of a potential stem-loop structure and is never available for another binding event without denaturation of the amplification product.

Primer sequences appropriate for carrying out this aspect of the present invention are dependent upon the factors described previously for linear amplification. The segment of the primer that binds to the target must be of appropriate length and base composition in order to allow stable priming at the temperature being used for the reaction. The segment of the primer that participates in self-hybridization after an extension of the primer must be of appropriate length and base composition such that a partial dissociation of the extended primer from the template is sufficient for the creation of a stable secondary structure, i.e., the stem of a stem-loop structure. This structure does not have to be permanent but only sufficiently stable such that it can allow another priming event. In addition, this aspect of the invention involves the creation of a complementary copy of the stem-loop sequences of the extended novel primer. This necessitates that the segment of the primer that participates in self-hybridization after an extension of the primer must be of appropriate length and base composition such that the sequences involved in secondary structure can still be used as templates. In addition to base composition and length, stability of primary and secondary structures can be influenced by the incorporation of modified bases into the primers, the extended sequences or both. These can either raise or lower the Tm of the segments where they are present. An example of a modification of a base that can raise the Tm of a segment can be but is not limited to the addition of an Ethidium Bromide moiety as described in EP 0 231 495 B1. An example of a modification of a base that can decrease the Tm of a segment can be but is not limited to the use of Inosine as described by Auer et al. (1996, Nucl. Acids Res. 24; 5021-5025, contents already incorporation herein).

Figure 5:
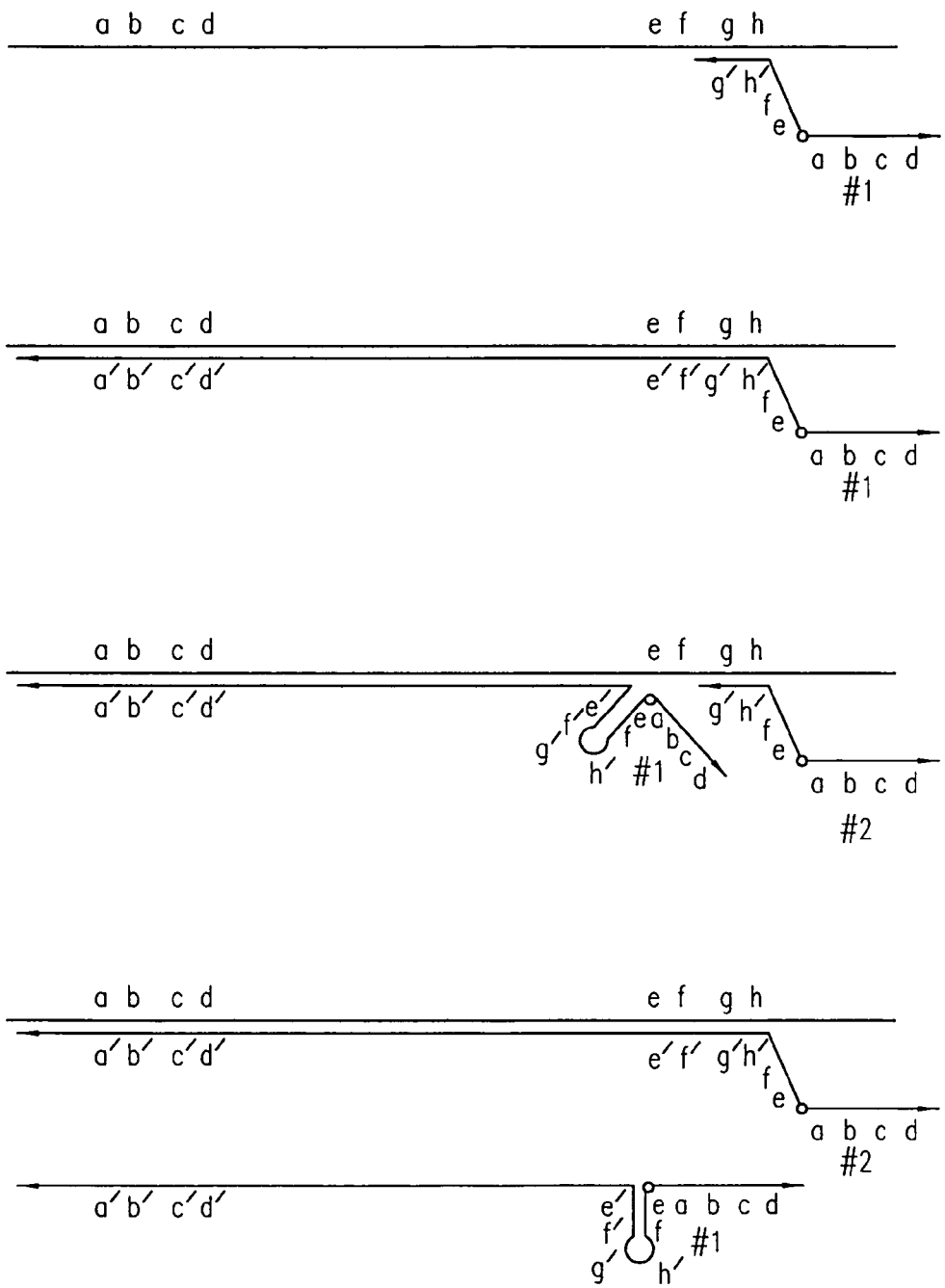
FIG. 5 illustrates non-linear amplification by a pair of novel primers.
Figure 6:
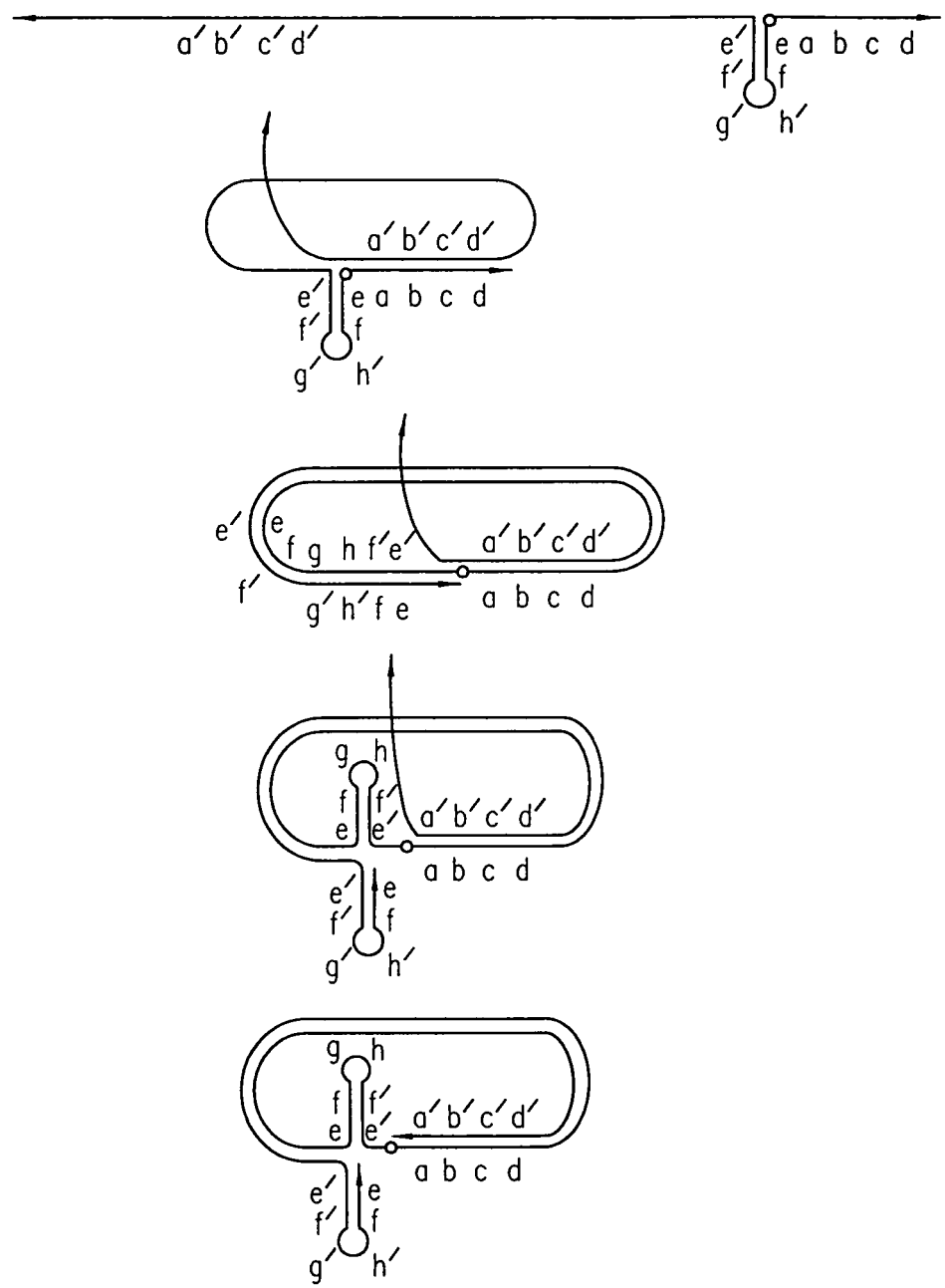
FIG. 6 shows non-linear amplification by a pair of novel primers that contain modifications that prevent part of their sequences from being used as templates.

A non-linear amplification product can also be synthesized under isostatic or limited cycle conditions by a novel nucleic acid construct that comprises two first segments and one second segment. Each of the first segments is complementary to a strand of a nucleic acid or its complement and the second segment is capable of forming a secondary structure after extension of one of the first segments. This construct would be capable of crating a product that has a pair of complementary potential stem-loop structures. This product could be formed by a continuous series of the following steps. One first segment and one second segment of the novel construct could carry out the same continuous series of binding, extension, secondary structure formation, regeneration of a primer binding site, second binding, second extension and strand separation steps that have been described previously for linear amplification by a single novel primer. In addition, the product of this synthesis could be used as a template for a series of binding and extension steps by the other first segment as had been described above for non-linear amplification with a novel primer and a standard primer. A potential series of different forms that these steps could generate is given in FIGS. 5 and 6. The series of events that this novel construct can potentially carry out is the same as described previously and the final product shown in FIG. 6 is the topological equivalent of the final product of FIG. 2 with the two 5' ends of the primers bound together.

A non-linear amplification product can be synthesized by the use of two novel primers that are complementary to different strands of a target nucleic acid by a continuous series of the following steps under isostatic or limited cycle conditions. Novel primer (A) binds to a target strand and there is the same series of extension, secondary structure formation, regeneration of a primer binding site, second binding, second extension and separation of the extended primer from the template as described previously for linear amplification with a single novel primer. As extended novel primers are displaced by binding and extension of other novel primers, these single-stranded products can bind novel primer (B) and allow it to be extended to create a full double-stranded amplicon. This potential series of events is depicted in FIG. 3. As described previously, the formation of the complement of an extended displaced primer creates a template with secondary structure that should allow multiple binding, extension and displacement events under isostatic or limited cycle conditions. A product can be formed that has secondary structure at one end derived from sequences contributed from the first novel primer and its complement and secondary structure at the other end derived from sequences contributed by the second novel primer and its complement. Since this structure has a loop structure on each strand that regenerates a single-stranded segment capable of being used as a primer binding site, further binding and extension of novel primers or nucleic acid constructs can be initiated on either strand under isostatic or limited cycle conditions. Although for purposes of illustration the series of events shown in FIG. 3 are a result of a primary initiation event at one end by novel primer(A), it is understood that with the availability of the complementary template strand, the series of events could have been depicted in a similar fashion with a primary initiation at the primer binding site of the complementary target strand by novel primer (B).

Novel primers can also be modified such that the second segment is unable to be used as template while still capable of participating in secondary structure formation through self-hybridization. Means that can be used to introduce such modifications can include but are not limited to the inclusion of abasic sites and peptide nucleic acids. Methods of synthesis of such primers have been described in U.S. patent application Ser. No. 08/749,266, cited supra and already incorporated herein. A product that could be created by template dependent bindings and extensions of such novel primers or primer constructs is a double-stranded amplicon that is capable of having in each strand a single stem-loop at one end and a single-stranded primer binding site at the other end.

This product can be synthesized by these modified novel primers in a continuous series of the following steps. The first series of potential primer binding, extension, secondary structure formation, regeneration of a primer binding site, second binding, second extension and separation of the extended primer from the template can be as described previously for linear amplification with a single novel primer. The series of reactions with the second modified novel primer are shown in FIG. 4. Since it cannot be used as a template, the second segment of the modified novel primers has no complementary strand that would otherwise compete against the self-hybridization of the second segment with the sequences created by extension, thereby allowing more efficient formation of a secondary structure. Thus, even though there is no stem-loop structure at the 3' ends of the molecule, segments are sufficiently exposed that can be used for more additional priming events.

Figure 7:
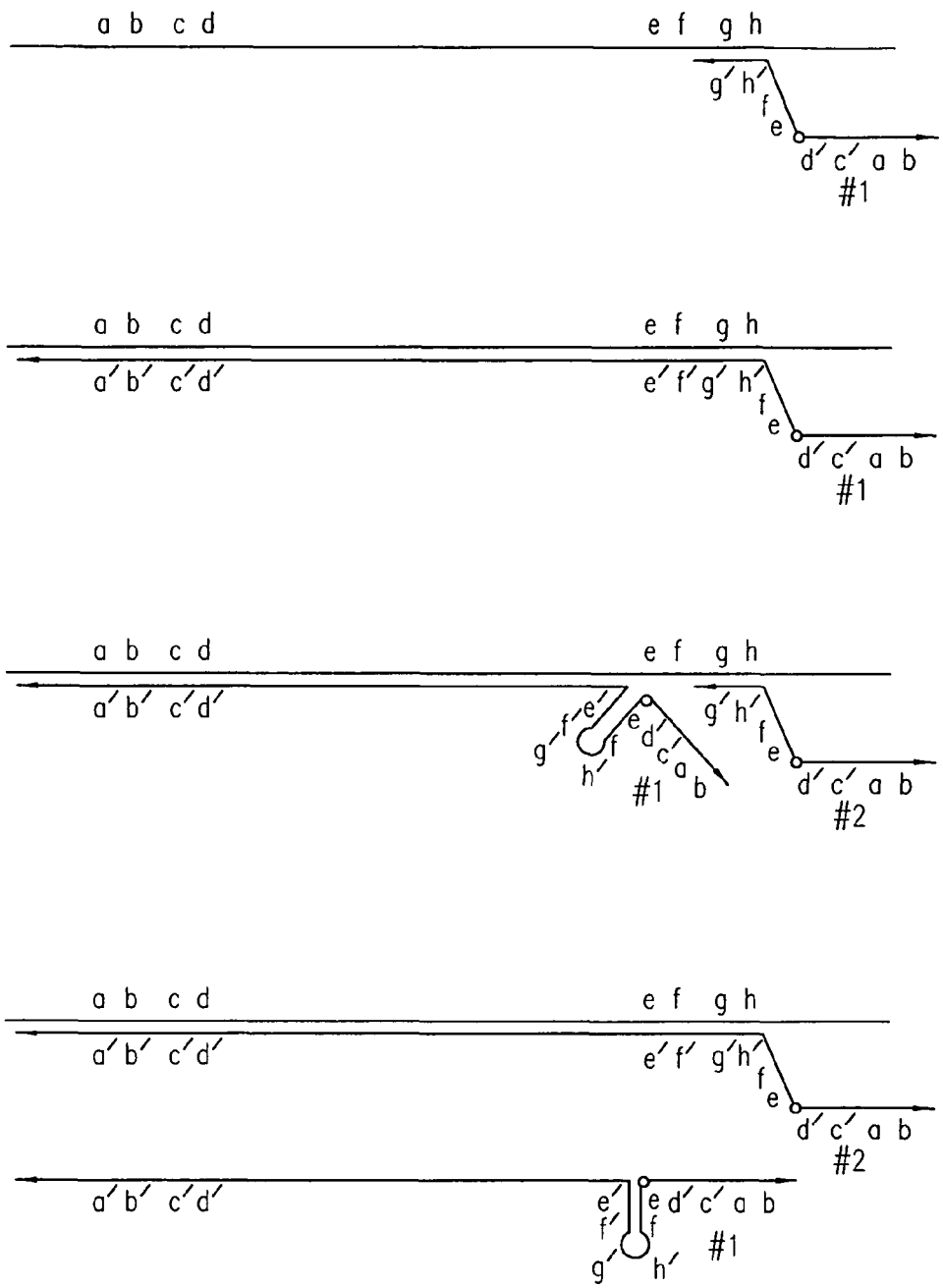
FIG. 7 depicts a series of reactions that can be carried out by a nucleic acid construct with two 3' ends where each of the 3' ends is capable of hairpin formation after template dependent extension.
Figure 8:
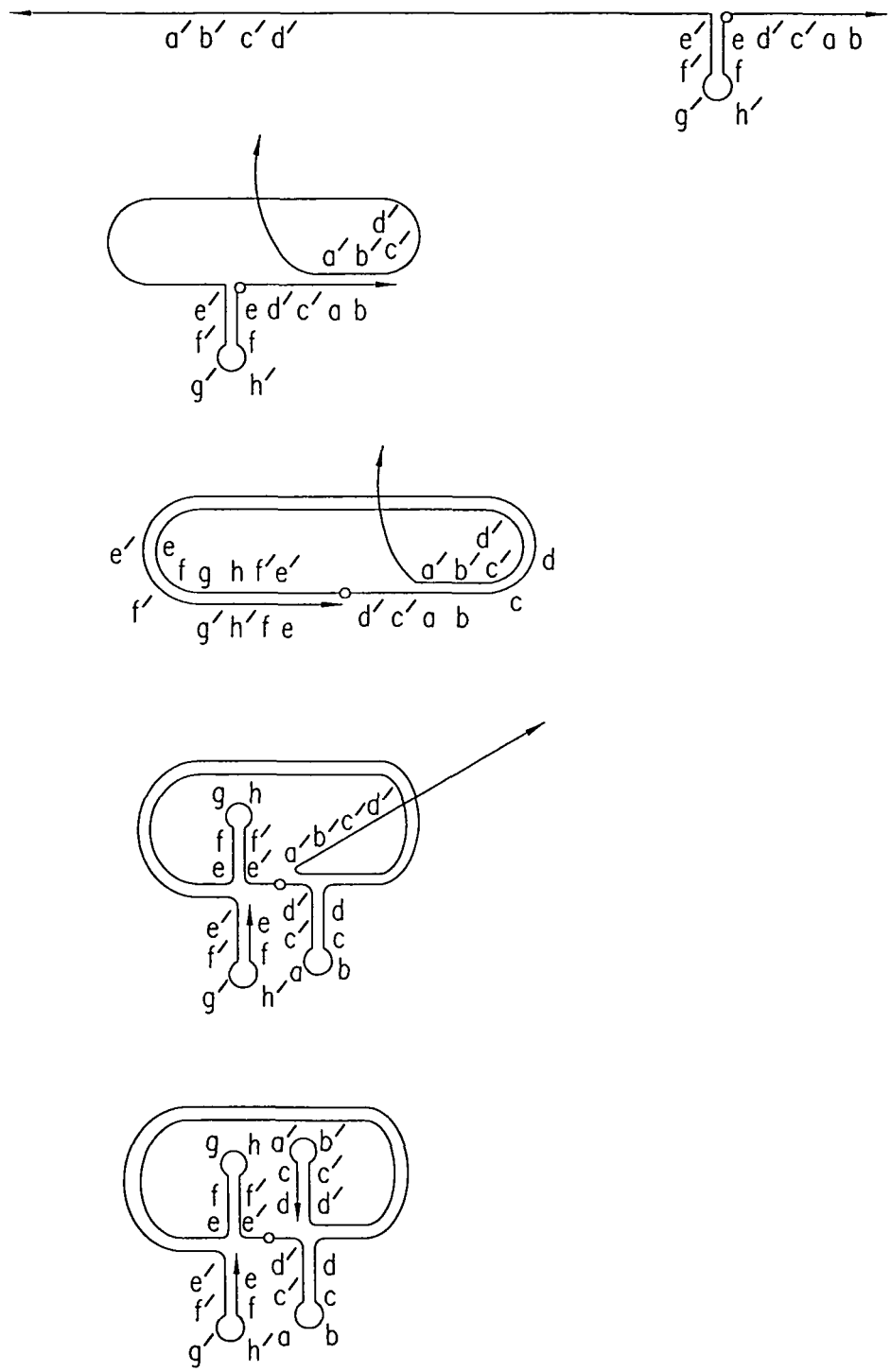
FIG. 8 is a continuation of the process and events shown in FIG. 7.

A non-linear amplification product can be formed under isostatic or limited cycle conditions by a novel nucleic acid construct that comprises two first segments and two second segments. Each of the first segments is substantially complementary to one strand or its complement and each of the second segments is capable of forming a secondary structure after extension of one of the first segments. This construct would be capable of forming a product that has two pairs of complementary potential stem and loop structures. This product would be synthesized by one first segment and one second segment carrying out the same continuous series of binding, extension, secondary structure formation, regeneration of a primer binding site, second binding and second extension steps that have been described previously for non-linear amplification by a single novel primer. The product of this set of reactions could then be used by the other first segment and second segment of the novel construct to carry out the series of reactions described above. A potential series of different forms that these steps could generate is given in FIGS. 7 and 8. The series of events that this novel construct can potentially carry out is the same as described previously and the final product shown in FIG. 8 is the topological equivalent of FIG. 4 with the two 5' ends of the primers bound together. Although novel constructs with more than one polarity have been used to illustrate various arrangements that can carry out linear and non-linear amplification under isothermal or limited cycle conditions it is understood that contructs with branched DNA can also be used for similar processes.

The compositions and methods of use of the aspects of the present invention that have been described above are capable of carrying out linear or non-linear amplification without any of the limitations of previously described art. In these aspects of the present invention, there is no necessity for the full cycle conditions, RNA intermediates, modified nucleotides or multiple enzymes that have been required in previous art.

Self-Propagating Novel Primers and Nucleic Acid Constructs

In all other amplification systems that have been described in previous art, no one has disclosed non-linear amplification without the requirement for two binding sites, one on each target strand. This requirement is due to the necessity for the presentation of sequences for each strand. Systems with this requirement have included thermal systems such as PCR and LCR and isothermal systems such as 3SR and SDA. As such, PCR reactions are performed with two primers, where each strand of a target nucleic acid is used by one or the other primer. Even in the disclosure of Rose et al., two identical binding sites are required to carry out PCR so the same primer could be used for each strand.

One aspect of the present invention discloses compositions and methods of use for non-linear amplification where one or more binding sites for novel primers and nucleic acid constructs are confined to only one strand of a target nucleic acid. The novel primers and novel constructs of this aspect of the present invention have at least three segments. These segments can be joined together either covalently or non-covalently. Means of joining segments through covalent linkages can include but are not limited to the phosphate backbone of normal linear nucleic acids, constructs that have more than one polarity and branched DNA constructs. Methods of synthesis of such constructs have been described in (INV patent). Means of joining segments by non-covalent linkages can include but are not limited to ligand-receptor bonds and complementary base pairing. The segments may be adjacent to each other or they may be spatially separate from each other. The sequences of the segments may be distinct from each other or they may be complementary or identical to each other.

When a single novel primer has a single polarity, it has three segments with the following characteristics:

1) The first segment of the novel primer is capable of binding and extension and comprises sequences that are substantially complementary to sequences in only one strand of a target of interest such that it can bind to the target and be extended using the target sequence as a template.

2) A second segment of the novel primer comprises sequences that are substantially identical to sequences in the target of interest such that the second segment is capable of self-hybridization with sequences created by target dependent extension of the first segment allowing a secondary structure to form which promotes self-priming events.

3) A third segment of the novel primer is capable of acting as an intrastrand template and thereby allows self-extension.

By virtue of these characteristics, the presence of one strand of an appropriate target molecule can convert a single novel primer into a self-propagating nucleic acid capable of non-linear amplification. The single novel primer of the present invention can bind to a target and utilize it as a template for extension. Due to the presence of the second and third segments, this product is then capable of undergoing a series of intrastrand and interstrand binding and extension reactions. The products of these reactions are self-propagating single-stranded nucleic acids or self-propagating double-stranded nucleic acids. The single-stranded nucleic acid products are capable of forming stem-loop structures and the double-stranded nucleic acids are capable of forming stem-loop structures after being rendered single-stranded.

Figure 9:
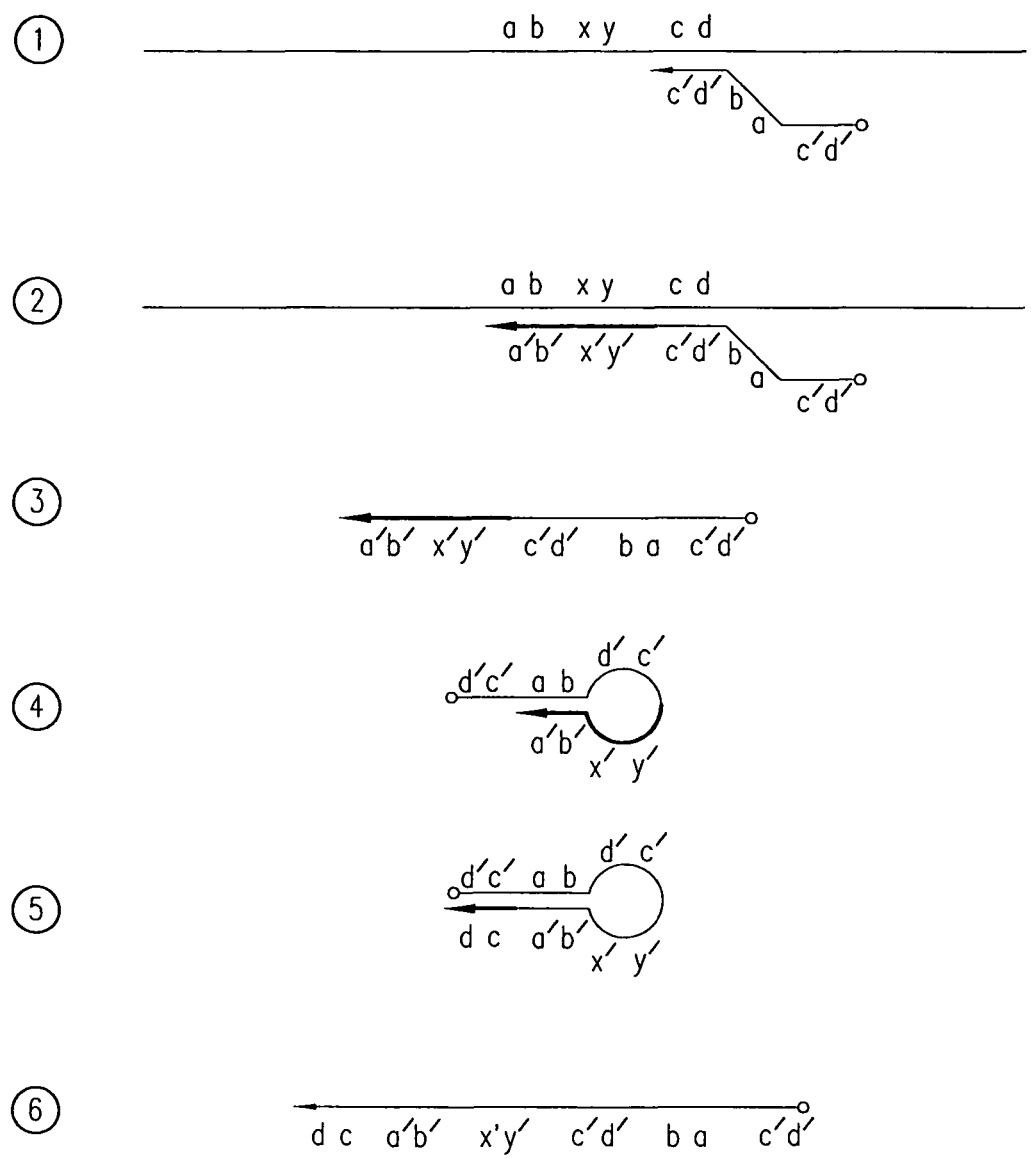
FIG. 9 illustrates template dependent extension and self priming/self extension of a single primer capable of non-linear amplification.
Figure 10:
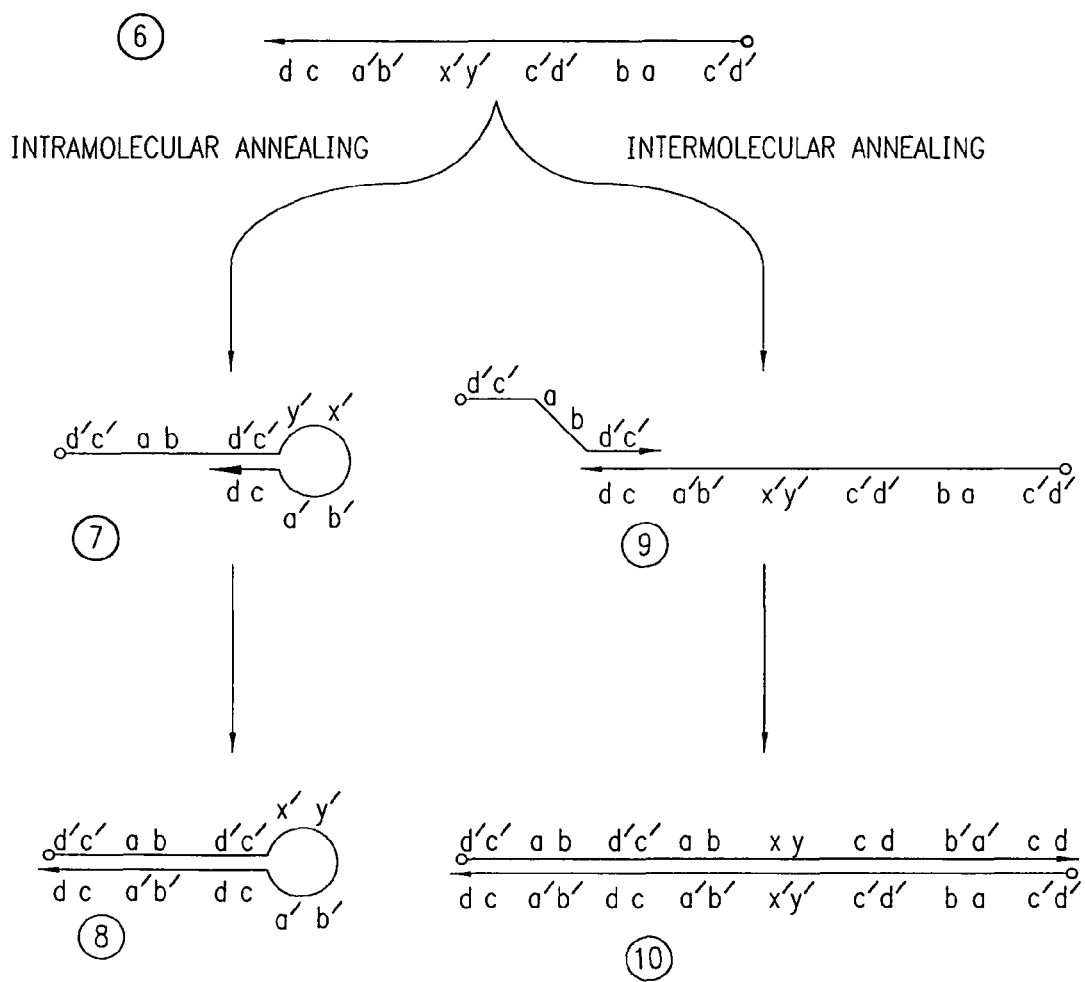
FIG. 10 shows continuation of the process and events of FIG. 9. Potential intramolecular annealing and intermolecular annealing allows the continuous addition of sequences.
Figure 11:
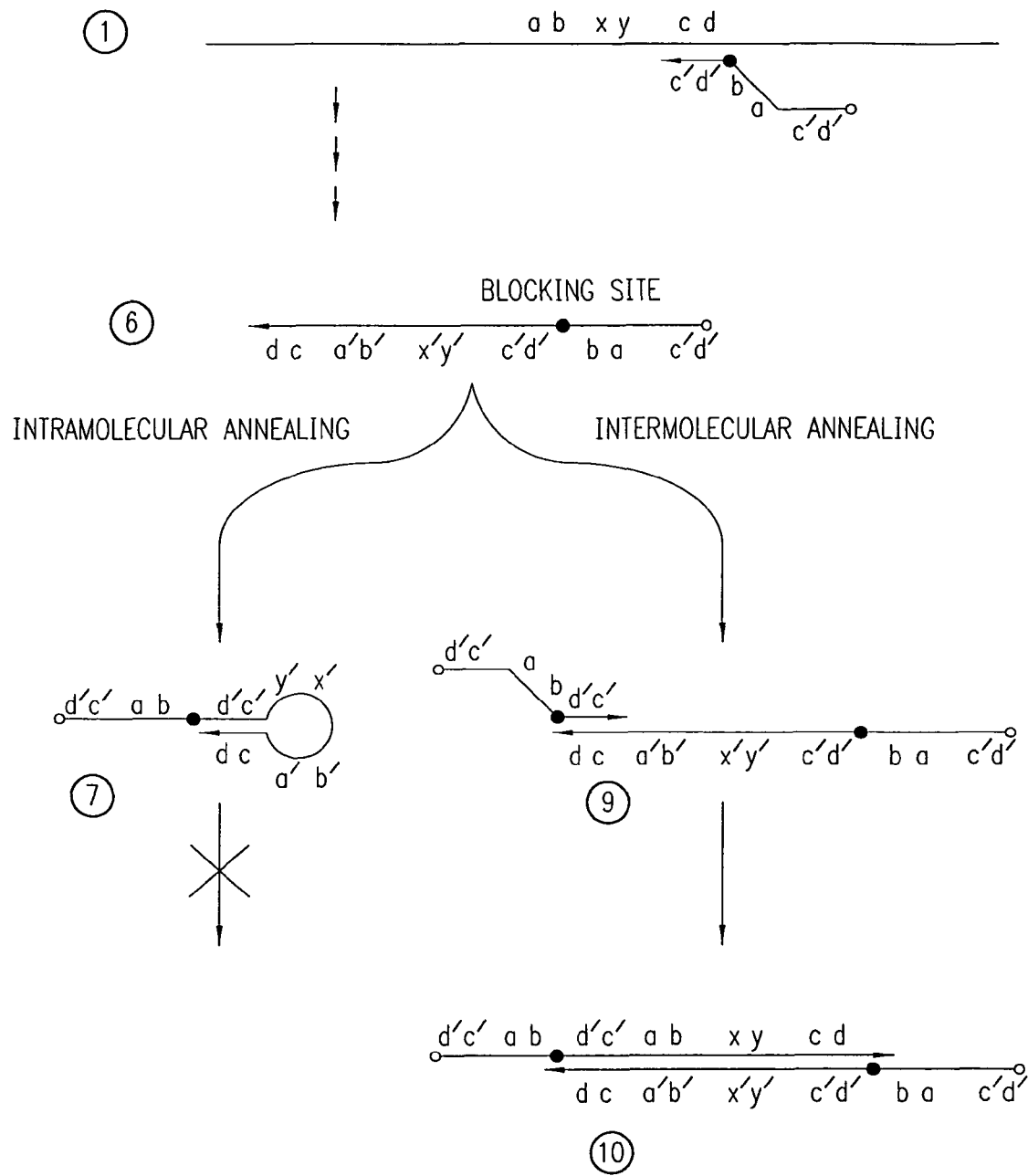
FIG. 11 are further illustrations of the modification of the processes and events in FIG. 10 wherein the initial primer contains a modification that does not allow a portion of the primer to be used as a template.

A series of steps that can be used to synthesize such forms from linear novel primers by the presence of the appropriate strand of a target nucleic acid are shown in FIGS. 9, 10 and 11. A novel primer can bind to a template and be extended to form the structure of step 2 of FIG. 9 where synthesis is limited to copying only a discrete portion of the available template. A constraint on the extent of synthesis can be carried out by a variety of means. These means can consist of but are not limited to size, time and substrate constraints. For a size restraint, the target can be treated prior to extension by means that create random or site-specific ends. Random sites can be used to create a pool with a select average size. Means for producing random breaks in target nucleic acid can include but are not limited to physical methods such as shearing and enzymatic methods such as a nuclease. Site-specific sites can be used to create target nucleic acids that have a discrete size. Means for creating site specific ends can include but are not limited to restriction enzymes. For a time constraint, the reaction can be carried out for a time interval that is sufficient for the binding and desired length of synthesis followed by an adjustment of the temperature to stop the reaction. The duration of the time interval is determined by factors that can include but are not limited to buffer and salt conditions, the choice of temperature used for binding and extension, the use of modified substrates that are used with a different efficiency compared to normal substrates and the choice of the particular polymerase. For substrate constraints, the primer sequences can be chosen such that the desired extent of the extension reaction can be carried out by a limited number of particular nucleotides and excluding from the reaction the particular nucleotide or nucleotides that would allow synthesis further than the desired extent. For instance, omission of dTTP from a reaction mix would allow template dependent extension of the primer with dCTP, dGTP and dATP with termination of the growing strand occurring at the point where dTTP is required.

The efficiency with which extensions are stopped at the appropriate sites affects the overall efficiency of the reaction. It is understood that it is desirable that the stoppages be as complete as possible to insure that the target templates have been used to produce the maximal amounts of intermediates that are capable of participating in the steps of the reaction that will be further described for this process. On the other hand it should be noted that the constraints do not have to be absolute in nature. As long as some of the extension reactions are limited appropriately, reaction products are created that can undergo the further steps that are described below.

After the primer has been extended to the desired extent, the primer is separated from its template (FIG. 9, step 3). Although not shown in this Figure, this could potentially take place by formation of a secondary structure through self-hybridization between the extended sequences and the second segment of the novel primer (the a'-b' and a-b segments of the novel primer shown in FIG. 9). This would allow binding and extension of other single novel primers with the same target molecule followed by displacement of the extended primers under isostatic or limited cycle conditions as has been described in previous aspects of the present invention. However, in the absence of a design of sequences in the novel primer that would allow this event to occur, separation of an extended primer from its template could be carried out by thermal denaturation in step 3 of FIG. 9, i.e., full cycle conditions. The sequences for a-b can be chosen such that they are sequences that are adjacent to the c-d sequences in the target or as illustrated in FIG. 9 they can be separated from these sequences by a segment of appropriate length designated x-y.

After either a self-catalyzed or a thermal release step, the partially extended primer is capable of a self-priming event by hybridization of complementary segments as shown in step 4 of FIG. 9. This allows self-extension of the primer using the third segment of the single novel primer as the template. When a limited subset of the four dNTP's is used for control of the extension length in step 2 of FIG. 9, the missing nucleotide(s) may have to be added for this further extension step. Similarly, adjustments in reaction conditions may also be needed when factors such as buffer, salt, temperature, polymerase or modified nucleotides have been used to influence the time interval for the limited extension step. The secondary extension of the primer in step 5 of FIG. 9 adds sequences that are complementary to the 3' end of an unextended primer. Step 6 shows the denaturation of the product of Step 5 of FIG. 9. The extended primer can then undergo either an intra-strand self-hybridization event or an inter-strand hybridization event. The intra-strand self-hybridization can be between the extended end and either the first segment or the third segment of the extended primer. Self-hybridization of the extended primer with the first segment is a self-priming event that would form the structure seen in step 7 of FIG. 10. This form is capable of undergoing self-extension (step 8 of FIG. 10). In addition to self-propagation of sequences by these potential intra-strand events, it also can take place by inter-strand hybridization. The binding of an initial novel primer to an extended novel primer is shown in step 9 of FIG. 10 followed by the extension of the initial novel primer and the further extension of the extended novel primer as shown in step 10 of FIG. 10. Although not shown in this Figure, there can also be an inter-strand hybridization between extended novel primers that could allow extension of each. Therefore, both by intramolecular and by intermolecular annealing, the extended primers can undergo the continuous addition of sequences after a denaturation event. The product of a series of reactions as depicted in FIGS. 9 and 10 would be a series of amplicons with various sizes depending upon which route of extension was taken (intramolecular or intermolecular) and how many rounds of denaturation/extension took place.

In another aspect of the present invention, a novel primer with three segments can be modified such that self-priming and self-extension take place only during the limited synthesis step and self-propagation takes place by intermolecular bindings and extensions. This can be carried out by having a segment in the primer that partially or totally blocks its use as a template (FIG. 11). Methods for modifying novel primers for this purpose have been described previously. The presence of a site that is blocked as an extension template can still allow the same potential series of reactions that were shown in steps 1-6 of FIG. 9. However, after intermolecular hybridization of an initial novel primer with an extended novel primer (Step 9 of FIG. 11), only the unextended primer could have new sequences added to its 3' end whereas the previously extended primer would remain the same length (step 10 of FIG. 11). This event allows the further production of extended primers that can in turn be templates for additional extension events thereby creating a self-propagating construct. In this way there can be non-linear amplification of an amplicon with a discrete size that comprises a double-stranded segment flanked by single-stranded 5' tails.

Constructs with Self-Priming Hairpins

The formation of a self-propagating nucleic acid from a single strand of target nucleic acid can also be carried out by nucleic acid constructs that comprise one or more first, second or third segments. These constructs could have more than one polarity or they could be branched DNA. In this aspect of the present invention, the segments of the construct have the following characteristics:

1) One or more first segments are substantially complementary to sequences in only one strand of a target of interest such that they can bind and be extended using only said strand of the target sequence as a template.

2) One or more second segments of the construct are substantially identical to sequences in the target of interest such that they are capable of self-hybridization with sequences created by target dependent extension of a first segment of the construct allowing a secondary structure to form that promotes self-priming events.

3) One or more third segments of the construct are capable of acting as intrastrand templates and thereby allowing self-extension.

First segments of a construct may be substantially identical to each other or they may be substantially dissimilar to each other. The second and third segments may also be described in this way. Various arrangements of sequences can be used for such constructs. For purposes of illustration, examples of such arrangements are given for constructs with multiple polarities. In this aspect of the present invention, the final product of template dependent bindings and extensions followed by intrastrand and interstrand bindings and extensions are constructs that are capable of forming one or more stems and one or more loops by intramolecular hybridization.

A self-propagating nucleic acid can be formed by a novel nucleic acid construct that has one first, second and third segment. In this example, the second segment has its own 3' end because it is part of a construct with more than one polarity. However, it still functions only as a second-segment due to a blockage of the 3' end. This blockage of extension can be carried out by any of a number of means known to those skilled in the art.

Figure 12:
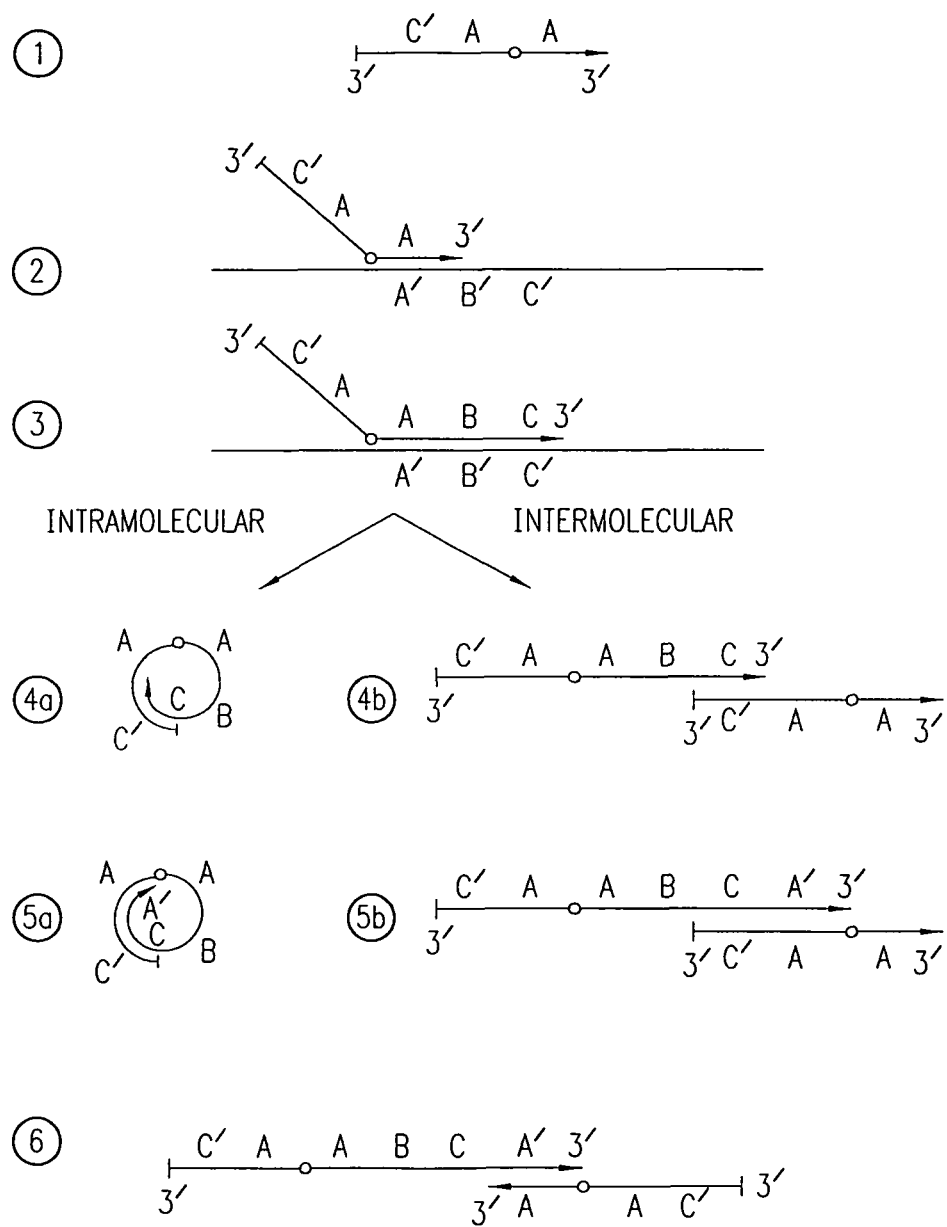
FIG. 12 are illustrations of a novel nucleic construct with two 3' ends that is capable of non-linear amplification.

A potential series of events that can take place when this construct is contacted with an appropriate target strand is shown in FIG. 12. After binding to the appropriate target strand, the first segment can undergo limited extension. The same potential means of limiting the extent of synthesis by size, time and substrate constraints previously described for limiting synthesis also find utility in processes with this construct. The extended strand is then capable of either intra-strand binding with the second segment of the same construct (step 4a) or inter-strand binding with the second segment of another construct molecule (step 4b). With either of these arrangements further extension can take place by using the third segment as a template (step 5a and 5b). The product of either of these processes is an extended construct that is capable of self-propagation by being used as a template for binding and extension of more initial primer constructs (step 6 of FIG. 12).

Figure 16:
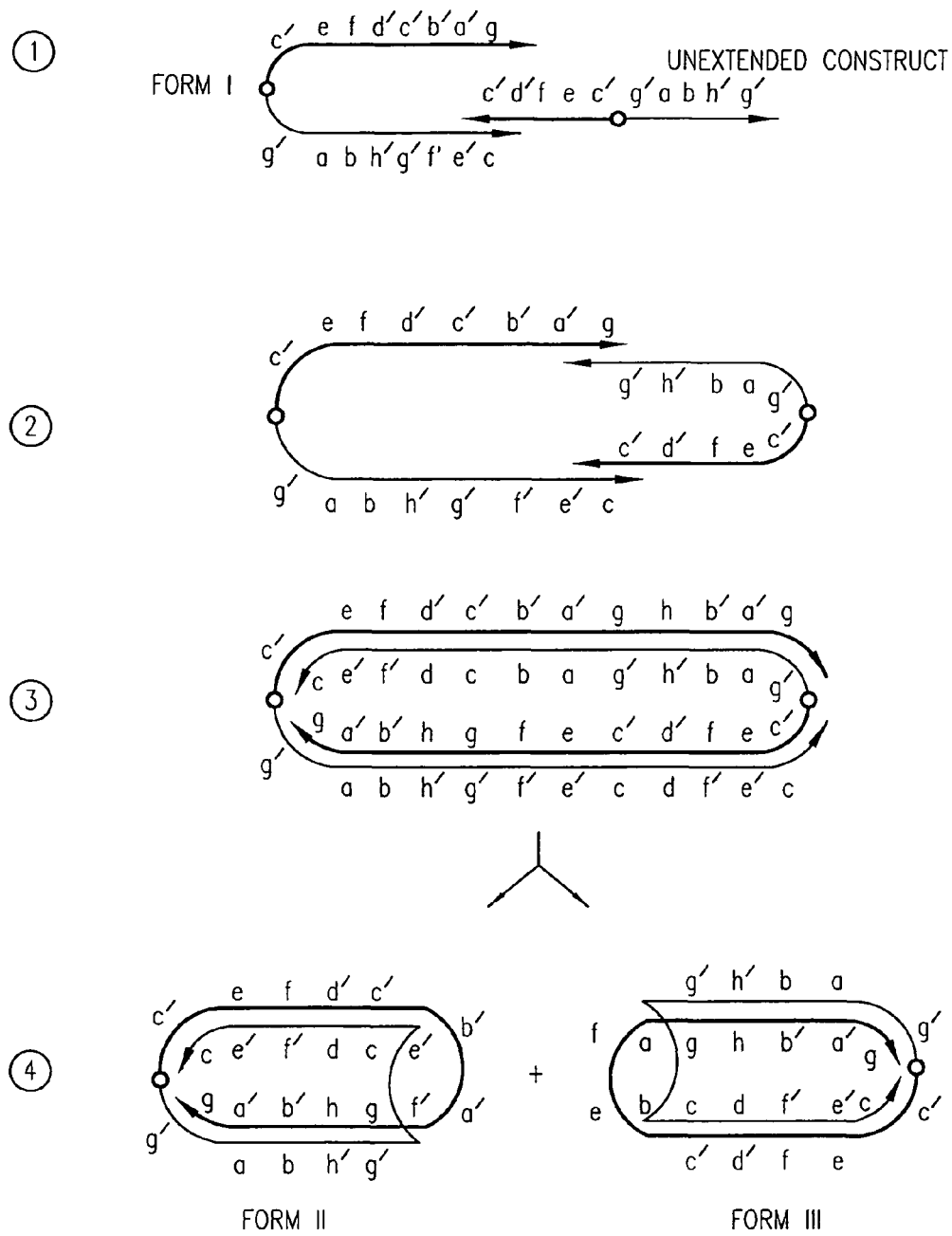
FIG. 16 is a continuation of the processes and events shown in FIG. 15.

A self-propagating nucleic acid can also be formed by a novel nucleic acid construct that has two or more first, second and third segments. Depending upon the design of the construct, a self-hybridization event can occur within the same extended strand or it can occur between different extended strands of the construct. Although constructs with multiple polarity or branched DNA can physically comprise a single strand, for the purposes of clarity a strand in a construct refers to a continuous stretch of nucleic acid that has a single polarity. An example of constructs that have two first, second and third segments with the strand arrangements described above are given in FIG. 13 and FIG. 15. The constructs used in this aspect of the present invention are related to the previous aspects that were exemplified in FIGS. 9, 10 and 11. In common with these, synthesis is limited to copying only a discrete portion of the available template. The same size, time and substrate constraints previously described for limiting synthesis also find utility in these aspects of the present invention. Thereby, step 3 of FIGS. 13 and 15 are equivalent to step 2 of FIG. 9 with the exception that a single template molecule is used for extension of two 3' ends rather than only one. Release from the template can allow self-hybridization in the construct followed by further strand extension. The arrangement in FIG. 13 allows intrastrand binding and extension within a construct whereas in FIG. 15 there is inter-strand binding and extension within a construct. For both of these arrangements there can be a denaturation event that can allow further self-priming and self-extension reactions by use of different copies of the repeated segments of the constructs. However, FIGS. 14 and 16 illustrate a series of events that demonstrate the ability to self-propagate by binding to unextended constructs and initiating mutual extension events.

Figure 14:
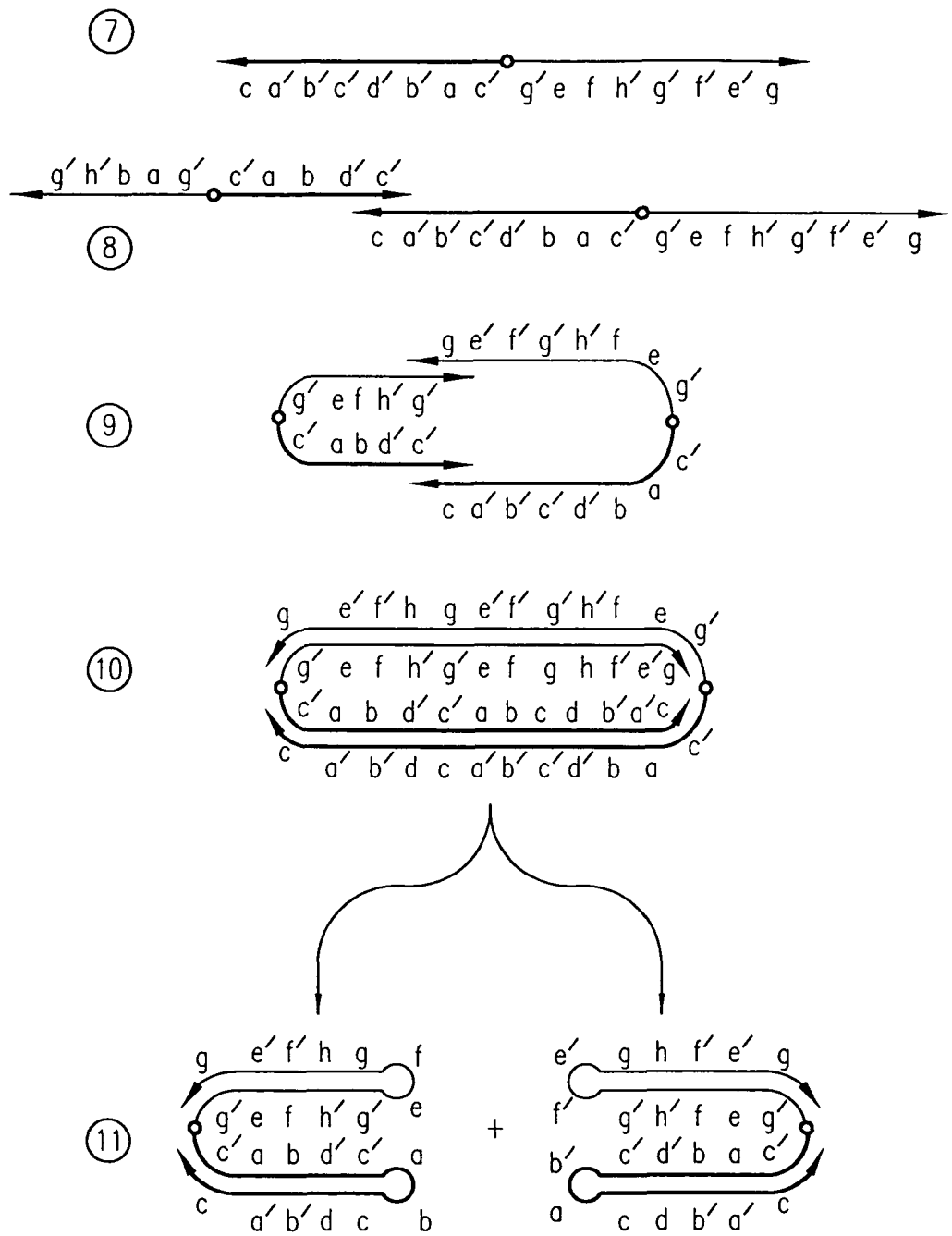
FIG. 14 is a continuation of the processes and events shown in FIG. 13.

The products of the target dependent extension reactions illustrated by FIGS. 9 through 16 are different depending upon the particular arrangement of the segments in the initial construct. However, they do share a common secondary structure characteristic. The products of the present invention have intramolecular forms that constitute single-stranded regions as well as self-complementary double stranded regions. These single-stranded regions can be drawn as loops (the products of FIGS. 9, 10, 11, 13 and 14). They can be part of a circle (the product of FIG. 12). They can be part of double single-stranded loops consisting of non-complementary sequences located between two double-stranded regions (FIGS. 14 and 15). This characteristic is in contrast to the products of previously described constructs with multiple polarities (INV patent) where the intramolecular products were completely made up of self-complementary sequences.

Although novel acid constructs have been described that used more than one polarity for the preceding reactions it is understood that branched DNA constructs could have been used for the same series of reactions and equivalent products. Also, the constructs with more than one polarity that have been described in this aspect of the present invention are different from those described in (INV patent). In that previously described art, the segments capable of extension were complementary to both strands of a target nucleic acid, whereas in the present invention the entire reaction is carried out by template-dependent priming and extension of segments that are complementary to one and only one strand of a target nucleic acid.

Simplification of Reactions and Reaction Products

In all amplifications including the present invention, there are side reactions that can also take place during the reaction. These can form a complex variety of higher molecular weight products. They can be deleterious in terms of reducing the efficiency of either synthesis of the desirable sequences or the efficiency of detection of these sequences. Reduction of efficiency of synthesis can take place when the side reactions reduce the amount of synthesis of desirable sequences by competition for polymerase and substrates resources. The side reactions can also reduce efficiency when appropriate sequences are synthesized but they are in secondary structures that are inhibitory to some of the steps of the reactions. This can take place by structures that interfere with either binding or extension of primers. In the latter case there can be a loss of efficiency due to an inability to use a primed template and also due to a loss of polymerase activity if the enzyme is bound but unable to proceed. Inappropriate secondary structures can also create problems in the detection of appropriate sequences.

Novel methods are disclosed that can be used to reduce the effects of these secondary reactions. These methods can be used with various aspects of the present invention that have been previously disclosed and it is understood that they may also be used in conjunction with methods of amplification that have been described by others. Since a self-propagating system uses products as templates for further reactions the extent of synthesis of any product can be controlled by reduction in the average size by including a limited amount of terminator nucleotides into the reaction. In this way a product can be synthesized that cannot undergo side reaction extensions but can still be used as a template for extensions by other primers or primer constructs. This can increase the amount of appropriate sequences synthesized and reduce the amount of potential inhibitory elements. Abrogation of the effects of secondary structures can also be carried out by post-synthesis methods that either eliminate secondary structures or release the target sequences from association with such structures. An example of the former method can be treatment with a single-strand specific nuclease that digests the loops and junctions of secondary structures. Disassociation can be carried out by digestion with restriction enzymes that can isolate the desirable segments away from other DNA sequences. Elimination and dissociation can be carried out simultaneously by limited digestion with DNase or physical treatments such as depurination. The product of these treatments would then be rendered more efficient in terms of signal generation by a variety of detection means.

Polynucleotides Containing Negatively Charged Modified Nucleotides

In another aspect of the present invention, methods and compositions are disclosed that use nucleotide analogues that allow amplification of double-stranded DNA targets when using denaturation temperatures that are below those of the corresponding unsubstituted double-stranded segment. This is carried out by the introduction of bases modified by negatively charged constituents that reduce the Tm of an extended product. In contrast to the teachings of Auer et al. described previously, the substitution of the modified bases of the present invention base still allows temperatures for binding that are in the range commonly used with unmodified bases. The lower temperatures that were described by Auer et al. have the limitation that it is well known in the art that the use of lower temperatures for binding of primers to nucleic acid targets can contribute to non-specific priming with non-target nucleic acid templates and also to increased primer-dimer formation. The present invention avoids these limitations by retaining the ability to use higher binding temperatures in the presence of modified bases. Whereas in previously described art, the difference between the highest and lowest temperatures used in full cycle PCR can range between 25-50° C., the present invention can use a compressed series of cycles that differ by less than 10° C. Thus the present invention provides the use of a temperature that is high enough to preserve efficient specific annealing of primers while at the same time is low enough to avoid exposure of the enzyme and nucleotide substrates to temperatures that allow considerable levels of inactivation during the time used for the reaction.

Post-Synthesis Labeling

In the present invention, novel compositions and methods are disclosed for the generating non-radioactive signals that overcome the limitations in prior art that are intrinsic to the use of large bulky groups that have previously been used in obtaining sequence information. It has been known previously in the art that in general, chain terminators have a problem being incorporated by polymerases. It has also been long known that the presence of large bulky groups useful in signal generation creates a further reduction in incorporation efficiency. An example of this is a group of fluorescently labeled dideoxy nucleotides that weren't substrates for the Klenow fragment of polymerase I although they could be used by AMV Reverse Transcriptase and T7 polymerase (Prober et al., 1987, Science 238; 336-341, contents incorporated herein). Both of these factors can reduce the overall level of incorporation, which in turn reduces the amount of terminations and signal production. In particular, longer strands of DNA are adversely affected since termination of these loci is usually generated by reducing the amount of termination nucleotides compared to normal nucleotides; thereby adding further stress on the likelihood of their incorporation.

In the present invention, these limitations are overcome by covalent linkage of a signal generation moiety to a reactive group in a terminator nucleotide after the strand extension and termination events are concluded. This is in contrast to previous methods that incorporate a label either prior to or during strand elongation.

In this aspect of the present invention, reactive groups include those that a) provide substantially specific covalent linkage of signaling moieties to terminal nucleotides rather than internal nucleotides and b) do not substantially inhibit incorporation of the modified terminator nucleotides or interfere with analysis by electrophoresis. Examples of reactive groups that can be added to a terminator nucleotide can include but are not limited to thiol, alkyl halide, free or protected primary and secondary amine groups. Methods for creating derivatives with reactive groups can be but are not limited to those described by Ward et al., in U.S. Pat. Nos. 5,476,928; 5,241,060; 5,260,433 and 4,707,440, cited supra and already incorporated herein by reference. Groups useful in signal generation can then be attached to the terminated strands without regard to any inhibitory effects upon enzymatic activity or substrate utilization. Groups useful in detection can include but are not limited to haptens, ligands, receptors, fluoroscein, rhodamine, coumarin and other fluorescent molecules, infra-red fluorescent groups, chemiluminescent moieties, energy transfer systems and enzymes. Other useful reactive groups include bulky or charged groups that when incorporated into terminating nucleotides render them unusable as enzyme substrates. Such groups include Texas Red and donor conjugates for delayed fluorescense. Methods for attachment of signal generating groups to reactive groups are described by Ward et al. in U.S. Pat. No. 5,476,928, and also U.S. Pat. Nos. 5,241,060; 5,260,433 and 4,707,440, already incorporated herein. This aspect of the invention can be carried out in conjunction with methods disclosed previously for production of multiple copies from a single template under isostatic or limited cycle conditions. In addition, it is understood that post-polymerisation labeling can also be carried out when using any means that have been described previous to the disclosure of the present invention.

This method is in contrast to the original description of using the chain terminator as a source of signal generation as described by Hobbs and Cocuzza in U.S. Pat. No. 5,047,519 (incorporated herein) teach away from the present invention where they explicitly state that "To be useful as a chain-terminating substrate for fluorescence-based DNA sequencing, a substrate must contain a fluorescent label . . . ". The present method overcomes the limitation that either dNTPs or ddNTPs have to be marked prior to incorporation in any of the commonly employed means of sequence analysis of labeled DNA strands. These can include both static systems and real time analysis. Examples of static systems would include but not be limited to acrylamide gel separations followed by photography or chemiluminescence detection. Examples of real time analysis would include but not be limited to acrylamide gel separations followed by detection of a single dye as used by Ansorge et al., 1986 or it could be distinct dyes for each base termination as described by Smith et al., in U.S. Pat. No. 5,171,534 and Prober et al., in U.S. Pat. No. 5,332,666. The contents of the foregoing publication and two patent documents are incorporated herein by reference. It is also understood that although the present invention has been described in terms of chain termination by dideoxynucleotides, other chain terminators can also be used. A description of various chain terminators is given in "DNA Replication", $2^{nd}$ Edition, by A. Kornberg and T. A. Baker, 1992, 447-449, W.H. Freeman and Co., NY, N.Y., incorporated herein. Examples of changes in the sugar ring can include but not limited to acyclo and arabinosyl dNTPs. When used as terminal nucleotides these derivatives may be of particular use since chemically and biochemically they should be well distinguished from the normal nucleotides that comprise the other parts of the DNA strands. It has also been shown in U.S. Pat. No. 5,332,666 (incorporated herein) that fluorescently labeled acyclo derivatives can produce sequence ladders that are equivalent to ones derived by radioactive labeling. In addition, blockage of chain termination by the presence of an amino group in the 3' position of a terminator nucleotide can also provide a functional group for the post-synthesis attachment of a signal generating moiety. Other blocking groups can be used that are capable of regenerating an active 3'-OH end of a strand. For instance when a photocleavable group is included as described in the art by the 3' OH can be regenerated after the reaction has been terminated and used for attachment of a label. Systems that could be used for this function include but are not limited to incorporation of a fluorescently labeled dideoxynucleotide by terminal transferase.

Another aspect of the present invention is directed towards overcoming limitations inherent in the primer labeling system by separation of the primer labeled extension products that have been terminated properly from those which have not. Such a separation can be achieved by using properties of modified terminator nucleotides. This can be carried out by either a pre-existing marker in the terminator nucleotide or by a post-synthesis modification as described above. Any means that can allow a suitable physical separation between the presence and absence of a marker is considered to be within the scope of the present invention. Examples of such pre-existing markers can consist of but not be limited to biotin, imino-biotin, fluorescein, halogens, thiols, and amines. Means of physically sequestering strands that have such markers can consist of but not be limited to avidin, streptavidin, antibodies and physical matrices that combine with halogens, thiols or amines. After separation of the marked strands from the strands lacking terminator nucleotides, the products can be released in a form that is suitable for sequence. Examples of means for such release can consist of but not be limited to physical denaturation of proteins such as antibodies through heat or chemical treatments. Release can also be carried out by use of a scissable bond such as a disulfide bridge or imino biotin. Methods of use of scissable bonds is described in the Ward disclosures cited supra. Signal generation from the purified strands can be carried out by markers in the oligonucleotide used as a primer, or in the dNTP or ddNTP nucleotides that have been added to the primer.

The processes of the present invention can be adapted to signal generation for all sequencing procedures including those that use a single channel and 4 different dyes as well as procedures that use 4 channels and a single dye. Signals produced in such procedures can be analyzed in real time of by scanning.

Thus, the present invention provides a post-termination labeling process for nucleic acid sequencing comprising three steps. First, nucleic acid fragments corresponding to the nucleic acid sequence of interest are produced in the presence of untagged or unlabeled substrates, untagged or unlabeled primer, polymerizing enzyme, buffer and an appropriate untagged or unlabeled terminator for each nucleotide base. Each of the terminators comprise a chemically reactive group that covalently binds to a tagged molecule under conditions that internal sequences are substantially non-reactive to the tagged molecules and the chemical reactions do not substantially interfere with separation of the fragments in a medium or matrix. Next, the fragments produced in a medium or matrix are separated followed by detection of the separated fragments by means of detecting the tagged molecule in said medium or matrix.

Various embodiments may be included in the above-described post-termination labeling process. In the producing step, for example, the chemically reactive groups of the terminators can be protected prior to their enzymatic incorporation into the fragment produced and they can then be deprotected prior to covalently binding any tagged molecule. The chemically reactive group can comprise a nitrogen, a sulfur or an oxygen atom. Furthermore, the chemically reactive groups on said terminators can be different, or they can be the same. In addition, the tagged molecule can be the same or they can be different for each terminator. Those skilled in the art will readily appreciate that such tagged molecules are known and may be selected from the group consisting of fluorescent dyes, chemiluminescent dyes, infra-red dyes, chemiluminescent entities and electrochemiluminescent entities, or combinations thereof.

In addition to the just described embodiments and features of the post-termination labeling process, the separating step can be carried out electrophoretically, and the medium or matrix can comprise a gel, such as a polyacrylamide gel. Separation can also be carried out by capillary gel electrophoresis.

With respect to detection, this step can be carried out by a means selected from photometric measurement, spectrophotometric measurement, colorimetric measurement, fluorometric measurement, delayed fluorescent measurement and chemiluminescent measurement, or combinations thereof.

Utility of Invention

The various aspects of the present invention that are capable of carrying out linear and non-linear amplification of nucleic acid sequences can fulfill many of the functions that have previously been carried out by methods described in previous art for isothermal and thermocycler dependent methods. These can include but are not limited to sequencing, probe synthesis and labeling, forensic identification, allele identification, genetic screening, isolation and cloning of desirable genes, artificial gene construction, gene expression and diagnostic identification. Reverse Transcriptase or a DNA polymerase capable of reverse transcription can be used to practice the present invention with an RNA molecule as the initial substrate. The reactions can be carried out in the absence of any modifications of the primers or reagents or if desired these can be labeled or otherwise modified. The presence of amplified sequences can be assayed directly either by incorporation of labeled moieties or by direct visualization. Indirect means of identification can also be carried out by hybridization with appropriate probes. These indirect means can include but are not limited to dot blot, slot blot. Southern blot and plate assay formats.

Although certain nucleic acid sequences are required to be present in the primers for binding to template or to create self-complementary regions for multiple priming events, additional nucleic acid sequences can be included in the primer sequences to provide desirable properties by their presence. These can include but are not limited to phage RNA promoters to allow a further amplification of desirable nucleic acid sequences and sequences that can be used for identification or isolation of amplicons. Sequences could be included in primers or a primer construct that would create an amplicon with an inverted repeat at each end. This segment could then be used as a binding site for a single primer or primer construct that could use either strand for binding and extension. Since the choice of the inserted sequence is arbitrary, this segment could be a universal target that could be used for amplification regardless of the sequences in between.

Also provided by the present invention are processes for producing nucleic acid sequences that have decreased thermodynamic stability to complementary sequences. In this process, at least one modified nucleotide or nucleotide analog having a negatively charged chemical moiety is incorporated into the nucleic acid sequences produced.

A further provision of the present invention is a single-stranded or double-stranded nucleic acid polymer selected from the group consisting of a linear nucleic acid, branched nucleic acid, an inverted nucleic acid and a peptide-nucleic acid, or a combination of any of the foregoing. The nucleic acid polymer comprises at least one purine or pyrimidine base comprising one negatively charged chemical moiety in one or both strands of the polymer.

This invention further contemplates and embraces compositions and kits for use in the variously described processes above.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Isothermal Amplification of PCR Product by Bst Polymerase at 53° C. and 63° C.

(i) PCR Amplification of HBV Plasmid DNA

The HBV positive control from the HBV Microtitre Plate Assay (ENZO Diagnostics, NY, N.Y.) was used as a target for amplification by PCR. According to the manufacturer, this DNA is 80 pg/ul (the equivalent of $1.2 \times 10^7$ copies of HBV per ul). A 50 ul PCR reaction was carried out consisting of 1 ul of HBV target, 1× PE buffer (Perkin-Elmer, Emeryville, Calif.), 4 mM $MgCl_2$, 250 um dNTP, 6 units of Amplitherm (Invitrogen, LaJolla, Calif.) and 10 pMoles of HBV oligo primers FC and RC.

```
FC Sequence =
5'-CATAGCAGCA GGATGAAGAG GAATATGATA GGATGTGTCT

GCGGCGTTT-3'

RC Sequence =
5'-TCCTCTAATT CCAGGATCAA CAACAACCAG AGGTTTTGCA

TGGTCCCGTA-3'
```

In this example, the 29 bases at the 3' end of the FC primer and the 30 bases at the 3' end of the RC primer are first segments that are capable of extension using HBV target DNA as a template. The 30 bases at the 5' end of the FC and RC primers are second segments that are complementary to the first 30 bases synthesized by extension of the primers using HBV DNA as a template. Thermocycling conditions were 30 cycles of 94° C. for 1', 56° C. for 15", and 68° C. for 30". Based on the HBV sequence, the anticipated PCR product should be 211 bp in length. Stem-loop structures are possible at each end of this product with 30 base pair stems contributed by the second segment and its complement and 29 and 30 base loops contributed by the FC and RC first segments respectively.

(ii) Analysis of PCR Product

The amplification was assayed by gel electrophoresis of a 10 ul sample in a 4% Metaphor agarose gel (FMC BioProducts, Rockland, Me.) that was run with 0.5×TBE buffer in the presence of 0.5 ug/ml Ethidium Bromide. Under UV illumination, three bands appeared that as judged by DNA size markers were approximately 210, 180 and 170 bp in length. The band corresponding to 210 bp is the linear PCR product that had been anticipated and presumably the other two bands correspond to the same size amplicons where secondary structures are formed on either one or both ends thereby changing their effective mobilities.

iii) Isothermal Amplification of the PCR Product 5 ul of various dilutions of the PCR product from above were used in a 100 ul reaction mix consisting of 1×ThermoPol buffer (NE Biolabs, Beverly, Mass.), 200 uM dNTP, 20 pMoles of Forward and Reverse Primers, 8 units Bst Polymerase (NE Biolabs, Beverly Mass.). The Forward Primers were either FC or LFC, the Reverse Primers were either RC or LRC. The sequences of the FC and RC primers have been given above. The LFC and LRC primers have sequences that correspond to the first segments only of the FC and RC primers. As such their sequences are as follows:

```
LFC = 5'-GGATGTGTCT GCGGCGTTT-3'

LRC = 5'-AGGTTTTGCA TGGTCCCGTA-3'
```

Incubations were for 30 minutes, 180 minutes or overnight incubations. Temperatures for the reactions were either 53° C. or 63° C. The 30 minute reactions were analyzed by gel electrophoresis with a 2% agarose gel; the 180 minute reactions were analyzed with 4% Metaphor agarose.

The results of this analysis are shown in FIG. 17. In the first set of samples taken after 30 minutes of incubation, only the $10^{-2}$ dilution of the PCR product shows any synthesis at 53° C. whereas the reactions from the 63° C. show synthesis in the $10^{-2}$, $10^{-3}$ and $10^{-4}$ dilutions. These data demonstrates that the amount of synthesis is dependent upon the amount of input target DNA. In the set of samples taken after 180 minutes of synthesis there is substantially more synthesis. The product of these reactions is a series of bands that form a discrete pattern. This is in contrast to a single discrete band that is usually seen in PCR or the two or three bands seen previously with the LC and RC primers after PCR amplification. This multiplicity of bands may possibly be due to the presence of the secondary structures allowing the amplicons to function as primers as well as templates or it may be an indication of strand switching. After incubation at 53° C. for three hours, even the control without any target shows evidence of substantial synthesis. However, it can be noted that there is a single target dependent pattern that is seen in all the 53° C. reactions with target template and the pattern present in the no target control is substantially different, presumably due to having a different pathway from the target initiated synthesis. The 63° C. incubations show substantial synthesis at all dilutions of the template and demonstrate the same pattern produced by the 53° C. reactions. However, in this experiment, there was no evidence at 63° C. for target independent amplification. The presence of substantial amounts of synthesis at even the $10^{-5}$ dilution is an indication that the system is capable of substantial amplification. The overnight incubations were also analyzed by gels and showed the same patterns and amounts as the 3 hour incubations (data not shown).

Example 2

Timecourse/Sensitivity of Isothermal Amplification of HBV Sequences i) Amplification HBV plasmid DNA previously digested with Eco R1 was used as a template for isothermal amplification. DNA Mixtures consisted of 100 ul containing 40 pM each of FC and RC primers, 1×ThermoPol Buffer (N.E. Biolabs, Beverly Mass.) and using a Model 480 thermocycler from Perkin-Elmer (Emeryville, Calif.). The machine was then set for 480 minutes at 63° C. After the block had adjusted to 63° C., individual tubes containing 25 ul of Enzyme Mix were put into the thermocycler block. Each tube of Enzyme Mix contained 4 units of Bst polymerase (N.E. Biolabs, Beverly Mass.), 1×ThermoPol Buffer (N.E. Biolabs, Beverly Mass.) and 400 uM dNTP's. After the DNA Mixtures and Enzyme Mixes had adjusted to 63° C., 25 ul samples were taken from each DNA Mixture and added to each Enzyme Mix tube for a total volume of 50 ul each. For each tube of DNA Mixture, three samples were taken. One sample for each DNA concentration was taken out of the 63° C. block after 2, 4 and 8 hours.

ii) Assay for Amplification

To distinguish between target dependent amplification and target independent amplification, microtitre plate assays were used to detect the presence of target specific sequences. The reagents and directions of use for this assay were taken from the HBV Microtitre Plate.Assay from ENZO Diagnostics (Farmingdale, N.Y.) with the substitution of plates and signal probes specific for the amplicon made by LC and RC primers.

iii) Preparation of Microtitre Plates

Plates were prepared in a batch process that used 5 frames with 12 (Dynel?) strips (manufacturer) in each. The sequence of the capture oligonucleotide used for these plates was derived from a region of HBV that is in between the FC and RC primers and is described as follows:

```
5'-CTCATCTTCT TATTGGTTCT TCTGGATTAT CAAGGTAT-3'
```

Each well of the microtitre plate was rinsed twice with 200 ul of 1 M Ammonium acetate and then left inverted at room temperature for 2 hours. A 10 ul solution containing 100 uM of the capture oligonucleotide described above was mixed with 27.5 ml of 1 M Ammonium acetate. 50 ul of this solution was added to each well and the plates were incubated overnight at 37° C. in an incubator with an open container of 1 M Ammonium acetate. The next day, each well was washed once with 200 ul of 1 M Ammonium acetate and the plates dried overnight. Strips that were then placed in a pouch with dessicant for future use.

iv) Preparation of Probe

The RC oligonucleotide used as a primer for the amplification was also used as the signal probe for the plate assay. T-tailing of 100 uM of the RC oligonucleotide was carried out by use of a Terminal Tailing kit from ENZO Diagnostics (Farmingdale, N.Y.). 26 ul of the tailed RC oligonucleotide was mixed with 12.8 ml Signal probe buffer (33% Deionized Formamide, 5 mM EDTA (pH 8.0), 1% Triton X-100, 2.5% Dextran Sulfate, 0.15 M NaCl, 0.12 M HEPES (free acid), 0.01% phenol Red).

e) The results of the microtitre plate assay with the samples from the reactions are given below:

|  | 2 Hours | 4 Hours | 8 Hours |
| --- | --- | --- | --- |
| 1 × $10^6$ targets | 0.413 | 1.491 | 1.419 |
| 1 × $10^4$ targets | 0.203 | 0.098 | 1.017 |
| No target | 0.086 | 0.085 | 0.063 |

As can be seen above, the amount of product was related to both the amount of initial target and the amount of time the reaction proceeds. There was also no signal generated from any products formed in the absence of target. Also, in this assay values of 1.4 or greater are saturation values and the amount of product can be much greater. Assessment of the total amount of product would require dilutions of the product until it was in the dynamic range of the assay. However, for the purposes of this example this was not done. The amplification reactions previously described are not dependent upon the use of Bst polymerase. When a different enzyme, Bca polymerase (PanVera, Madison, Wis.) was substituted, substantial amounts of synthesis could also be seen in the plate assay (data not shown). In addition, the temperature maximum for the Bst reaction appeared to be 63° C. but when the Bca polymerase was substituted, amplification could be achieved at 68° C. According to the literature that accompanied each enzyme, the optimal temperature for the Bst and Bca polymerases is 65° C. and 70° C. respectively. This may account for the 5° C. differences in their maximal temperatures.

Example 3

Amplification with ΔTth Polymerase

Due to the heat lability of the the Bst or Bca polymerases, the reactions in the previous examples, had to be carried out in two steps. The denaturation of target DNA was carried out in the absence of the polymerase followed by addition of the enzyme after equilibration at a lower temperature. It would be desirable to be able to include the polymerase in the initial step so as to reduce the handling steps and to reduce the chances of amplicon carryover contamination. Therefore, conditions were established that allowed the use of a 5'-3' Exo derivative of Tth polymerase to carry out isothermal amplification. In this particular example, two primers designated FJ and RJ were used that had the following sequences:

```
FJ Sequence =
5'-CATAGCAGCA GGATGAAGAG GAATATGATA GCT GGATGTGTCT

GCGGCGTTT-3'

RJ Sequence =
5'-TCCTCTAATT CCAGGATCAA CAACAACCAG TGC AGGTTTTGCA

TGGTCCCGTA-3'
```

Each of these primers are similar to the FC and FJ primers described previously except that they each have three more nucleotides (underlined above) in their first segments. Reactions were set up with $1\times10^6$, $1\times10^4$, or $1\times10^2$ HBV target molecules. One reaction contained 50 ng of T7 DNA instead of HBV DNA and this was used as the no target control. Reaction conditions were as follows: limit the Isothermal amplification had to be carried out in two phases the first step was a high temperature 94° C. denaturation of target molecules.

Amplification with ΔTth Polymerase

Due to the heat lability of the the Bst or Bca polymerases, the reactions in the previous examples, had to be carried out in two steps. The denaturation of target DNA was carried out in the absence of the polymerase followed by addition of the enzyme after equilibration at a lower temperature. It would be desirable to be able to include the polymerase in the initial step so as to reduce the handling steps and to reduce the chances of amplicon carryover contamination. Therefore, conditions were established that allowed the use of a 5'-3' Exeo derivative of Tth polymerase to carry out isothermal amplification. In this particular example, two primers designated FJ and RJ were used that had the following sequences:

```
FJ Sequence =
5'-CATAGCAGCA GGATGAAGAG GAATATGATA GCT GGATGTGTCT

GCGGCGTTT-3'

RJ Sequence =
5'-TCCTCTAATT CCAGGATCAA CAACAACCAG TGC AGGTTTTGCA

TGGTCCCGTA-3'
```

Each of these primers are similar to the FC and FJ primers described previously except that they each have three more nucleotides (underlined above) in their first segments. Either isothermal or PCR reactions were carried out with $1\times10^6$, $1\times10^4$, or $1\times10^2$ HBV target molecules in a 50 ul reaction volume. A no target control was also included that contained 50 ng of T7 DNA instead of HBV DNA. Each target concentration was setup in a 100 ul reaction mixture that contained 10 units of ΔTth polymerase (Clutch Laboratories, Palo Alto, Calif.), 1×ΔTth polymerase buffer (Clutch Laboratories, Palo Alto, Calif.), 250 uM dNTP, 2.5 mM $MgCl_2$, 1×PCR Enhancer (Epicentre Technologies, Madison, Wis.) and 20 pmoles each of FJ and RJ primers. Each mixture was divided into two 50 ul portions. One 50 ul portion was used in an isothermal reaction by heating to 94° C. for 5 minutes followed by 240 minutes at 68° C. in a thermocycler. The other portion was maintained at 4° C. until the isothermal reaction was finished and the thermocycler was used to carry out PCR with this portion with 35 cycles of 94° C. for 1 minute and 68° C. for 45 seconds.

Figure 18:
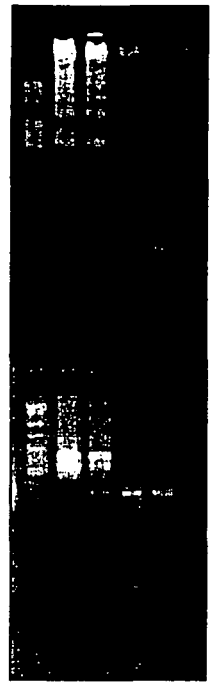
FIG. 18 are results of a gel assay and a plate assay for isothermal amplification of HPV plasmid DNA.

The extent of the isothermal reaction was measured by gel electrophoresis and plate assays as described in the previous examples. The plate assay was carried out as described previously except that the T-tailed probe was derived from the LFC primer. Results from each of these methods are shown in FIG. 18. The gel electrophoresis shows extensive synthesis with the $1\times10^6$ and $1\times10^4$ target reactions after isothermal amplification. Although it does not show up well in a photograph, the gel also showed a lesser level of amplification with the $1\times10^2$ target reaction. The PCR reactions were also examined in the same gel and show essentially similar results with high levels of amplification with the $1\times10^6$ and $1\times10^4$ target reactions. Under these conditions there is also seen a non-specific reaction that created a smaller amplicon that increased inversely with the amount of synthesis of the appropriate amplicon. When the isothermal reactions were also assayed by the plate assay, the higher levels of targets gave saturation levels and it can be clearly seen that the $1\times10^4$ target level gave a positive reaction. It should be noted that the negative control showed no signs of signal generation by either of the two assays.

Example 4

Use of a Single Primer for Amplification

Each sample consisted of a 50 ul reaction containing 1×Taq Buffer (Perkin Elmer, Emeryville, Calif.), 5 mM $MgCl_2$, 200 uM dNTPs, and 5 units of Amplitaq Gold (Perkin Elmer, Emeryville, Calif.). Each reaction also had 5 pM of an oligonucleotide primer with the following sequence:

```
5'CCTGCTGCTA TGCCTCATCT GACAAACGGG CAACATACCT

CCTGCTGCTA TGCCTCATCT-3'
```

Single primer amplifications were carried out in duplicate with or without target DNA (1 ul of the control HBV described previously in Example 1). Reactions were carried out in a thermoycler with one cycle of 94° C. followed by 50 cycles of 94° C. for 1 minute, 60° C. for 15 seconds and 68° C. for 15 seconds. To reduce non-specific priming, samples were not added to the thermocycler block until it reached 90° C. during the first cycle.

The extent of the reactions was analyzed by microtitre plate assays using the same plates, probe and format described in Example 2. The results of the reactions (in duplicate) were as follows:

| HBV+ | 1.407 | 0.377 |
| No Target | 0.083 | 0.087 |

As can be seen above, although there was some variation in the amount of signal generated from the duplicate reactions, there was a clear indication of the presence of target sequences after carrying out amplification with a single primer.

Example 5

Primer Extension with Carboxy-dUTP i) Synthesis of Carboxy-dUTP

A 5 ml solution containing 100 uMoles of allylamine-dUTP (ENZO Diagnostics, Farmingdale, N.Y.) in 0.2 M Sodium Borate buffer (pH 9.2) was mixed with a 20-fold molar excess of Succinic Anhydride (Aldrich, Milwaukee, Wis.) dissolved in 5 ml of Dichloro Methane (Aldrich, Milwaukee, Wis.). This suspension was transferred to a 50 ml Falcon tube and vortexed. The pH of the aqueous phase was readjusted to a value of of 9.2 by addition of appropriate amounts of Triethylamine (Aldrich, Milwaukee, Wis.). Shaking and readjustment was continued until the pH value stabilized. An aliquot was taken and tested by HPLC for the disappearance of the allylamine peak and the appearance of a later peak that represented the carboxy-modified product. The aqueous phase was removed and diluted 10-fold with $H_2O$ and loaded onto a DEAE-Sephadex A-50 column pre-equilibrated with 0.05 M Triethylammonium Bicarbonate buffer (pH 7.8). The product was eluted by a 0.05 M-0.70 M gradient of Triethylammonium Bicarbonate. Fractions were collected and analyzed by UV absorption at 290 nM. Appropriate fractions were checked by HPLC for purity. Fractions with >99.5% purity were pooled together and salts removed in a rotary evaporator in vacuum at 30° C. The remaining solids were dissolved in an appropriate amount of $H_2O$ and adjusted to a final concentration of 10 mM as judged by absorption at 290 nM. Aliquots were prepared and store at −70° C. until used.

ii) Primer Extension Reactions

The template for primer extension was single-stranded DNA obtained by PEG precipitation of phage particles from an mp18 clone that contained a 1.4 kb insert of HBV. The primer for extension was PM-1 whose sequence is complementary to part of the lac region of the mp18 vector. The sequence from this primer was:

```
5'-CGC CAG GGT TTT CCC AGT CAC GAC-3'
```

A 300 ul DNA Mixture was made that contained 7.5 ug of the single-stranded DNA and 60 pM of the PM1 primer. Separate 25 ul Enzyme mixes were made that contained 0.5 ul of polymerase, 2×buffer and 200 nM dNTP where for each condition one reaction had normal TTP and one reaction had carboxy-dUTP. 25 ul of the DNA Mixture was mixed with 25 ul of an Enzyme mix and incubated at the appropriate temperature for 30 minutes.

The following polymerases were used in this example: Exeo(−) Klenow (Q units/ml from NE Biolabs, Beverly, Mass.), Taq polymerase (T units/ul from GIBCO BRL, Gaithersburg, Md.), and Bst polymerase (4 units/ul from NE Biolabs, Beverly, Mass.)

Buffers and their compositions are as follows:

1×NEBuffer 2 (N.E. Biolabs, Beverly, Mass.) consists of 10 mM Tris-HCl, 10 mM $MgCl_2$, 50 mM NaCl and 1 mM DTT (pH 7.9 at 25° C.)

Buffer 2A was the same as NEBuffer 2 except the pH is 7.1 and the $MgCl_2$ was only 2 mM.

Buffer 2M was the same as NEBuffer 2 except the $MgCl_2$ was only 2 mM and 1 mM $MnSO_4$ was also included.

1×ThermoPol Buffer (N.E. Biolabs, Beverly, Mass.) consists of 20 mM Tris-HCl (ph 8.8 at 25° C.), 10 mM KCl, 10 mM $(NH_4)_2SO_4$, 2 mM $MgSO_4$ and 0.1% Triton X-100.

iii) Analysis of Primer Extension Reactions

Assessment of the ability of the various polymerases to utilize the carboxy-dUTP as a substrate can be carried out in a number of different ways. In the present example, this was qualitatively observed without the use of labeled precursors by evaluation of the conversion of the single-stranded DNA into a double-stranded form by gel analysis. This conversion event can be seen by a retardation in its migration in an agarose gel compared to the single-stranded precursor and by an increased fluorescence due to its ability to bind Ethidium Bromide more efficiently. Although this method was used in the initial assessments of studies on carboxy-dUTP incorporation, more information can be obtained by digesting the extension products with a restriction enzyme. Since the particular restriction enzyme used for this analysis is unable to digest single-stranded DNA, production of fragments is an indication of a double-stranded region at the restriction enzyme site. By reduction of the circular DNA into linear pieces, it becomes easier to make comparative assessments of the amount of conversion by the different polymerases. In addition since the positions of the various restriction fragments are known relative to the primer, it allows an evaluation of the length of the extended product.

iv) Digestion with Restriction Enzymes

Since the templates from the primer extension reactions consisted of unmodified DNA, the carboxy-dUTP reactions contain one strand that is normal and a complementary strand that is substituted completely with the carboxy-dU derivative producing a hemi-substituted restriction site wherever T's are part of the recognition site. The enzyme used for the evaluation was BstN1 whose recognition sequence is GG A/T CC. The computer program MacDNASIS (Hitachi Software Engineering America, Ltd, South San Fransisco, Calif.) was used to predict the locations of the individual GG(T)CC and GG(A)CC sites.

v) Analysis of Reactions

Figure 19:
FIG. 19 shows the results of a gel assay for PCR reactions with carboxy dUTP and normal dTTP under various reaction conditions defined therein.

FIG. 19 shows the results of extension reactions with various buffers, enzymes and temperatures. First off it can be noted that the reactions with the unsubstituted dNTP form a different pattern from the reactions with carboxy-dUTP. Analysis of the positions of the GG(T)CC and GG(A)CC sequences in the products showed that the pattern from BstN1 digestion of the unsubstituted reactions was due to the expected digestion at both the GG(T)CC and GG(A)CC sites but the carboxy-dUTP reactions only exhibited digestions at the GG(A)CC sequences. A reaction was also carried out using dUTP as a substrate and there was digestion at all sites showing that it was the presence of the carboxy and its linker rather than the use of dU that was the cause of the resistance to digestion by BstN1 (data not shown). FIG. 20 is a compilation of the results from FIG. 19 with relative levels of synthesis rated from (−) for no synthesis, (+/−) for barely visible and on up to a rating of (++++). In general the best synthesis for carboxy-U incorporation was seen with the Bst polymerase/Thermopol Buffer conditions.

Example 6

Effects of Carboxy-U on Mg++ Requirements in PCR

Figure 21:
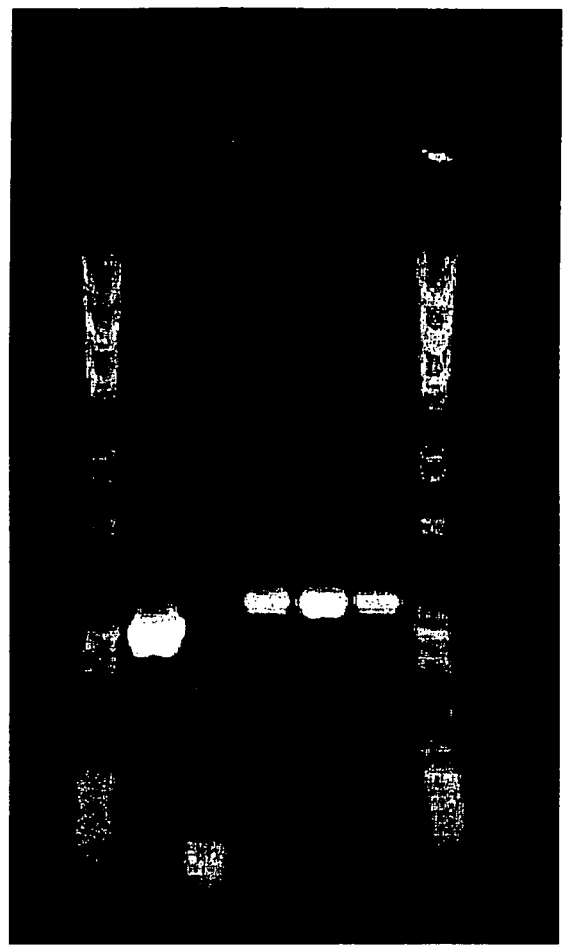
FIG. 21 shows the effects of various levels of $MgCl_2$ on PCR synthesis in the presence of carboxy dUTP.

PCR amplification was carried out with double-stranded T7 DNA as a template and two oligonucleotides TS-1 and TS-4 as primers. These oligonucleotides have been previously described in U.S. patent application Ser. No. 08/574,443, filed on Dec. 15, 1995 and produce a 622 base pair product. 100 ul reactions were carried out that consisted of 400 ng of T7 DNA, 50 pM of TS-1, 50 pM of TS-4, 1×PE Buffer (BRL) 200 mM dNTP, and 15 units of Taq Polymerase (GIBCO BRL, Gaithersburg, Md.). Cycle conditions were 25 cycles of 94° C. for 50 seconds, 50° C. for 25 seconds and 68° C. for 3 minutes. FIG. 21 shows the results of this synthesis. When normal nucleotides were used as substrates for the reaction, 1 mM $MgCl_2$ was adequate for amplification. In contrast, when the reaction was carried out with carboxy-dUTP, 2 mM $MgCl_2$ produced only dimers of the oligos and a minimum of 3 mM $MgCl_2$ was necessary for synthesis of the appropriately sized amplicon.

Example 7

Various Thermostable Polymerases

Figure 22:
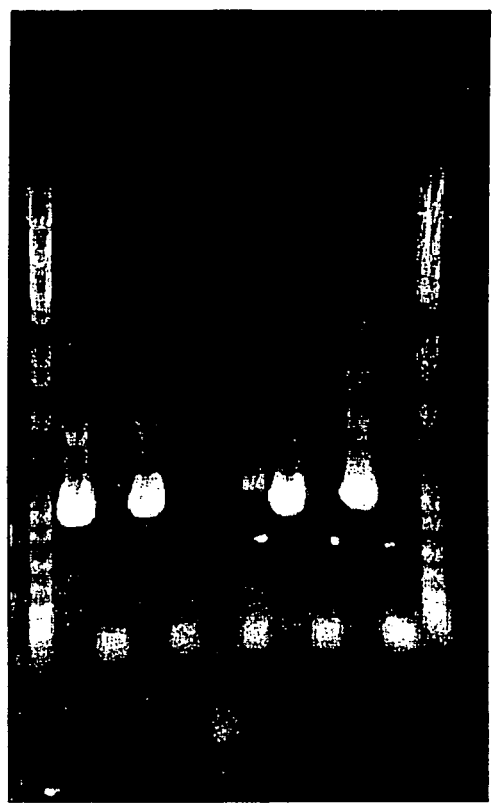
FIG. 22 are the results of a gel assay for the ability of various polymerases to carry out PCR synthesis in the presence of carboxy dUTP.

Amplification was carried out as described in Example X-22 except that all reactions were carried out in the presence of 3 mM $MgCl_2$ and only 5 units of polymerase was used for each reaction. Taq polymerase (GIBCO BRL, Gaithersburg, Md.) was compared to Tfl, Tth, Amplitherm and Replitherm polymerases (all from Epicentre, Madison Wis.). All reactions used the buffers that came with each enyzme. Gel analysis of the reactions is shown in FIG. 22. Lowering the amount of Taq gave a considerable reduction of synthesis in the presence of the carboxy-UTP compared to the reaction seen in Example 6. There was no effect at all seen with the normal TTP. For the other polymerases, the only one that gave any appreciable amount of product was the Tth polymerase and this was more active than the Taq polymerase under the conditions used.

Example 8

Figure 23:
FIG. 23 shows the effects of various levels of $MgCl_2$ on PCR synthesis in the presence of carboxy dUTP with various enzymes.
Figure 24:
FIG. 24 shows the effects of various levels of $MgCl_2$ on PCR synthesis in the presence of carboxy dUTP and PCR Enhancer with various enzymes.

In Example 7, the reactions with the various polymerases were carried out in the presence of 3 mM $MgCl_2$. However, the lack of synthesis by some of these polymerases may reflect a different Mg++ concentration requirement when carboxy-UTP is a substrate. One of the enzymes that showed no synthesis in the presence of carboxy-UTP but gave extensive synthesis with normal TTP was the Tfl polymerase. This enzyme was tried under the same reaction conditions described above but 2 mM, 4 mM and 6 mM $MgCl_2$ levels were used for the reactions. In addition, the same titration was used with Taq polymerase (Perkin-Elmer, Foster City, Calif.) in PE Buffer (Perkin-Elmer, Foster City, Calif.) and with Tfl polymerase with the addition of 5 ul of PCR Enhancer (Stratagene, La Jolla, Calif.). The results of this are shown in FIG. 23. Under the conditions used, 6 mM $MgCl_2$ gave the best amount of synthesis for the Taq polymerase and the Tfl alone showed no synthesis with 2, 4 or 6 mM $MgCl_2$. However, when PCR Enhancer was included in the reaction, the Tfl polymerase was able to generate appreciable amounts of synthesis. Similar to Taq, the highest level was achieved with 6 mM $MgCl_2$. The level of synthesis shown for the Tfl/PCR Enhancer reaction was also higher than the Taq reaction. PCR Enhancer was tried with the other thermostable polymerases Tth, Amplitherm and Replitherm for amplification with the carboxy-UTP. The results of this are shown in FIG. 24. Although it was unable to rescue amplification by the Amplitherm polymerase, there was now synthesis shown for the Replitherm polymerase. The Tth polymerase, which other than Taq was the only polymerase to show amplification with the carboxy-UTP in Example 7, showed the highest level of amplification with the PCR Enhancer. Also, for the Tth/PCR Enhancer series, the reaction with 8 mM $MgCl_2$ gave more amplification than 6 mM $MgCl_2$ reaction.

Example 9

Variations in the Thermal Conditions of Amplification

Two oligonucleotides, TS13 and TS14, that have also been described in ENZ (?) were used for amplification of a different segment of bacteriophage T7 DNA in the presence of carboxy-dUTP. The product of these primers is a 136 bp amplicon that is smaller than the product synthesized in the previous examples. A sequential series of PCR reactions were carried out in two phases. Each reaction used the Tth polymerase as well as the PCR Enhancer described above. The first phase in each reaction was a series of 5 cycles using the cycling conditions described above to create templates containing carboxy-dU in both strands. The second phase in each reaction used various lower temperatures for the annealing, elongation or denaturation steps. Preliminary attempts at varying temperatures showed that temperatures below 80° C. were unsuccessful in carrying out amplification with this amplicon so that efforts to close the difference between the highest and lowest temperature were made by raising the annealing temperature. For each set of temperature conditions, the $MgCl_2$ level was also varied. A compilation of results derived from a gel analysis of three sets of these reactions is given below:

| Denaturation | Annealing | Extension | $MgCl_2$ | Synthesis |
|---|---|---|---|---|
| a) 80° C. 2' | 55° C. 25" | 68° C. 2' | 5 mM | ++ |
|  |  |  | 4 mM | + |
|  |  |  | 3 mM | +/− |
| b) 80° C. 2' | 60° C. 25" | 68° C. 2' | 6 mM | − |
|  |  |  | 5 mM | − |
|  |  |  | 4 mM | ++ |
| c) 80° C. 2' | 65° C. 25" | 70° C. 2' | 6 mM | − |
|  |  |  | 4 mM | ++ |
|  |  |  | 2 mM | ++ |

Figure 25:
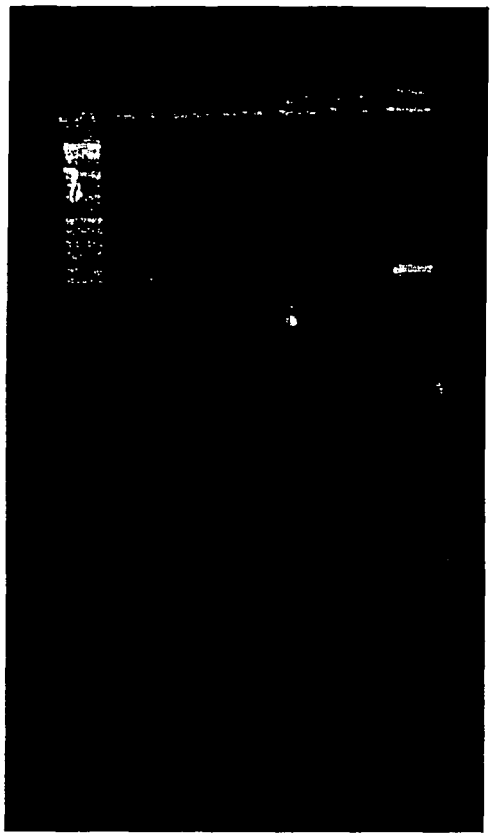
FIG. 25 shows the effects of various additives on PCR synthesis in the presence of carboxy dUTP.

In addition to the reactions above, a series of reactions was carried out with a denaturation step of 80° C. for 2' combined with an annealing/extension step of 68° C. for 2'. Various factors were also included with this compressed cycle to see if the efficiency of the reaction could be augmented. A gel with the products from these reactions is shown in FIG. 25. It can be seen that with as small a difference as 12° C. between the highest and lowest temperatures there was still amplification of the amplicon and the only factor that seemed to enhance synthesis under these thermal conditions was the addition of extra polymerase.

Example 9

Effect on Compressed Thermal Amplification Conditions by Variations in the Primer Sequence

In addition to the TS13 and TS14 primers described above, primers were designed that had variations of these sequences to see if the range between the highest and lowest temperatures could be further compressed. The sequences for TS13, TS14 primers and their variants as well as the region of the T7 genome from which they were derived is shown in FIG. 26. The differences in the sequences of these primers made some small changes in the size of the amplicon but essentially the same T7 segment was amplified in each of the reactions with these primers.

Figure 27:
FIG. 27 are the results of a gel assay for various combinations of primers for PCR synthesis in the presence of carboxy dUTP.

A series of reactions were carried out using various combinations of the primers from FIG. 26. With 20 cycles of 80° C. for 2' and 68° C. for 2'30", there was only a 12° C. separation between the denaturation step and the annealing/extension step. A gel analysis of these reactions is shown in FIG. 27. All of the primer combinations demonstrated amplification of an appropriate band although there were difference in their efficiencies. Controls were also included in this set of reactions where either normal dTTP or allylamine-dUTP was used in place of the carboxy-dUTP; these reactions gave no detectable levels of amplification.

Figure 28:
FIG. 28 are the results of a gel assay for various combinations of primers for PCR synthesis in the presence of carboxy dUTP at different temperatures shown therein.

The same combinations of primers were tried in amplification reactions with 20 cycles of 80° C. for 2' and 72° C. for 2'30". A gel analysis of these reactions is shown in FIG. 28. Under these thermal conditions, most of the primer combinations failed to amplify. However, all of the reactions that included the TS23 primer as one of the primer pairs gave amplification. In regard to the other primers that were used in conjunction with the TS23 primer, the relative levels of amplification were in the order of TS21>TS22>TS13. Although there may be other factors involved, this ordering may be related to an inverse relationship to the numbers of carboxy-dUTP moieties present in the segments of the template strands where the primers bind since this would be 10, 11 and 14 respectively for the TS21, TS22 and TS13 primers. The results shown in FIG. 28 show that when carboxy-dUTP is used as a substrate, amplification can be carried out with only an 8° C. difference between the denaturation and annealing/extension temperatures.

Example 10

Post Synthesis Modification of a Primer Extension Product

A primer extension reaction was carried out in the presence of allyl amine dUTP. The template for the reaction had the following sequence:

5'-AGGTAACTTA AGATGGTCAG GCTGAAAGGA GGAACTATATC TGCAGAA-3'

The primer used for the reaction was TS 14 which has previously been described. Reaction mixtures consisted of 1 ul of TS14 primer (100 pmoles), 1 ul of template (100 pmoles), 2 ul of 25 mM $MgCl_2$, 2 ul of 400 uM dGTP/dCTP/dATP, 2 ul allylamine ddUTP (ENZO Diagnostics, Farmingdale, N.Y.), 1 ul of Amplitaq DNA polymerase (Perkin-Elmer, Emeryville, Calif.), 1-3 ul of TAPS buffer and 0-2 ul of $H_2O$) for a final volume of 12 ul for each reaction. TAPS buffer consisted of 200 mM TAPS (SIGMA, St. Louis, Mo.), 500 mM KCl with a ph of 9.6 unless otherwise indicated. Reactions had various levels of TAPS buffer and the pH was also varied. The particulars for each reaction are given in and amount of in the reactions were assessed and are described in FIGS. 29 and 30. As a control reactions were also included that contained no enzyme or used Fluorescein ddUTP (ENZO Diagnostics, Farmingdale, N.Y.) instead of the allylamine ddUTP. Reaction mixes were heated to 94° C. for 1 minute and then incubated at 68° C. for one hour.

Reactions were centrifuged briefly in a microfuge and 1 ul of 50 mM Fluoroscein-5(6) carboxamido-caproic acid N-Hydroxysuccinimide ester (Fl-NHS ester) was added to each reaction and incubated at 37° C. for three hours. Extent of synthesis and labeling were assessed by acrylamide gel electrophoresis. Fluorescent labeling was identified by putting the gel on a UV illuminator and taking a Polaroid picture using a Wratten 58 Kodak Filter (SIGMA, St. Louis, Mo.). The gel was then stained in Ethidium Bromide for 20 minutes followed by destaining for 20 minutes and a picture taken using the normal filter. FIG. 29 shows the fluorescence provided by the incorporated fluoroscein (top gel) and Ethidium Bromide staining (bottom gel) for each of the various reaction conditions. The photographs of these gels were also scanned and a photonegative made of each of them. The results of this are shown in FIG. 30. The photonegative provides a better assessment of the results of the experiment. It can be seen in the upper photo that there is an extension product made that is capable of generating a fluorescent signal under the various conditions used in the reactions. The highest level seems to have been achieved with 3×TAPS at pH 9.7. This experiment also demonstrates that there is higher signal generation with the post-synthesis modification than the control that used ddUTP that was pre-modified with fluorescein (lane 8). The extent of synthesis seen in the lower gel also demonstrates the utility of this approach where it can be seen by the presence of the upper band in lane 8 that there was incorporation of the normal bases even though there was minimal incorporation of the pre-modified ddUTP.

Many obvious variations will be suggested to those of ordinary skill in the art in light of the above detailed description of the present invention. All such obvious variations are fully contemplated and embraced by the scope and spirit of the present invention as set forth in the claims that now follow.

What is claimed is:

1. A kit for isothermal amplification of a sequence of a nucleic acid analyte in a sample, said kit comprising:
- a first oligonucleotide primer comprising (i) a 3' terminal nucleotide sequence that anneals to a single-stranded nucleic acid analyte and serves as the origin of synthesis for synthesizing a first single-stranded nucleic acid molecule complementary at least in part to the sample single-stranded nucleic acid analyte when said nucleic acid analyte is present in said sample, and (ii) a 5' terminal nucleotide sequence that is complementary to an arbitrary region of the first single-stranded nucleic acid molecule, such that a stem loop can form between the 5' terminal nucleotide sequence and the complementary region of the first single-stranded nucleic acid molecule;
- a second oligonucleotide primer comprising a nucleotide sequence which anneals to a region of the single-stranded nucleic acid analyte located 3' to where the first oligonucleotide primer anneals thereto;
- a third oligonucleotide primer comprising (i) a 3' terminal nucleotide sequence that anneals to the first single-stranded nucleic acid molecule prepared using the first oligonucleotide primer and serves as the origin of synthesis for synthesizing a second single-stranded nucleic acid molecule complementary at least in part to the first single-stranded nucleic acid molecule, and (ii) a 5' terminal nucleotide sequence that is complementary to an arbitrary region of the second single-stranded nucleic acid molecule, such that a stem loop can form between the 5' terminal nucleotide sequence and the complementary region of the second single-stranded nucleic acid molecule;
- a polymerizing enzyme having strand displacement activity;
- a positive control nucleic acid that comprises, in order, (a) a first sequence complementary to said second oligonucleotide primer, (b) a second sequence complementary to the 3' terminal nucleotide sequence of said first oligonucleotide primer, (c) a third sequence identical to the 5' segment of said terminal nucleotide sequence of said first oligonucleotide primer, (d) a fourth sequence complementary to the 5' segment of said terminal nucleotide sequence of said third oligonucleotide primer, and (e) a fifth sequence identical to the 3' terminal nucleotide sequence of said third oligonucleotide primer, and
- one or more nucleotides which are used by the polymerizing enzyme to extend the primers, wherein the complementarity of said 5' terminal nucleotide sequence in said first oligonucleotide primer with sequences generated by extension of said first oligonucleotide primer and the complementarity of said 5' terminal nucleotide sequence in said third oligonucleotide primer with sequences generated by extension of said third oligonucleotide primer isothermally amplifies sequences between the site on said nucleic acid analyte and said positive control nucleic acid that are complementary to the 3' terminal nucleotide sequence of said first primer and the site on said first single-stranded nucleic acid molecule that is complementary to the 3' terminal nucleotide sequence of said third primer, and
- said isothermal amplification is provided by stem loop formation of said first and third oligonucleotide primers after template dependent primer extension.

2. The kit according to claim 1, further comprising: a fourth oligonucleotide primer comprising a nucleotide sequence which anneals to a region of the first single-stranded nucleic acid molecule located 3' to where the third oligonucleotide primer anneals thereto.

3. The kit according to claim 1, wherein said polymerizing enzyme comprises a DNA polymerase, RNA polymerase, reverse transcriptase, DNA ligase, or a combination of any of the foregoing.

4. The kit according to claim 1, wherein said DNA polymerase has reverse transcriptase activity.

5. The kit according to claim 1, further comprising reagents for carrying out strand extension.

6. The kit according to claim 1, further comprising a detector that generates a change in signal from primer extension.

7. The kit according to claim 1, wherein any of said oligonucleotide primers comprise a detectable label or labels.

8. The kit according to claim 1, wherein said one or more nucleotides are labeled.

9. The kit according to claim 1, further comprising a detector for detection of a product of nucleic acid synthesis.

10. The kit according to claim 1, further comprising a melting temperature regulator.

11. The kit according to claim 10, wherein the melting temperature regulator comprises betaine.

12. The kit according to claim 11, wherein said betaine comprises an effective concentration thereof.

13. The kit according to claim 12, wherein the effective concentration of betaine in reaction solution is about 0.55 M.

14. A kit for amplifying a target nucleotide sequence under isothermal conditions, the kit comprising:
- a first oligonucleotide primer comprising (i) a 3' terminal nucleotide sequence that anneals to a single-stranded nucleic acid analyte and serves as the origin of synthesis for synthesizing a first single-stranded nucleic acid molecule complementary at least in part to the sample single-stranded nucleic acid analyte when said nucleic acid analyte is present in said sample, and (ii) a 5' terminal nucleotide sequence that is complementary to an arbitrary region of the first single-stranded nucleic acid molecule, such that a stem loop can form between the 5' terminal nucleotide sequence and the complementary region of the first single-stranded nucleic acid molecule;

a second oligonucleotide primer comprising a nucleotide sequence which anneals to a region of the single-stranded nucleic acid analyte located 3' to where the first oligonucleotide primer anneals thereto;

a third oliqonucleotide primer comprising (i) a 3' terminal nucleotide sequence that anneals to the first single-stranded nucleic acid molecule prepared using the first oligonucleotide primer and serves as the origin of synthesis for synthesizing a second single-stranded nucleic acid molecule complementary at least in part to the first single-stranded nucleic acid molecule, and (ii) a 5' terminal nucleotide sequence that is complementary to an arbitrary region of the second single-stranded nucleic acid molecule, such that a stem loop can form between the 5' terminal nucleotide sequence and the complementary region of the second single-stranded nucleic acid molecule;

a polymerizing enzyme having strand displacement activity; and one or more nucleotides which are used by the polymerizing enzyme to extend the primers, wherein the complementarity of said 5' terminal nucleotide sequence in said first oliqonucleotide primer with sequences generated by extension of said first oligonucleotide primer and the complementarity of said 5' terminal nucleotide sequence in said third oligonucleotide primer with sequences generated by extension of said third oligonucleotide primer isothermally amplifies sequences between the site on said nucleic acid analyte that are complementary to the 3' terminal nucleotide sequence of said first primer and the site on said first single-stranded nucleic acid molecule that is complementary to the 3' terminal nucleotide sequence of said third primer, and said isothermal amplification is provided by stem loop formation, at 53° C. or higher, of said first and third oliqonucleotide primers after template dependent primer extension.

15. The kit according to claim 14, further comprising: a fourth oligonucleotide primer comprising a nucleotide sequence which anneals to a region of the first single-stranded nucleic acid molecule located 3' to where the third oligonucleotide primer anneals thereto.

16. The kit according to claim 14, wherein said polymerizing enzyme comprises a DNA polymerase, RNA polymerase, reverse transcriptase, DNA ligase, or a combination of any of the foregoing.

17. The kit according to claim 14, wherein said DNA polymerase has reverse transcriptase activity.

18. The kit according to claim 14, further comprising reagents for carrying out strand extension.

19. The kit according to claim 14, further comprising a detector that generates a change in signal from primer extension.

20. The kit according to claim 14, wherein any of said oligonucleotide primers comprise a detectable label or labels.

21. The kit according to claim 14, wherein said one or more nucleotides are labeled.

22. The kit according to claim 14, further comprising a detector for detection of a product of nucleic acid synthesis.

23. The kit according to claim 14, further comprising a melting temperature regulator.

24. The kit according to claim 23, wherein the melting temperature regulator comprises betaine.

25. The kit according to claim 24, wherein said betaine comprises an effective concentration thereof.

26. The kit according to claim 25, wherein the effective concentration of betaine in reaction solution is about 0.55 M.

27. The kit according to claim 1, wherein said isothermal amplification is provided by stem loop formation, at 53° C. or higher, of said first and third oligonucleotide primers after template dependent primer extension.

28. A kit for isothermal amplification of a sequence of a nucleic acid analyte in a sample, said kit comprising:

a first oligonucleotide primer comprising (i) a 3' terminal nucleotide sequence that anneals to a single-stranded nucleic acid analyte and serves as the origin of synthesis for synthesizing a first single-stranded nucleic acid molecule complementary at least in part to the sample single-stranded nucleic acid analyte when said nucleic acid analyte is present in said sample, and (ii) a 5' terminal nucleotide sequence that is complementary to an arbitrary region of the first single-stranded nucleic acid molecule, such that a stem loop can form between the 5' terminal nucleotide sequence and the complementary region of the first single-stranded nucleic acid molecule;

a second oligonucleotide primer comprising (i) a 3' terminal nucleotide sequence that anneals to the first single-stranded nucleic acid molecule prepared using the first oligonucleotide primer and serves as the origin of synthesis for synthesizing a second single-stranded nucleic acid molecule complementary at least in part to the first single-stranded nucleic acid molecule, and (ii) a 5' terminal nucleotide sequence that is complementary to an arbitrary region of the second single-stranded nucleic acid molecule, such that a stem loop can form between the 5' terminal nucleotide sequence and the complementary region of the second single-stranded nucleic acid molecule;

a polymerizing enzyme having strand displacement activity;

a positive control nucleic acid that comprises, in order, (a) a first sequence complementary to the 3' terminal nucleotide sequence of said first oligonucleotide primer, (b) a second sequence identical to the 5' segment of said terminal nucleotide sequence of said first oligonucleotide primer, (c) a third sequence complementary to the 5' segment of said terminal nucleotide sequence of said second oligonucleotide primer, and (d) a fourth sequence identical to the 3' terminal nucleotide sequence of said third oligonucleotide primer, and one or more nucleotides which are used by the polymerizing enzyme to extend the primers, wherein the complementarity of said 5' terminal nucleotide sequence in said first oligonucleotide primer with sequences generated by extension of said first oligonucleotide primer and the complementarity of said 5' terminal nucleotide sequence in said second oligonucleotide primer with sequences generated by extension of said second oligonucleotide primer isothermally amplifies sequences between the site on said nucleic acid analyte and said positive control nucleic acid that are complementary to the 3' terminal nucleotide sequence of said first primer and the site on said first single-stranded nucleic acid molecule that is complementary to the 3' terminal nucleotide sequence of said second primer, and said isothermal amplification is provided by stem loop formation of said first and second oligonucleotide primers after template dependent primer extension.

29. The kit according to claim 28, further comprising a third oligonucleotide primer complementary to said analyte and said positive control nucleic acid.

30. The kit according to claim 29, wherein the region of said analyte and said positive control nucleic acid that is complementary to said third primer is 5' to where said first oligonucleotide primer binds to said analyte or said control nucleic acid and said third prime displaces said first oligonucleotide primer after said first oligonucleotide primer has undergone template dependent primer extension.

31. The kit according to claim 30, further comprising a fourth oligonucleotide primer complementary to a complementary copy of said analyte and said control nucleic acid.

32. The kit according to claim 29, wherein the region of said complementary copy of said analyte and said control nucleic acid that is complementary to said fourth primer is 5' to where said second oligonucleotide primer binds to said complementary copy and said fourth primer displaces said second oligonucleotide primer after said second oligonucleotide primer has undergone template dependent primer extension.

33. The kit according to claim 28, further comprising a third oligonucleotide primer complementary to a loop formed during said isothermal amplification.

34. The kit according to claim 33, further comprising a fourth oligonucleotide complementary to a loop formed during said isothermal amplification.

35. The kit according to claim 28, wherein said isothermal amplification is provided by stem loop formation, at 53° C. or higher, of said first and second oligonucleotide primers after template dependent primer extension.

* * * * *

SEQUENCE LISTING

<160> NUMBER OF SEQ ID NOS: 18

<210> SEQ ID NO 1
<211> LENGTH: 49
<212> TYPE: DNA
<213> ORGANISM: Hepatitis B virus

<400> SEQUENCE: 1
catagcagca ggatgaagag gaatatgata ggatgtgtct gcggcgttt            49

```
<210> SEQ ID NO 2
<211> LENGTH: 50
<212> TYPE: DNA
<213> ORGANISM: Hepatitis B virus

<400> SEQUENCE: 2
tcctctaatt ccaggatcaa caacaaccag aggttttgca tggtcccgta          50

<210> SEQ ID NO 3
<211> LENGTH: 19
<212> TYPE: DNA
<213> ORGANISM: Hepatitis B virus

<400> SEQUENCE: 3
ggatgtgtct gcggcgttt                                            19

<210> SEQ ID NO 4
<211> LENGTH: 20
<212> TYPE: DNA
<213> ORGANISM: Hepatitis B virus

<400> SEQUENCE: 4
aggttttgca tggtcccgta                                           20

<210> SEQ ID NO 5
<211> LENGTH: 38
<212> TYPE: DNA
<213> ORGANISM: Hepatitis B virus

<400> SEQUENCE: 5
ctcatcttct tattggttct tctggattat caaggtat                       38

<210> SEQ ID NO 6
<211> LENGTH: 52
<212> TYPE: DNA
<213> ORGANISM: Hepatitis B virus

<400> SEQUENCE: 6
catagcagca ggatgaagag gaatatgata gctggatgtg tctgcggcgt tt       52

<210> SEQ ID NO 7
<211> LENGTH: 53
<212> TYPE: DNA
<213> ORGANISM: Hepatitis B virus

<400> SEQUENCE: 7
tcctctaatt ccaggatcaa caacaaccag tgcaggtttt gcatggtccc gta      53

<210> SEQ ID NO 8
<211> LENGTH: 60
<212> TYPE: DNA
<213> ORGANISM: Hepatitis B virus

<400> SEQUENCE: 8
cctgctgcta tgcctcatct gacaaacggg caacatacct cctgctgcta tgcctcatct  60

<210> SEQ ID NO 9
<211> LENGTH: 23
<212> TYPE: DNA
<213> ORGANISM: Escherichia coli

<400> SEQUENCE: 9
cgccagggtt tcccagtcac gac                                       23
```

-continued

```
<210> SEQ ID NO 10
<211> LENGTH: 48
<212> TYPE: DNA
<213> ORGANISM: Hepatitis B virus

<400> SEQUENCE: 10
aggtaactta agatggtcag gctgaaagga ggaactatat ctgcagaa              48

<210> SEQ ID NO 11
<211> LENGTH: 70
<212> TYPE: DNA
<213> ORGANISM: Hepatitis B virus

<400> SEQUENCE: 11
tgcgctgcta acaaagcccg aaaggaaggc tgaaaggagg aactatatgg cgtcatacga  60
tatgaacgtt                                                         70

<210> SEQ ID NO 12
<211> LENGTH: 70
<212> TYPE: DNA
<213> ORGANISM: Hepatitis B virus

<400> SEQUENCE: 12
acgccaccat tgtttcgggc tttccttccg actttcctcc ttgatatacg cgagtatgct  60
atacttgcaa                                                         70

<210> SEQ ID NO 13
<211> LENGTH: 30
<212> TYPE: DNA
<213> ORGANISM: Hepatitis B virus

<400> SEQUENCE: 13
aatctagagc taacaaagcc cgaaaggaag                                   30

<210> SEQ ID NO 14
<211> LENGTH: 28
<212> TYPE: DNA
<213> ORGANISM: Hepatitis B virus

<400> SEQUENCE: 14
tgcgctgcta acaaagcccg aaaggaag                                     28

<210> SEQ ID NO 15
<211> LENGTH: 31
<212> TYPE: DNA
<213> ORGANISM: Hepatitis B virus

<400> SEQUENCE: 15
acccgcgctg ctaacaaagc ccgaaaggaa g                                 31

<210> SEQ ID NO 16
<211> LENGTH: 28
<212> TYPE: DNA
<213> ORGANISM: Hepatitis B virus

<400> SEQUENCE: 16
cgactttcct ccttgatata gacgtctt                                     28

<210> SEQ ID NO 17
<211> LENGTH: 27
<212> TYPE: DNA
<213> ORGANISM: Hepatitis B virus

<400> SEQUENCE: 17
```

```
cgactttcct ccttgatata cgcgagt                                          27

<210> SEQ ID NO 18
<211> LENGTH: 28
<212> TYPE: DNA
<213> ORGANISM: Hepatitis B virus

<400> SEQUENCE: 18
gatatacgcg agtatgctat acttgcaa                                         28
```